US012734196B2

(12) United States Patent
Bratt-Leal et al.

(10) Patent No.: US 12,734,196 B2
(45) Date of Patent: Sep. 15, 2026

(54) METHODS OF DIFFERENTIATING NEURAL CELLS AND RELATED COMPOSITIONS AND METHODS OF USE

(71) Applicant: Aspen Neuroscience, Inc., San Diego, CA (US)

(72) Inventors: Andres Bratt-Leal, San Diego, CA (US); Jeanne Loring, Del Mar, CA (US); Ha Tran, San Diego, CA (US); Roy Williams, Rancho Santa Fe, CA (US); Jim Mossman, San Diego, CA (US)

(73) Assignee: Aspen Neuroscience, Inc., San Diego, CA (US)

( * ) Notice: Subject to any disclaimer, the term of this patent is extended or adjusted under 35 U.S.C. 154(b) by 556 days.

(21) Appl. No.: 17/792,632

(22) PCT Filed: Jan. 13, 2021

(86) PCT No.: PCT/US2021/013324
§ 371 (c)(1),
(2) Date: Jul. 13, 2022

(87) PCT Pub. No.: WO2021/146349
PCT Pub. Date: Jul. 22, 2021

(65) Prior Publication Data

US 2023/0059010 A1 Feb. 23, 2023

Related U.S. Application Data

(60) Provisional application No. 62/960,669, filed on Jan. 13, 2020.

(51) Int. Cl.
*A61K 35/30* (2015.01)
*A61P 25/16* (2006.01)
*C12N 5/0793* (2010.01)

(52) U.S. Cl.
CPC .............. *A61K 35/30* (2013.01); *A61P 25/16* (2018.01); *C12N 5/0619* (2013.01); *C12N 2501/13* (2013.01); *C12N 2501/15* (2013.01); *C12N 2501/41* (2013.01); *C12N 2501/999* (2013.01); *C12N 2506/45* (2013.01)

(58) Field of Classification Search
CPC ..................................................... A61K 35/30
See application file for complete search history.

(56) References Cited

U.S. PATENT DOCUMENTS 5,033,252 A 7/1991 Carter
5,052,558 A 10/1991 Carter
5,323,907 A 6/1994 Kalvelage
5,538,848 A 7/1996 Livak
5,925,517 A 7/1999 Tyagi
6,174,670 B1 1/2001 Wittwer
6,326,145 B1 12/2001 Whitcombe
6,329,144 B1 12/2001 Kubista
6,635,427 B2 10/2003 Wittwer
7,510,687 B2 3/2009 Mazzeo
8,442,772 B2 5/2013 Loring
8,642,334 B2 2/2014 Chambers
9,453,198 B2 9/2016 Studer
9,926,529 B2 3/2018 Gonzalez
10,260,041 B2 4/2019 Chambers
10,273,452 B2 4/2019 Chambers
10,280,398 B2 5/2019 Studer
10,287,546 B2 5/2019 Chambers
10,711,243 B2 7/2020 Studer
10,828,335 B2 11/2020 George
10,858,625 B2 12/2020 Studer
11,236,302 B2 2/2022 Kirkeby
11,261,425 B2 3/2022 Takahashi
11,473,058 B2 10/2022 Takahashi
11,560,546 B2 1/2023 Chambers
12,013,388 B2 6/2024 Jungblut
2011/0118130 A1 5/2011 Loring
2014/0017212 A1 1/2014 Rebar
2015/0064139 A1 3/2015 Shoemaker
2015/0265652 A1 9/2015 George
2016/0201032 A1 7/2016 Studer
2016/0215260 A1* 7/2016 Takahashi ............... A61P 25/16
2017/0292112 A1 10/2017 Chang
(Continued)

FOREIGN PATENT DOCUMENTS

CA 3167713 7/2021
EP 3042951 7/2016
(Continued)

OTHER PUBLICATIONS

Deuse et al., "Hypoimmunogenic derivatives of induced pluripotent stem cells evade immune rejection in fully immunocompetent allogeneic recipients". Nat Biotechnol 37, 252-258 (2019). (Year: 2019).*
Borghese et al., "Inhibition of notch signaling in human embryonic stem cell-derived neural stem cells delays G1/S phase transition and accelerates neuronal differentiation in vitro and in vivo". Stem Cells. 2010, Abstract (Year: 2010).*
Vallier et al., "Signaling pathways controlling pluripotency and early cell fate decisions of human induced pluripotent stem cells," Stem Cells (2009) 27: 2655-2666.
Lavaute et al., "Regulation of Neural specification from human embryonic stem cells by BMP and FGF," Stem Cells (2009) 27: 1741-1749.
Patani et al., "Activin/Nodal inhibition alone accelerates highly efficient neural conversion from human embryonic stem cells and imposes a caudal positional identity," PlosOne (2009) 4:e7327.
(Continued)

*Primary Examiner* — Christopher M Babic
*Assistant Examiner* — Hanan Isam Abuzeineh
(74) *Attorney, Agent, or Firm* — Timothy L Smith

(57) ABSTRACT

The present disclosure provides methods of lineage specific differentiation of pluripotent stem cells, including induced pluripotent stem cells, into floor plate midbrain progenitor cells, determined dopamine (DA) neuron progenitor cells, and/or DA neurons. Also provided are compositions uses thereof, such as for treating neurodegenerative diseases and conditions, including Parkinson's disease.

29 Claims, 10 Drawing Sheets

(56) References Cited

U.S. PATENT DOCUMENTS

2018/0298326 A1 10/2018 Studer
2020/0338148 A1 10/2020 Abeliovich
2020/0407680 A1 12/2020 Studer
2021/0000929 A1 1/2021 Mason
2021/0123017 A1 4/2021 Ozaki
2021/0123018 A1 4/2021 Studer
2021/0292715 A1 9/2021 Schrepfer
2021/0393691 A1* 12/2021 Cooper .................. A61P 35/00
2022/0177835 A1 6/2022 Studer
2022/0186180 A1 6/2022 Studer
2022/0254448 A1 8/2022 Loring
2023/0081881 A1 3/2023 Bratt-Leal
2023/0165909 A1 6/2023 Zhang
2023/0233617 A1 7/2023 Ericson
2023/0340407 A1 10/2023 Yuejun

FOREIGN PATENT DOCUMENTS

EP 3042951 A1 * 7/2016 ............ A61K 35/30
EP 3061809 8/2016
EP 3447130 2/2019
WO 2008051604 5/2008
WO 2008132176 11/2008
WO 2010126614 11/2010
WO 2011019092 2/2011
WO 2011149762 12/2011
WO 2013015457 1/2013
WO 2013067362 5/2013
WO 2014200905 12/2014
WO 2015143342 9/2015
WO 2016162747 10/2016
WO 2017070633 4/2017
WO 2017132596 8/2017
WO 2017160234 9/2017
WO 2017222248 12/2017
WO 2019068854 4/2019
WO 2019111258 6/2019
WO 2019217943 11/2019
WO 2021016607 1/2021
WO 2021081229 4/2021
WO 2021087145 5/2021
WO 2021203009 10/2021
WO 2021216622 10/2021
WO 2021216623 10/2021
WO 2021216846 10/2021
WO 2021224496 11/2021
WO 2022062960 3/2022
WO 2022216911 10/2022
WO 2023004366 1/2023
WO 2023004370 1/2023
WO 2023004371 1/2023

OTHER PUBLICATIONS

Cuny et al., "Structure-activity relationship study of bone morphogenetic protein (BMP) signaling inhibitors," Bioorg & Medicinal Chemistry Letters (2008) 18: 4388-4392.
Hu et al., "Neural differentiation of human induced pluripotent stem cells follows developmental principles but with variable potency," Proc. Nat'l. Acad. Sci USA (2010) 9: 4335-4340.
Lamb et al., "Fibroblast growth factor is a direct neuronal inducer, which combined with noggin generates anterior-posterior neural pattern," Development (1995) 121: 3627-3636.
European Patent Office Decision to Grant dated Jun. 5, 2024.
European Patent Office Communication pursuant to Article 94(3) EPC dated Nov. 27, 2023.
International Preliminary Report on Patentability for PCT/US2021/013324, Aspen Neuroscience, Inc., filed Jan. 13, 2021, dated Jul. 19, 2022.
Arenas et al., "How to make a midbrain dopaminergic neuron," Development (2015) 142(11):1918-1936.
Arjona et al., "Autotransplantation of human carotid body cell aggregates for treatment of Parkinson's disease," Neurosurgery. (2003) 53(2):321-8.
Baden et al., "Insights into GBA Parkinson's disease pathology and therapy with induced pluripotent stem cell model systems," Neurobiol Dis. (2019), 127:1-12.
Badger et al., "Parkinson's disease in a dish—Using stem cells as a molecular tool," Neuropharmacology (2014) 76:88-96.
Bain et al., "Embryonic stem cells express neuronal properties in vitro," Dev Biol. (1995) 168(2):342-57.
Bakay et al., "Implantation of Spheramine in advanced Parkinson's disease (PD)," Front Biosci. (2004) 9:592-602.
Berge-Seidl et al., "The GBA variant E326K is associated with Parkinson's disease and explains a genome-wide association signal," Neuroscience Letters (2017) 658:48-52.
Bjorklund et al., "Neural transplantation for the treatment of Parkinson's disease," Lancet Neurol. (2003) 2 (7):437-45.
Brundin et al., "Neural grafting in Parkinson's disease Problems and possibilities," Prog Brain Res. (2010) 184:265-94.
Brunet et al., "Metagenes and molecular pattern discovery using matrix factorization," Proceedings of the National Academy of Sciences (2004) 101(12):4164-4169.
Cyranoski, "'Reprogrammed' stem cells implanted into patient with Parkinson's disease," Nature. (2018) doi: https://doi.org/10.1038/d41586-018-07407-9.
Deng et al., "The genetics of Parkinson disease," Ageing Research Reviews (2018) 42:72-85.
Doi et al., "Isolation of human induced pluripotent stem cell-derived dopaminergic progenitors by cell sorting for successful transplantation," Stem Cell Reports (2014) 2(3):337-50.
Fitzpatrick et al., "Cell-based therapies for Parkinson's disease: past, present, and future," Antioxid Redox Signal. (2009) 11(9):2189-2208.
Ghatak et al., "Parkinson's disease: what the model systems have taught US so far," Journal of Genetics (2018) 97 (3):729-751.
Han et al., "Generation of hypoimmunogenic human pluripotent stem cells," Proc Natl Acad Sci USA. (2019) 116 (21):10441-10446.
Hanss et al., "Quality Control Strategy for CRISPR-Cas9-Based Gene Editing Complicated by a Pseudogene," Frontiers in Genetics (2020) 10:1297.
Heijer et al., "A Large-Scale Full GBA1 Gene Screening in Parkinson's Disease in the Netherlands," Mov Disord. (2020) 35(9):1667-1674.
Kan et al., "Dopaminergic differentiation of human mesenchymal stem cells—utilization of bioassay for tyrosine hydroxylase expression," Neurosci Lett (2007) 419(1):28-33.
Kawaguchi et al., "Single-cell gene profiling defines differential progenitor subclasses in mammalian neurogenesis," Development (2008) 135(18):3113-24.
Kim et al., "miR-371-3 expression predicts neural differentiation propensity in human pluripotent stem cells," Cell Stem Cell (2011) 8(6):695-706.
Kirkeby et al., "Generation of Regionally Specified Neural Progenitors and Functional Neurons from Human Embryonic Stem Cells under Defined Conditions," Cell Reports (2012) 1(6):703-714.
Kordower et al., "Neuropathological evidence of graft survival and striatal reinnervation after the transplantation of fetal mesencephalic tissue in a patient with Parkinson's disease," N Engl J Med. (1995) 332(17):1118-24.
Kriks et al., "Floor plate-derived dopamine neurons from hESCs efficiently engraft in animal models of PD," Nature (2011) 480(7378):547-51.
Lee et al., "Efficient generation of midbrain and hindbrain neurons from mouse embryonic stem cells," Nat Biotechnol. (2000) 18(6):675-9.
Lehnen et al., "IAP-Based Cell Sorting Results in Homogeneous Transplantable Dopaminergic Precursor Cells Derived from Human Pluripotent Stem Cells," Stem Cell Reports (2017) 9(4):1207-1220.
Lindvall et al., "Stem cells in human neurodegenerative disorders—time for clinical translation?" J Clin Invest. (2010) 120(1):29-40.

(56) References Cited

OTHER PUBLICATIONS

Liu et al., "Genome wide profiling of human embryonic stem cells (hESCs), their derivatives and embryonal carcinoma cells to develop base profiles of U.S. Federal government approved hESC lines," BMC Dev Biol (2006) 6:20.
Madrazo et al., "Open microsurgical autograft of adrenal medulla to the right caudate nucleus in two patients with intractable Parkinson's disease," N Engl J Med. (1987) 316(14):831-4.
Martinez-Cerdeno et al., "Neural Progenitor Cell Terminology," Front Neuroanat (2018) 12:104.
Mendez et al., I., "Dopamine neurons implanted into people with Parkinson's disease survive without pathology for 14 years," Nat Med (2008) 14(5):507-509.
Muller et al., "Regulatory networks define phenotypic classes of human stem cell lines," Nature (2008) 455:401-405.
Ninkovic et al., "The transcription factor Pax6 regulates survival of dopaminergic olfactory bulb neurons via crystallin αA," Neuron (2010) 68(4):682-94.
Noisa et al., "Neural Progenitor Cells Derived from Human Embryonic Stem Cells as an Origin of Dopaminergic Neurons," Stem Cells Int (2015) 2015:647437.
Nowrousian et al., "Next-generation sequencing techniques for eukaryotic microorganisms: sequencing-based solutions to biological problems," Eukaryot Cell. (2010) 9(9):1300-10.
Ochalek et al., "Generation of Cholinergic and Dopaminergic Interneurons from Human Pluripotent Stem Cells as a Relevant Tool for In Vitro Modeling of Neurological Disorders Pathology and Therapy," Stem Cells Int. (2016) 5838934:1-16.
Okabe et al., "Development of neuronal precursor cells and functional postmitotic neurons from embryonic stem cells in vitro," Mech Dev. (1996) 59(1):89-102.
Okamoto et al., "Highly efficient genome editing for single-base substitutions using optimized ssODNs with Cas9-RNPs," Scientific Reports (2019) 9(1):1-11.
Paix et al, "Precision genome editing using CRISPR-Cas9 and linear repair templates in C. elegans," Methods (2017) 121-122:86-93.
Piccini et al., "Dopamine release from nigral transplants visualized in vivo in a Parkinson's patient," Nat Neurosci. (1999) 2(12):1137-40.
Raikwar et al., "Next generation precision medicine: CRISPR-mediated genome editing for the treatment of neurodegenerative disorders," Journal of Neuroimmune Pharmacology (2019) 14(4):608-641.
Reinhardt et al., "Genetic correction of a LRRK2 mutation in human iPSCs links parkinsonian neurodegeneration to ERK-dependent changes in gene expression," Cell Stem Cell (2013) 12(3):354-367.
Romito et al., "Pluripotent Stem Cells: Current Understanding and Future Directions," Stem Cells Int. (2016) 2016:9451492, 20 pages.
Sanders et al., "LRRK2 mutations cause mitochondrial DNA damage in iPSC-derived neural cells from Parkinson's disease patients: reversal by gene correction," Neurobiology of Disease (2014) 62:381-386.
Shendure et al., "Advanced sequencing technologies: methods and goals," Nat Rev Genet. (2004) 5(5):335-44.
Sison et al., "Using patient-derived induced pluripotent stem cells to identify Parkinson's disease-relevant phenotypes," Current Neurology and Neuroscience Reports (2018) 18(12):84, 1-14.
Smits et al., "Modeling Parkinson's disease in midbrain-like organoids," NPJ Parkinson's Disease (2019) 5(1):1-8.
Stepanichev, "Prospects for the Use of Genome-Editing Technology to Correct Neurodegenerative Diseases," Advances in Gerontology (2019) 9(2):154-163.
Tabar et al., "Therapeutic cloning in individual parkinsonian mice," Nat Med. (2008) 14(4):379-81.
Takahashi et al., "Induction of pluripotent stem cells from mouse embryonic and adult fibroblast cultures by defined factors," Cell (2006) 126(4):663-676.
Takahashi, "Strategies for bringing stem cell-derived dopamine neurons to the clinic: The Kyoto trial," Prog Brain Res. (2017) 230:213-226.
Tieng et al., "Engineering of midbrain organoids containing long-lived dopaminergic neurons," Stem Cells and Development (2014) 23(13):1535-1547.
Tsuji et al., "Genetic heterogeneity in type 1 Gaucher disease: multiple genotypes in Ashkenazic and non-Ashkenazic individuals," Proceedings of the National Academy of Sciences (1988) 85(7):2349-2352.
Vakulskas et al., "A high-fidelity Cas9 mutant delivered as a ribonucleoprotein complex enables efficient gene editing in human hematopoietic stem and progenitor cells," Nature Medicine (2018) 24(8):1216-1224.
Velez-Pardo et al., "The distribution and risk effect of GBA variants in a large cohort of PD patients from Colombia and Peru," Parkinsonism & Related Disorders (2019) 63:204-208.
Vetchinova et al., "Cytogenetic analysis of the results of genome editing on the cell model of Parkinson's disease," Bulletin of Experimental Biology and Medicine (2018) 165(3):378-381.
Kim et al., "Neural stem cells derived from human midbrain organoids as a stable source for treating Parkinson's disease Midbrain organoid-NSCs (Og-NSC) as a stable source for PD treatment," Progress in Neurobiology (2021) 204:102086.
Ye et al., "FGF and Shh signals control dopaminergic and serotonergic cell fate in the anterior neural plate," Cell. (1998) 93(5):755-66.
Yu et al., "Human induced pluripotent stem cells free of vector and transgene sequences," Science (2009) 324 (5928):797-801. DOI: 10.1126/science.1172482.
Kirkeby Agnete et al, "Predictive Markers Guide Differentiation to Improve Graft Outcome in Clinical Translation of hESC-Based Therapy for Parkinson's Disease", Cell Stem Cell, Amsterdam, NL, (Jan. 1, 2017), vol. 20, No. 1, doi:10.1016/j.stem.2016.09.004, ISSN 1934-5909, pp. 135-148, XP055974965.
Chambers et al., "Highly efficient neural conversion of human ES and iPS cells by dual inhibition of SMAD signaling," Nat Biotechnol (2009) 27(3):275-80.
Fasano et al. "Retraction Notice to: Efficient derivation of functional floor plate tissue from human embryonic stem cells," Cell Stem Cell (2023) 30(6): 905.
Fasano et al., "Efficient derivation of functional floor plate tissue from human embryonic stem cells," Cell Stem Cell (2010) 6(4):336-47.
Nolbrant et al.. "Generation of high-purity human ventral midbrain dopaminergic progenitors for in vitro maturation and intracerebral transplantation". Nature Protocols (2017) 12(9): 1962-1979.
Shimojo et al., "Rapid, efficient, and simple motor neuron differentiation from human pluripotent stem cells," Molecular Brain (2015) 8:79.
First Office Action for Chinese Patent Application No. 2021800206479 (English Translation).
Patent Search Report for Chinese Patent Application No. 2021800206479 (English Translation).
"Neural Stem Cells", Military Science Publishing House, published on Dec 31, 2006) (English translation).
Patent Search Report for Chinese Patent Application No. 2024116141573.
Rejection Decision for Chinese Patent Application No. 202411614157.3 (English translation).
First Office Action for Chinese Patent Application No. 202411614157.3 (English translation).

* cited by examiner

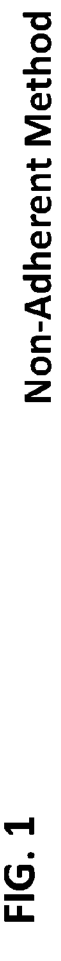
FIG. 1
Non-Adherent Method
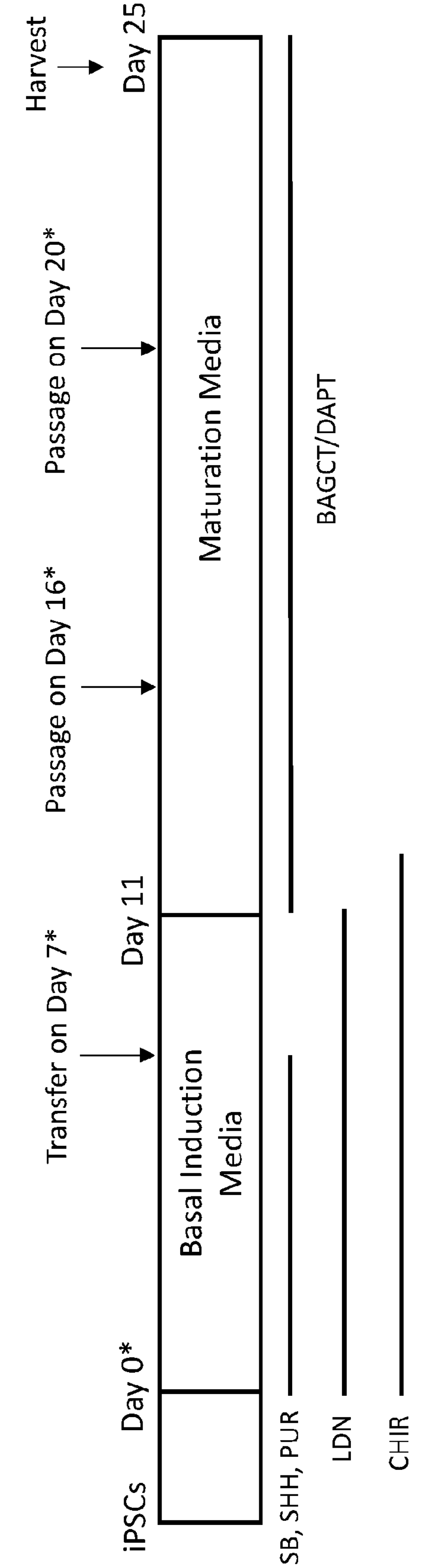
iPSCs
Day 0*
Transfer on Day 7*
Basal Induction Media
Day 11
Passage on Day 16*
Passage on Day 20*
Maturation Media
Harvest
Day 25
SB, SHH, PUR
LDN
CHIR
BAGCT/DAPT
*ROCKi included in medium on indicated day
BAGCT = BDNF, GDNF, ascorbic acid, dbcAMP, and TGFβ3

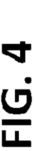
FIG. 4
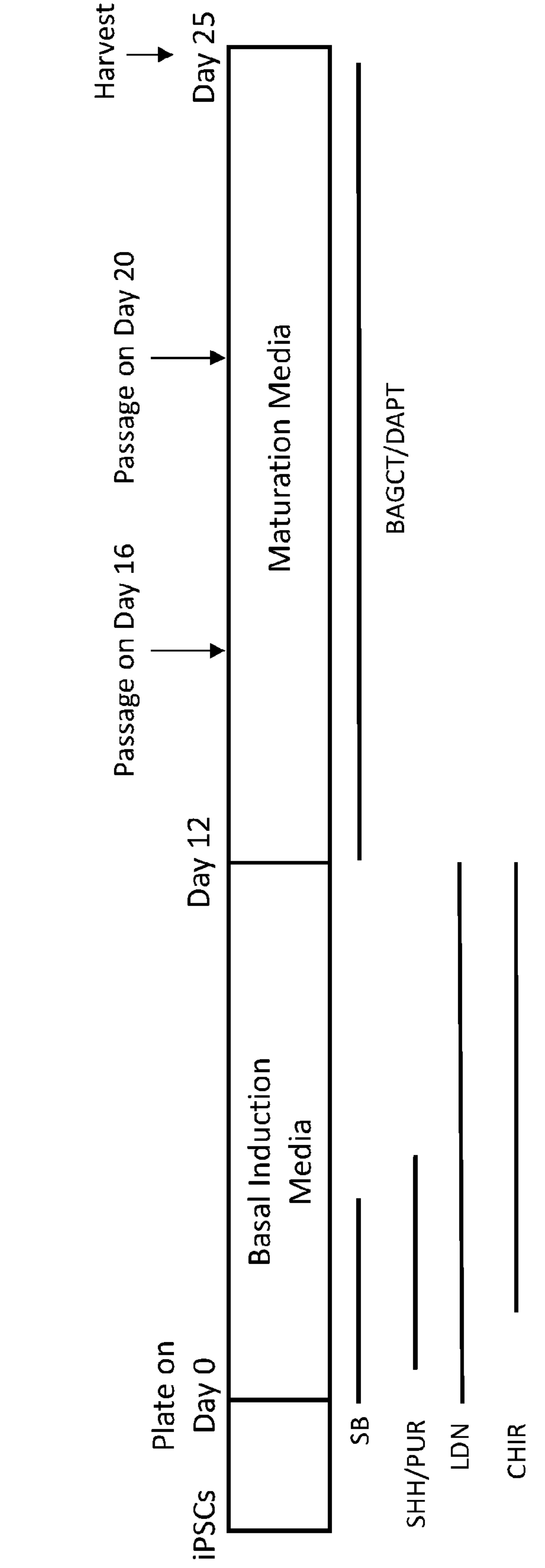
Adherent Method
iPSCs
Plate on Day 0
Day 12
Passage on Day 16
Passage on Day 20
Harvest
Day 25
Basal Induction Media
Maturation Media
SB
SHH/PUR
LDN
CHIR
BAGCT/DAPT
BAGCT = BDNF, GDNF, ascorbic acid, dbcAMP, and TGFβ3

FOXA2
Expression (vsd)
15
14
13
12
11
10
9
Day 0
Day 4
Day 7
Day 13
Day 18
Day 25
TH
Expression (vsd)
14
12
10
8
Day 0
Day 4
Day 7
Day 13
Day 18
Day 25

EN1
Expression (vsd)
12
11
10
9
8
7
Day 0
Day 4
Day 7
Day 13
Day 18
Day 25
CORIN
Expression (vsd)
18
16
14
12
10
Day 0
Day 4
Day 7
Day 13
Day 18
Day 25

PAX6
Expression (vsd)
16
14
12
10
Day 0
Day 4
Day 7
Day 13
Day 18
Day 25
SOX2
Expression (vsd)
14.5
14.0
13.5
13.0
12.5
12.0
Day 0
Day 4
Day 7
Day 13
Day 18
Day 25

METHODS OF DIFFERENTIATING NEURAL CELLS AND RELATED COMPOSITIONS AND METHODS OF USE

CROSS REFERENCE TO RELATED APPLICATIONS

This application is a national stage application under 35 U.S.C. § 371 of International Application No. PCT/US2021/013324, filed internationally on Jan. 13, 2021, which claims priority to U.S. provisional application 62/960,669, filed Jan. 13, 2020, entitled "METHOD OF DIFFERENTIATING NEURAL CELLS AND RELATED COMPOSITIONS AND METHODS OF USE," the contents of which are incorporated by reference in their entirety for all purposes.

FIELD

The present disclosure relates to methods of lineage specific differentiation of pluripotent stem cells, including induced pluripotent stem cells, into floor plate midbrain progenitor cells, determined dopamine (DA) neuron progenitor cells, and/or dopamine (DA) neurons. Also provided are compositions of the differentiated cells and therapeutic uses thereof, such as for treating neurodegenerative conditions and diseases, including Parkinson's disease.

BACKGROUND

Various methods for differentiating pluripotent stem cells into lineage specific cell populations and the resulting cellular compositions are contemplated to find use in cell replacement therapies for patients with diseases resulting in a loss of function of a defined cell population. However, in some cases, such methods are limited in their ability to produce cells with consistent physiological characteristics, and cells resulting from such methods may be limited in their ability to engraft and innervate other cells in vivo. Improved methods and cellular compositions thereof are needed, including to provide for improved methods for differentiating cells, such as to produce physiologically consistent cells.

SUMMARY

Provided herein is a method of differentiating neural cells, the method including: (a) performing a first incubation including culturing pluripotent stem cells in a non-adherent culture vessel under conditions to produce a cellular spheroid, wherein beginning at the initiation of the first incubation (day 0) the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3 beta (GSK3β) signaling; and (b) performing a second incubation including culturing cells of the spheroid in a substrate-coated culture vessel under conditions to neurally differentiate the cells. In some embodiments, the second incubation begins on about day 7.

In some embodiments, the cells are exposed to the inhibitor of TGF-β/activin-Nodal signaling up to a day at or before day 7. In some embodiments, the cells are exposed to the inhibitor of TGF-β/activin-Nodal signaling up to day 6. In some embodiments, the cells are exposed to the inhibitor of TGF-β/activin-Nodal beginning at day 0 and through day 6, inclusive of each day.

In some embodiments, the cells are exposed to the at least one activator of SHH signaling up to a day at or before day 7. In some embodiments, the cells are exposed to the at least one activator of SHH signaling up to day 6. In some embodiments, the cells are exposed to the at least one activator of SHH signaling beginning at day 0 and through day 6, inclusive of each day.

In some embodiments, the cells are exposed to the inhibitor of BMP signaling up to a day at or before day 11. In some embodiments, the cells are exposed to the inhibitor of BMP signaling up to day 10. In some embodiments, the cells are exposed to the inhibitor of BMP signaling beginning at day 0 and through day 10, inclusive of each day.

In some embodiments, the cells are exposed to the inhibitor of GSK3β signaling up to a day at or before day 13. In some embodiments, the cells are exposed to the inhibitor of GSK3β signaling up to day 12. In some embodiments, cells are exposed to the inhibitor of GSK3β signaling beginning at day 0 and through day 12, inclusive of each day.

In some embodiments, culturing the cells under conditions to neurally differentiate the cells in any of the provided methods includes exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3) (collectively, "BAGCT"); and (vi) an inhibitor of Notch signaling. In some embodiments, the cells are exposed to BAGCT and the inhibitor of Notch signaling beginning on day 11. In some embodiments, the cells are exposed to BAGCT and the inhibitor of Notch signaling beginning at day 11 and until harvest of the neurally differentiated cells. In some embodiments, the cells are exposed to BAGCT and the inhibitor of Notch signaling beginning at day 11 and until at or about day 18. In some embodiments, the cells are exposed to BAGCT and the inhibitor of Notch signaling beginning at day 11 and until at or about day 25.

Provided herein is a method of differentiating neural cells, the method including: (a) performing a first incubation including culturing pluripotent stem cells in a non-adherent culture vessel under conditions to produce a cellular spheroid, wherein beginning at the initiation of the first incubation day (day 0), the cells are exposed to (i) an inhibitor of TGF-β/activin-Nodal signaling through day 6, each day inclusive; (ii) at least one activator of Sonic Hedgehog (SHH) signaling through day 6, each day inclusive; (iii) an inhibitor of bone morphogenetic protein (BMP) signaling through day 6, each day inclusive; and (iv) an inhibitor of glycogen synthase kinase 3β (GSK3β) signaling through day 6, each day inclusive; and (b) beginning on day 7, performing a second incubation to neurally differentiate cells of the spheroid, including culturing the cells in a culture vessel coated with a substrate selected from among: laminin, collagen, entactin, heparin sulfate proteoglycans, and combinations thereof, wherein beginning on day 7, the cells are exposed to (i) an inhibitor of BMP signaling and (ii) an inhibitor of GSK3β signaling; and beginning on day 11, the cells are exposed to (i) brain-derived neurotrophic factor (BDNF); (ii) ascorbic acid; (iii) glial cell-derived neurotrophic factor (GDNF); (iv) dibutyryl cyclic AMP (db-cAMP); (v) transforming growth factor beta-3 (TGFβ3) (collectively, "BAGCT"); and (vi) an inhibitor of Notch signaling.

In some of any of the provided methods, the method further includes harvesting the neurally differentiated cells. In some embodiments, the harvesting is carried out at about day 16 or later. In some embodiments, the harvesting is carried out between about day 16 and about day 30. In some embodiments, the harvesting is carried out between about day 16 and about day 27. In some embodiments, the harvesting is carried out between day 18 and day 25. In some embodiments, the harvesting is carried out at or about at day 18. In some embodiments, the harvesting is carried out at or about at day 25.

In some embodiments, the neurally differentiated cells are determined dopaminergic neuron progenitor cells. In some embodiments, the dopaminergic progenitor cells are capable of innervating host tissue upon transplantation into a subject.

In some embodiments, prior to performing the second incubation, the spheroid is dissociated to produce a cell suspension and cells of the cell suspension are cultured in the substrate-coated culture vessel. In some embodiments, the dissociating is carried out at a time when the spheroid cells express at least one of PAX6 and OTX2. In some embodiments, the dissociating is carried out at a time when the spheroid cells express OTX2. In some embodiments, the dissociating is carried out at a time when the spheroid cells express PAX6. In some embodiments, the dissociating is carried out at a time when the spheroid cells express PAX6 and OTX2. In some embodiments, the dissociating is carried out on about day 7.

In some embodiments, the culture vessel is selected from among the group consisting of: a plate, a dish, a flask, and a bioreactor. In some embodiments, the culture vessel is a plate. In some embodiments, the plate is a 6-well plate, a 12-well plate, a 24-well plate, or a 96-well plate. In some embodiments, the plate is a microwell plate. In some embodiments, the microwell plate is a 6-well plate. In some embodiments, the microwell plate is a 24-well plate. In some embodiments, the culture vessel is an Aggre Well® plate.

In some embodiments, the culture vessel is treated to reduce or eliminate adherence of cells. In some embodiments, the culture vessel is treated to reduce adherence of cells. In some embodiments, the culture vessel is treated to eliminate adherence of cells. In some embodiments, treating the culture vessel includes incubating the culture vessel with pluronic acid. In some embodiments, prior to the first incubation, the non-adherent culture vessel is exposed to a surfactant. In some embodiments, the surfactant is pluronic acid.

In some embodiments, the non-adherent culture vessel has a low or ultra-low attachment surface. In some embodiments, the non-adherent culture vessel has a low attachment surface. In some embodiments, the non-adherent culture vessel has an ultra-low attachment surface. In some embodiments, the substrate is a basement membrane protein. In some embodiments, the substrate is selected from one or more of laminin, collagen, entactin, heparin sulfate proteoglycans, and combinations thereof. In some embodiments, the substrate is a recombinant protein. In some embodiments, the substrate is recombinant laminin. In some embodiments, the substrate-coated culture vessel is exposed to poly-L-ornithine prior to being used for culturing the cells.

In some embodiments, the inhibitor of TGF-β/activin-Nodal signaling is SB431542. In some embodiments, the cells are exposed to SB431542 at a concentration of between about 1 μM and about 20 μM, between about 5 μM and about 15 M, or between about 8 μM and about 12 μM. In some embodiments, the cells are exposed to SB431542 at a concentration of between about 1 μM and about 20 μM. In some embodiments, the cells are exposed to SB431542 at a concentration of between about 5 μM and about 15 μM. In some embodiments, the cells are exposed to SB431542 at a concentration of between about 8 μM and about 12 μM. In some embodiments, the cells are exposed to SB431542 at a concentration of about 10 μM.

In some embodiments, the at least one activator of SHH signaling is SHH protein or purmorphamine. In some embodiments, the at least one activator of SHH signaling is SHH protein. In some embodiments, the at least one activator of SHH signaling is purmorphamine. In some embodiments, the at least one activator of SHH signaling includes two activators of SHH signaling selected from SHH protein and purmorphamine. In some embodiments, the at least one activator of SHH signaling is two activators of SHH signaling selected from SHH protein and purmorphamine. In some embodiments, the cells are exposed to SHH at a concentration of between about 10 ng/mL and 500 ng/mL, between about 20 ng/ml and about 400 ng/ml, between about 50 ng/ml and about 200 ng/mL, or between about 75 ng/ml and about 150 ng/mL. In some embodiments, the cells are exposed to SHH at a concentration of between about 10 ng/mL and 500 ng/mL. In some embodiments, the cells are exposed to SHH at a concentration of between about 20 ng/ml and 400 ng/mL. In some embodiments, the cells are exposed to SHH at a concentration of between about 50 ng/ml and 200 ng/ml. In some embodiments, the cells are exposed to SHH at a concentration of between about 75 ng/mL and 150 ng/mL. In some embodiments, the cells are exposed to SHH at a concentration of about 100 ng/mL.

In some embodiments, the cells are exposed to purmorphamine at a concentration of between about 1 μM and about 20 μM, between about 5 M and about 15 μM, or between about 8 μM and about 12 μM. In some embodiments, the cells are exposed to purmorphamine at a concentration of between about 1 μM and about 20 μM. In some embodiments, the cells are exposed to purmorphamine at a concentration of between about 5 μM and about 15 μM. In some embodiments, the cells are exposed to purmorphamine at a concentration of between about 8 μM and about 12 μM. In some embodiments, the cells are exposed to purmorphamine at a concentration of about 10 μM.

In some embodiments, the cells are exposed to SHH at a concentration of about 100 ng/ml and purmorphamine at a concentration of about 10 μM.

In some embodiments, the inhibitor of BMP signaling is LDN193189. In some embodiments, the cells are exposed to LDN193189 at a concentration of between about 10 nM and 500 nM, between about 20 nM and about 400 nM, between about 50 nM and about 200 nM, or between about 75 nM and about 150 nM. In some embodiments, the cells are exposed to LDN193189 at a concentration of between about 10 nM and 500 nM. In some embodiments, the cells are exposed to LDN193189 at a concentration of between about 20 nM and 400 nM. In some embodiments, the cells are exposed to LDN193189 at a concentration of between about 50 nM and 200 nM. In some embodiments, the cells are exposed to LDN193189 at a concentration of between about 75 nM and 150 nM. In some embodiments, the cells are exposed to LDN193189 at a concentration of about 100 nM.

In some embodiments, the inhibitor of GSK3B signaling is CHIR99021. In some embodiments, the cells are exposed to CHIR99021 at a concentration of between about 0.1 μM and about 5 μM, between about 0.5 μM and about 4 μM, or between about 1 μM and about 3 μM. In some embodiments, the cells are exposed to CHIR99021 at a concentration of between about 0.1 μM and about 5 M. In some embodiments, the cells are exposed to CHIR99021 at a concentration of between about 0.5 μM and about 4 μM. In some embodiments, the cells are exposed to CHIR99021 at a concentration of between about 1 μM and about 3 μM. In some embodiments, the cells are exposed to CHIR99021 at a concentration of about 2 μM.

In some embodiments, the cells are exposed to GDNF at a concentration of between about 1 ng/mL and about 100 ng/mL, between about 5 ng/ml and about 80 ng/ml, between about 10 ng/ml and about 60 ng/mL, or between about 15 ng/mL and about 30 ng/ml. In some embodiments, the cells are exposed to GDNF at a concentration of between about 1 ng/ml and about 100 ng/mL. In some embodiments, the cells are exposed to GDNF at a concentration of between about 5 ng/mL and about 80 ng/mL. In some embodiments, the cells are exposed to GDNF at a concentration of between about 10 ng/ml and about 60 ng/mL. In some embodiments, the cells are exposed to GDNF at a concentration of between about 15 ng/mL and about 30 ng/mL. In some embodiments, the cells are exposed to GDNF at a concentration of about 20 ng/mL.

In some embodiments the cells are exposed to BDNF at a concentration of between about 1 ng/mL and about 100 ng/mL, between about 5 ng/mL and about 80 ng/ml, between about 10 ng/ml and about 60 ng/mL, or between about 15 ng/mL and about 30 ng/mL. In some embodiments the cells are exposed to BDNF at a concentration of between about 1 ng/ml and about 100 ng/mL. In some embodiments the cells are exposed to BDNF at a concentration of between about 5 ng/mL and about 80 ng/mL. In some embodiments the cells are exposed to BDNF at a concentration of between about 10 ng/ml and about 60 ng/ml. In some embodiments the cells are exposed to BDNF at a concentration of between about 15 ng/mL and about 30 ng/mL. In some embodiments the cells are exposed to BDNF at a concentration of about 20 ng/mL.

In some embodiments, the cells are exposed to dbcAMP at a concentration of between about 0.1 mM and 5 mM, between about 0.2 mM and about 4 mM, between about 0.3 mM and about 3 mM, or between about 0.4 mM and about 2 mM. In some embodiments, the cells are exposed to dbcAMP at a concentration of between about 0.1 mM and 5 mM. In some embodiments, the cells are exposed to dbcAMP at a concentration of between about 0.2 mM and 4 mM. In some embodiments, the cells are exposed to dbcAMP at a concentration of between about 0.3 mM and 3 mM. In some embodiments, the cells are exposed to dbcAMP at a concentration of between about 0.4 mM and 2 mM. In some embodiments, the cells are exposed to dbcAMP at a concentration of about 0.5 mM.

In some embodiments, the cells are exposed to ascorbic at a concentration of between about 0.05 mM and about 5 mM, between about 0.1 mM and about 1 mM, or between about 0.2 mM and about 0.5 mM. In some embodiments, the cells are exposed to ascorbic at a concentration of between about 0.05 mM and about 5 mM. In some embodiments, the cells are exposed to ascorbic at a concentration of between about 0.1 mM and about 2 mM. In some embodiments, the cells are exposed to ascorbic at a concentration of between about 0.2 mM and about 0.5 mM. In some embodiments, the cells are exposed to ascorbic at a concentration of about 0.2 mM.

In some embodiments, the cells are exposed to TGFβ3 at a concentration of between about 0.1 ng/ml and about 5 ng/mL, between about 0.3 ng/ml and about 3 ng/mL, or between about 0.5 ng/mL and about 2 ng/mL. In some embodiments, the cells are exposed to TGFβ3 at a concentration of between about 0.1 ng/ml and about 5 ng/ml. In some embodiments, the cells are exposed to TGFβ3 at a concentration of between about 0.3 ng/ml and about 3 ng/mL. In some embodiments, the cells are exposed to TGFβ3 at a concentration of between about 0.5 ng/mL and about 2 ng/mL. In some embodiments, the cells are exposed to TGFβ3 at a concentration of about 1 ng/mL.

In some embodiments, the inhibitor of Notch signaling is DAPT. In some embodiments, the cells are exposed to DAPT at a concentration of between about 1 μM and about 20 μM, between about 5 μM and about 15 μM, or between about 8 UM and about 12 μM. In some embodiments, the cells are exposed to DAPT at a concentration of between about 1 μM and about 20 μM. In some embodiments, the cells are exposed to DAPT at a concentration of between about 5 μM and about 15 μM. In some embodiments, the cells are exposed to DAPT at a concentration of between about 8 μM and about 12 μM. In some embodiments, the cells are exposed to DAPT at a concentration of about 10 μM.

In some of any of the provided embodiments, the culturing in the first incubation and/or the second incubation is carried out in media having serum or a serum replacement. In some of any of the provided embodiments, the culturing in the first incubation is carried out in media having serum or a serum replacement. In some of any of the provided embodiments, the culturing in the second incubation is carried out in media having serum or a serum replacement. In some embodiments, the culturing in the first incubation and the second incubation is carried out in media having serum or a serum replacement. In some embodiments, the cells are cultured in a media having serum or a serum replacement from day about 0 to about day 10. In some embodiments, the serum or serum replacement constitutes about 5% of the media (v/v). In some embodiments, the serum or serum replacement constitutes about 2% of the media (v/v). In some embodiments, the media includes about 5% serum or serum replacement (v/v) from about day 0 to about day 1 and about 2% serum replacement (v/v) from about day 2 to about day 10. In some embodiments, the media contains a serum replacement. In some embodiments, the serum replacement does not contain fetal bovine serum (FBS). In some embodiments, the serum replacement is KnockOut® serum replacement.

In some embodiments, the cells are cultured in the absence of serum for the duration of culture.

In some embodiments, the cells are exposed to an inhibitor of Rho-associated protein kinase (ROCK) signaling during one or more days of the first and second incubation. In some embodiments, the inhibitor of ROCK signaling is added at least once a week during the course of the method. In some embodiments, the cells are exposed to an inhibitor of ROCK signaling on day 0, day 7, day 16, and/or day 20. In some embodiments, the cells are exposed to an inhibitor of Rho-associated protein kinase (ROCK) signaling on day 0. In some embodiments, the cells are exposed to an inhibitor of Rho-associated protein kinase (ROCK) signaling on day 7. In some embodiments, the cells are exposed to an inhibitor of Rho-associated protein kinase (ROCK) signaling on day 16. In some embodiments, the cells are exposed to an inhibitor of Rho-associated protein kinase (ROCK) signaling on day 20. In some embodiments, the cells are exposed to an inhibitor of Rho-associated kinase protein (ROCK) signaling on days 0, 7, 16, and 20. In some embodiments, the ROCK inhibitor is Y-27632. In some embodiments, the cells are exposed to the ROCK inhibitor at a concentration of between about 1 μM and about 20 μM, between about 5 μM and about 15 μM, or between about 8 μM and about 12 μM. In some embodiments, the cells are exposed to the ROCK inhibitor at a concentration of between about 1 μM and about 20 μM. In some embodiments, the cells are exposed to the ROCK inhibitor at a concentration of between about 5 μM and about 15 μM. In some embodiments, the cells are exposed to the ROCK inhibitor at a concentration of between about 8 μM and about 12 μM. In some embodiments, the cells are exposed to the ROCK inhibitor at a concentration of about 10 μM.

In some embodiments, at least about 50% of the media is replaced daily or every other day, or every third day during the culturing of the first and/or second incubation. In some embodiments, at least about 50% of the media is replaced daily. In some embodiments, at least about 50% of the media is replaced every other day. In some embodiments, at least about 50% of the media is replaced every third day. In some embodiments, at least about 50% of the media is replaced daily during the first incubation. In some embodiments, at least about 50% of the media is replaced every other day during the first incubation. In some embodiments, at least about 50% of the media is replaced every third day during the first incubation. In some embodiments, at least about 50% of the media is replaced daily during the second incubation. In some embodiments, at least about 50% of the media is replaced every other day during the second incubation. In some embodiments, at least about 50% of the media is replaced every third day during the second incubation. In some embodiments, at least about 50% of the media is replaced daily during the first incubation and the second incubation. In some embodiments, at least about 50% of the media is replaced every other day during the first incubation and the second incubation. In some embodiments, at least about 50% of the media is replaced every third day during the first incubation and the second incubation.

In some embodiments, the method includes dissociation of the spheroid prior to the second incubation. In some embodiments, the spheroid is dissociated by enzymatic dissociation. In some embodiments, the method includes dissociation of the spheroid prior to the second incubation and the spheroid is dissociated by enzymatic dissociation. In some embodiments, the spheroid is dissociated by enzymatic dissociation including use of an enzyme selected from Accutase®, Dispase®, collagenase, or a combination thereof. In some embodiments, the spheroid is dissociated by enzymatic dissociation including use of Accutase®. In some embodiments, the spheroid is dissociated by Accutase®.

In some embodiments, after the dissociation of the spheroid, cells of the dissociated spheroid are cultured on the substrate-coated culture vessel, such as by transferring the cells to the substrate-coated culture vessel. In some embodiments, after the dissociation of the spheroid, cells of the dissociated spheroid are cultured on the substrate-coated culture vessel. In some embodiments, after the dissociation of the spheroid, cells of the dissociated spheroid are cultured on the substrate-coated culture vessel, such as by transferring the cells to the substrate-coated culture vessel, at a concentration between about $0.4\times10^6$ cells/$cm^2$ and about $0.8\times10^6$ cells/$cm^2$. In some embodiments, transferring cells of the dissociated spheroid to the substrate-coated vessel occurs on about day 7.

In some embodiments, cells of the spheroid from the first incubation are not dissociated prior to transferring the spheroid cells to a substrate-coated culture vessel. In some embodiments, the second incubation includes culturing cells of the spheroid from the first incubation without first dissociating the cells to form a cell suspension.

In some of any of the provided embodiments, the method further includes formulating the harvested cells with a cryoprotectant. In some embodiments, the cryoprotectant is selected from glycerol, propylene glycol, dimethyl sulfoxide (DMSO), or a combination thereof. In some embodiments, the cryoprotectant includes DMSO. In some embodiments, the cryoprotectant is DMSO. In some embodiments, the harvested cells are formulated with about 10% DMSO.

In some embodiments, the pluripotent stem cells are embryonic stem (ES) cells, induced pluripotent stem cells (iPSCs), or a combination thereof. In some embodiments, the pluripotent stem cells are embryonic stem (ES) cells. In some embodiments, the pluripotent stem cells are induced pluripotent stem cells (iPSCs). In some embodiments, the pluripotent stem cells are embryonic stem (ES) cells. In some embodiments, the ES cells are mouse or human embryonic stem cells. In some embodiments, the ES cells are mouse embryonic stem cells. In some embodiments, the pluripotent stem cells are human embryonic stem cells. In some embodiments, the pluripotent stem cells are induced pluripotent stem cells. In some embodiments, the iPSCs are mouse or human induced pluripotent stem cells. In some embodiments, the pluripotent stem cells are mouse induced pluripotent stem cells. In some embodiments, the pluripotent stem cells are human induced pluripotent stem cells.

In some embodiments, the pluripotent stem cells are autologous to a subject to be treated with the neurally differentiated cells. In some embodiments, the subject to be treated has Parkinson's Disease. In some embodiments, the subject to be treated is suspected of having Parkinson's Disease. In some embodiments, the subject to be treated has Parkinsonism. In some embodiments, the subject to be treated is suspected of having Parkinsonism.

In some embodiments, the pluripotent stem cells are allogeneic to a subject to be treated with the neurally differentiated cells. In some embodiments, the neurally differentiated cells are hypoimmunogenic. In some embodiments, the pluripotent stem cells are engineered to (a) remove genes encoding one or more of polymorphic HLA-A/-B/-C and HLA class II molecules; and (b) to provide genes encoding one or more of PD-L1, HLA-G, and CD47. In some embodiments, the pluripotent stem cells are engineered to remove genes encoding the polymorphic HLA-A/-B/-C and HLA class II molecules. In some embodiments, the pluripotent stem cells are engineered to provide genes encoding PD-L1, HLA-G, and CD47. In some embodiments, the pluripotent stem cells are engineered to provide genes encoding PD-L1, HLA-G, and CD47 into a AAVS1 safe harbor locus. In some embodiments, the pluripotent stem cells are engineered to remove genes encoding the polymorphic HLA-A/-B/-C and HLA class II molecules and to provide genes encoding PD-L1, HLA-G, and CD47 into a AAVS1 safe harbor locus Also provided herein is a therapeutic composition produced by any of the provided methods.

In some embodiments, cells of the therapeutic composition express EN1 and/or CORIN. In some embodiments, cells of the therapeutic composition express EN1. In some embodiments, cells of the therapeutic composition express CORIN. In some embodiments, cells of the therapeutic composition express EN1 and CORIN. In some embodiments, cells of the composition express EN1 and CORIN and less than 10% of the total cells in the composition express TH.

Also provided herein is a therapeutic composition containing determined dopamine neuron progenitor cells (DDPCs) derived from pluripotent stem cells, wherein cells in the composition express EN1 and CORIN and less than 10% of the total cells in the composition express TH.

Also provided herein is a therapeutic composition containing determined dopamine neuron progenitor cells (DDPCs) derived from pluripotent stem cells, wherein the therapeutic composition exhibits a ratio of counts per million (CPM) TH to CPM GAPDH of less than about $2.5\times10^{-2}$.

In some embodiments, less than 3%, 2%, 1%, or 0.5% of the total cells in the therapeutic composition are serotonergic cells. In some embodiments, less than 1% of the total cells in the therapeutic composition are serotonergic cells. In some embodiments, less than 0.5% of the total cells in the therapeutic composition are serotonergic cells.

In some embodiments, less than 1%, 0.5%, 0.25%, or 0.05% of the total cells in the therapeutic composition are pluripotent stem cells. In some embodiments, less than 0.5% of the total cells in the therapeutic composition are pluripotent stem cells. In some embodiments, less than 0.05% of the total cells in the therapeutic composition are pluripotent cells.

In some embodiments, at least about 70%, 75%, 80%, 85%, 90%, or 95% of the total cells in the therapeutic composition are viable. In some embodiments, at least about 70% of the total cells in the therapeutic composition are viable. In some embodiments, at least about 75% of the total cells in the therapeutic composition are viable. In some embodiments, at least about 80% of the total cells in the therapeutic composition are viable. In some embodiments, at least about 85% of the total cells in the therapeutic composition are viable. In some embodiments, at least about 90% of the total cells in the therapeutic composition are viable. In some embodiments, at least about 95% of the total cells in the therapeutic composition are viable.

In some embodiments, the determined cells are capable of engrafting and innervating other cells in vivo.

In some embodiments, the therapeutic composition includes a cryoprotectant. In some embodiments, the cryoprotectant is glycerol, propylene glycol, dimethyl sulfoxide (DMSO), or a combination thereof. In some embodiments, the cryoprotectant is DMSO. In some embodiments, the therapeutic composition includes about 10% DMSO.

In some embodiments, the composition is for use in treatment of a neurodegenerative disease or condition in a subject. In some embodiments, the neurodegenerative disease or condition includes a loss of dopaminergic neurons. In some embodiments, the neurodegenerative disease or condition includes a loss of dopaminergic neurons in the substantia nigra (SN). In some embodiments, the neurodegenerative disease or condition includes a loss of dopaminergic neurons in the SN pars compacta (SNc). In some embodiments, the neurodegenerative disease or condition is Parkinson's disease. In some embodiments, the neurodegenerative disease or condition is Parkinsonism.

Also provided herein is a method of treatment, including administering to a subject a therapeutically effective amount of any of the therapeutic compositions provided herein.

In some embodiments, the subject has a neurodegenerative disease or condition. In some embodiments, the neurodegenerative disease or condition includes the loss of dopaminergic neurons. In some embodiments, the subject has lost at least 50% of dopaminergic neurons. In some embodiments, the subject has lost at least 50% of dopaminergic neurons in the substantia nigra (SN). In some embodiments, the subject has lost at least 50% of dopaminergic neurons in the SN pars compacta (SNc). In some embodiments, the neurodegenerative disease or condition is Parkinsonism. In some embodiments, the neurodegenerative disease or condition is Parkinson's disease. In some embodiments, the neurodegenerative disease or condition is idiopathic Parkinson's disease.

In some embodiments, the administering includes delivering cells of a composition by stereotactic injection. In some embodiments, the administering includes delivering cells of a composition through a catheter. In some embodiments, the cells are delivered to the striatum of the subject. In some embodiments, the subject is administered between about $3\times10^6$ cells/hemisphere and $15\times10^6$ cells/hemisphere.

In some embodiments, the cells of the therapeutic composition are autologous to the subject.

In some embodiments, the cells of the therapeutic composition are allogeneic to the subject. In some embodiments, the cells of the therapeutic composition are hypoimmunogenic. In some embodiments, the cells of the therapeutic composition are engineered to (a) remove genes encoding one or more of polymorphic HLA-A/-B/-C and HLA class II molecules; and (b) to provide genes encoding one or more of PD-L1, HLA-G, and CD47. In some embodiments, the cells of the therapeutic composition are engineered to remove genes encoding the polymorphic HLA-A/-B/-C and HLA class II molecules. In some embodiments, the cells of the therapeutic composition are engineered to provide genes encoding PD-L1, HLA-G, and CD47. In some embodiments, the cells of the therapeutic composition are engineered to provide genes encoding PD-L1, HLA-G, and CD47 into an AAVS1 safe harbor locus. In some embodiments, the cells of the therapeutic composition are engineered to remove genes encoding the polymorphic HLA-A/-B/-C and HLA class II molecules and provide genes encoding PD-L1, HLA-G, and CD47 into a AAVS1 safe harbor locus.

Also provided herein is a use of any of the compositions provided herein, for the treatment of Parkinsonism. Also provided herein is a use of any of the compositions provided herein, for the treatment of Parkinson's disease.

Also provided herein is a composition as described herein for formulation of a medicament for treating a subject having a neurodegenerative disease or condition.

Also provided herein is a pharmaceutical composition of any as described herein for use in treating a subject having a neurodegenerative disease or condition.

In some embodiments, the neurodegenerative disease or condition includes the loss of dopaminergic neurons. In some embodiments, the subject has lost at least 50%, at least 60%, at least 70%, or at least 80% of dopaminergic neurons, optionally in the substantia nigra (SN), optionally in the SN pars compacta (SNc). In some embodiments, the neurodegenerative disease or condition is Parkinsonism. In some embodiments, the neurodegenerative disease or condition is Parkinson's disease, optionally idiopathic Parkinson's disease.

In some embodiments, the cells of the composition are autologous to the subject. In some embodiments, the cells of the composition are allogeneic to the subject. In some embodiments, the cells of the therapeutic composition are hypoimmunogenic. In some embodiments, the cells of the therapeutic composition are engineered to (a) remove genes encoding one or more of polymorphic HLA-A/-B/-C and HLA class II molecules; and (b) to provide genes encoding one or more of PD-L1, HLA-G, and CD47, optionally into a AAVS1 safe harbor locus.

BRIEF DESCRIPTION OF THE DRAWINGS

FIG. 1. shows an exemplary non-adherent protocol for the differentiation of pluripotent stem cells into determined dopamine (DA) neuron progenitor cells or DA neurons.

FIG. 4 shows an exemplary adherent protocol for the differentiation of pluripotent stem cells into determined dopamine (DA) neuron progenitor cells or DA neurons.

I. DEFINITIONS

Figure 2:
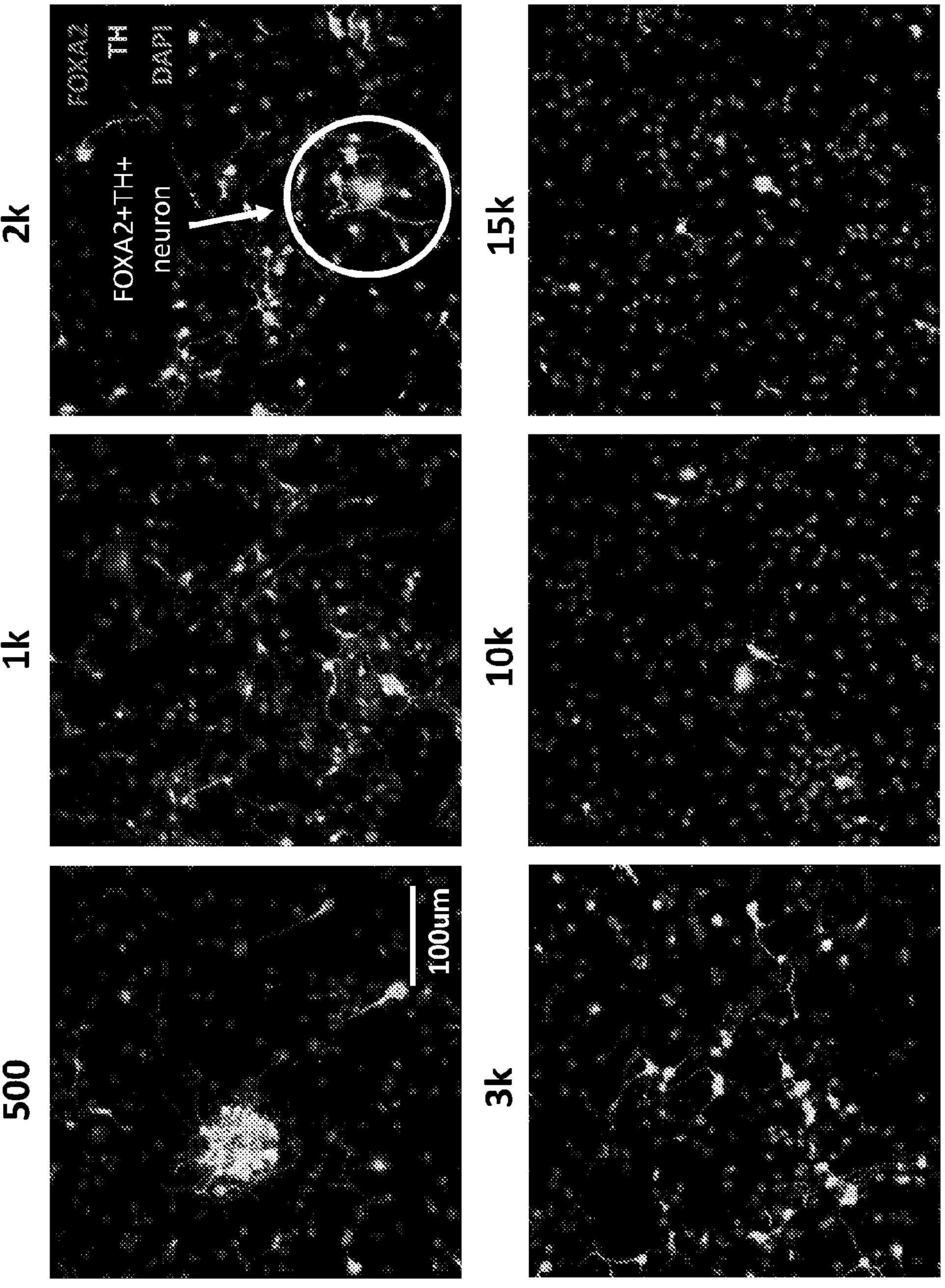
FIG. 2 shows FOXA2, TH, and DAPI expression by differentiated cells at day 25, derived from spheroids having approximately 500, 1,000, 2,000, 3,000, 10,000, or 15,000 cells.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X".

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker. When referring to a marker in the cell, such as a transcriptional or translational product, the term refers to the presence of detectable transcriptional or translational product, for example, wherein the product is detected at a level substantially above the level detected carrying out the same procedure with a control under otherwise identical conditions and/or at a level substantially similar to that for a cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker. When referring to a marker in the cell, such as a transcriptional or translational product, the term refers to the absence of detectable transcriptional or translational product, for example, wherein the product is not detected at a level substantially above the level detected carrying out the same procedure with a control under otherwise identical conditions, and/or at a level substantially lower than that for cell known to be positive for the marker, and/or at a level substantially similar as compared to that for a cell known to be negative for the marker.

The term "expression" or "expressed" as used herein in reference to a gene refers to the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, *Molecular Cloning: A Laboratory Manual,* 18.1-18.88).

As used herein, the term "stem cell" refers to a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

As used herein, the term "adult stem cell" refers to an undifferentiated cell found in an individual after embryonic development. Adult stem cells multiply by cell division to replenish dying cells and regenerate damaged tissue. An adult stem cell has the ability to divide and create another cell like itself or to create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers.

As used herein, the terms "induced pluripotent stem cell," "iPS" and "iPSC" refer to a pluripotent stem cell artificially derived (e.g., through man-made manipulation) from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells.

As used herein, the term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism.

As used herein, the term "pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

As used herein, the term "reprogramming" refers to the process of dedifferentiating a non-pluripotent cell into a cell exhibiting pluripotent stem cell characteristics.

As used herein, the term "adherent culture vessel" refers to a culture vessel to which a cell may attach via extracellular matrix molecules and the like, and requires the use of an enzyme (e.g., trypsin, Dispase®, etc.) for detaching cells from the culture vessel. An "adherent culture vessel" is opposed to a culture vessel to which cell attachment is reduced and does not require the use of an enzyme for removing cells from the culture vessel.

As used herein, the term "non-adherent culture vessel" refers to a culture vessel to which cell attachment is reduced or limited, such as for a period of time. A non-adherent culture vessel may contain a low attachment or ultra-low attachment surface, such as may be accomplished by treating the surface with a substance to prevent cell attachment, such as a hydrogel (e.g., a neutrally charged and/or hydrophilic hydrogel) and/or a surfactant (e.g. pluronic acid). A non-adherent culture vessel may contain rounded or concave wells, and/or microwells (e.g., AggreWell®). In some embodiments, a non-adherent culture vessel is an Aggre Well® plate. For non-adherent culture vessels, use of an enzyme to remove cells from the culture vessel may not be required.

As used herein, the term "cell culture" may refer to an in vitro population of cells residing outside of an organism. The cell culture can be established from primary cells isolated from a cell bank or animal, or secondary cells that are derived from one of these sources and immortalized for long-term in vitro cultures.

As used herein, the terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division.

As used herein, a composition refers to any mixture of two or more products, substances, or compounds, including cells. It may be a solution, a suspension, liquid, powder, a paste, aqueous, non-aqueous or any combination thereof.

The term "pharmaceutical composition" refers to a composition suitable for pharmaceutical use, such as in a mammalian subject (e.g., a human). A pharmaceutical composition typically comprises an effective amount of an active agent (e.g., cells) and a carrier, excipient, or diluent. The carrier, excipient, or diluent is typically a pharmaceutically acceptable carrier, excipient or diluent, respectively.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, a "subject" is a mammal, such as a human or other animal, and typically is human.

DETAILED DESCRIPTION

The present disclosure relates to methods of lineage specific differentiation of pluripotent stem cells (PSCs), such as embryonic stem (ES) cells or induced pluripotent stem cells (iPSCs). Specifically described are methods of directing lineage specific differentiation of PSCs or iPSCs into floor plate midbrain progenitor cells, determined dopamine (DA) neuron progenitor cells (DDPCs), and/or dopamine (DA) neurons. The differentiated cells made using the methods provided herein are further contemplated for various uses including, but not limited to, use as a therapeutic to reverse disease of, or damage to, a lack of dopamine neurons in a patient.

Provided herein are methods for lineage specific differentiation of pluripotent stem cells (PSCs), such as embryonic stem (ES) cells or induced pluripotent stem cells (iPSCs) into floor plate midbrain progenitor cells, determined dopamine (DA) neuron progenitor cells, and/or dopamine (DA) neurons. In some aspects, PSCs are differentiated into floor plate midbrain progenitor cells. In some aspects, such floor plate midbrain progenitor cells are further differentiated into determined dopamine (DA) neuron progenitor cells. In some embodiments, determined dopaminergic precursor cells are cells that differentiate into dopamine neurons and cannot differentiate into non-dopamine neuron cells. In some aspects, such determined dopamine (DA) neuron progenitor cells are further differentiated into dopamine (DA) neurons. In some aspects, PSCs are differentiated into floor plate midbrain progenitor cells, then into determined dopamine (DA) neuron progenitor cells, and finally, into dopamine (DA) neurons.

The provided embodiments address problems related to characteristics of Parkinson's disease (PD) including the selective degeneration of midbrain dopamine (mDA) neurons in patients' brains. Because PD symptoms are primarily due to the selective loss of DA neurons in the substantia nigra of the ventral midbrain, PD is considered suitable for cell replacement therapeutic strategies.

A challenge in developing a cell based therapy for PD has been the identification of an appropriate cell source for use in neuronal replacement. The search for an appropriate cell source is decades-long, and many potential sources for DA neuron replacement have been proposed. Kriks, *Protocols for generating ES cell-derived dopamine neurons in Development and engineering of dopamine neurons* (eds. Pasterkamp, R. J., Smidt, & Burbach) Landes Biosciences (2008); Fitzpatrick, et al., *Antioxid. Redox. Signal*. (2009) 11:2189-2208. Several of these sources progressed to early stage clinical trials including catecholaminergic cells from the adrenal medulla, carotid body transplants, or encapsulated retinal pigment epithelial cells. Madrazo, et al., *N. Engl. J. Med*. (1987) 316:831-34; Arjona, et al., *Neurosurgery* (2003) 53:321-28; Spheramine trial Bakay, et al., *Front Biosci*. (2004) 9:592-602. However, those trials largely failed to show clinical efficacy and resulted in poor long-term survival and low DA release from the grafted cells.

Another approach was the transplantation of fetal midbrain DA neurons, such as was performed in over 300 patients worldwide. Brundin, et al., *Prog. Brain Res*. (2010) 184:265-94; Lindvall, & Kokaia, *J. Clin. Invest* (2010) 120:29-40. Therapy using human fetal tissue in these patients demonstrated evidence of DA neuron survival and in vivo DA release up to 10 or 20 years after transplantation in some patients. In many patients, though, fetal tissue transplantation fails to replace DA neuronal function. Further, fetal tissue transplantation is plagued by challenges including low quantity and quality of donor tissue, ethical and practical issues surrounding tissue acquisition, and the poorly defined heterogeneous nature of transplanted cells, which are some of the factors contributing to the variable clinical outcomes. Mendez, et al., *Nature Med*. (2008); Kordower, et al., *N. Engl. J. Med*. (1995) 332:1118-24; and Piccini, et al., *Nature Neuroscience* (1999) 2:1137-40. Hypotheses as to the limited efficacy observed in the human fetal grafting trials include that fetal grafting may not provide a sufficient number of cells at the correct developmental stage and that fetal tissue is quite poorly defined by cell type and variable with regard to the stage and quality of each tissue sample. Bjorklund, et al., *Lancet Neurol*. (2003) 2:437-45. A further contributing factor may be inflammatory host response to the graft. Id.

Stem cell-derived cells, such as pluripotent stem cells (PSCs), are contemplated as a source of cells for applications in regenerative medicine. Pluripotent stem cells have the ability to undergo self-renewal and give rise to all cells of the issues of the body. PSCs include two broad categories of cells: embryonic stem (ES) cells and induced pluripotent stem cells (iPSCs). ES cells are derived from the inner cell mass of preimplantation embryos and can be maintained indefinitely and expanded in their pluripotent state in vitro. Romito and Cobellis, *Stem Cells Int*. (2016) 2016:9451492. iPSCs can be obtained by reprogramming ("dedifferentiating") adult somatic cells to become more ES cell-like, including having the ability to expand indefinitely and differentiate into all three germ layers. Id.

Pluripotent stem cells such as ES cells have been tested as sources for generating engraftable cells. Early studies in the 1990s using mouse ES cells demonstrated the feasibility of deriving specific lineages from pluripotent cells in vitro, including neurons. Okabe, et al., *Mech. Dev*. (1996) 59:89-102; Bain, et al., *Dev. Biol*. (1995) 168v342-357. Midbrain DA neurons were generated using a directed differentiation strategy based on developmental insights from early explants studies. Lee, et al., *Nat. Biotechnol*. (2000) 18v675-679; Ye, et al., *Cell* (1998) 93:755-66. However, these efforts did not result in cell populations containing high percentages of midbrain DA neurons or cells capable of restoring neuronal function in vivo. Additionally, the resulting populations contained a mixture of cell types in addition to midbrain DA neurons.

Existing strategies for using human PSCs (hPSCs) for cell therapy have not been entirely satisfactory. DA neurons derived from human PSCs generally have displayed poor in vivo performance, failing to compensate for the endogenous loss of neuronal function. Tabar, et al., *Nature Med*. (2008) 14:379-81; Lindvall and Kokaia, *J. Clin. Invest* (2010) 120:29-40.

More recently, preclinical studies in which human ES cells were first differentiated into midbrain floor intermediates, and then further into DA neurons, exhibited in vivo survival and led to motor deficit recovery in animal models. Kriks et al., *Nature* (2011) 480:547-51; Kirkeby et al., *Cell Rep*. (2012) 1:703-14. Despite these advances, the use of embryonic stem cells is plagued by ethical concerns, as well as the possibility that such cells may form tumors in patients. Finally, ES cell-derived transplants may cause immune reactions in patients in the context of allogeneic stem cell transplants.

The use of induced pluripotent stem cells (iPSCs), rather than ES-derived cells, has the advantages of avoiding ethical concerns. Further, derivation of iPSCs from a patient to be treated (i.e., the patient receives an autologous cell transplant) avoids risks of immune rejection inherent in the use of embryonic stem cells. As previous studies revealed that poor standardization of transplanted cell material contributes to high variability, new methods of producing substantial numbers of standardized cells, such as for autologous stem cell transplant, are needed. Lindvall and Kokaia, *J. Clin. Invest* (2010) 120:29-40.

A study is currently underway in which human iPSCs were differentiated into DA neuron precursors and transplanted into the striatum of a human. However, the ability of these cells to survive, engraft, and innervate other cells in vivo has not yet been reported. Takahashi, *Brain Res*. (2017) 230:213-26 (2017); Cyranoski, D., *Nature News* (2018).

Thus, existing strategies have not yet proved to be successful in producing a population of differentiated cells for use in engraftment procedures for restoring neuronal function in vivo. Provided herein are methods of differentiating PSCs into determined dopaminergic neuron progenitor cells (DDPCs) and/or DA neurons cells. In particular, the provided methods are based on findings that initiating a culture of PSCs as non-adherent cells in the presence of SB, LDN, SHH, PUR, and CHIR to generate spheroid(s), followed by a further incubation of cells of the spheroid on a substrate-coated plate produces differentiated cells with superior properties. Further aspects of the provided methods include harvesting cells at a time at which the cells are determined dopaminergic (dopamine neuron) precursor cells that are cells that are able to differentiate into dopaminergic neurons but cannot differentiate into non-dopaminergic neurons. In some embodiments of the provided methods, such cells are cells that are differentiated in accord with the provided methods and are harvested at or about day 18.

In some cases, the methods described herein include culturing PSCs into spheroids in a non-adherent culture (i.e., suspension culture) for about 7 days, prior to dissociating the spheroids and continuing culture if the dissociated cells on a plate, e.g., a substrate-coated plate (i.e., as an adherent culture) until harvesting. The provided methods of differentiating cells in non-adherent cultures is associated with advantages compared to alternative methods, such as methods in which an entire process of differentiation is carried out by adherent culture of cells.

In some cases, the non-adherent culture of the provided methods is advantageous compared to differentiation methods that do not involve non-adherent culture of cells, because the effect of the variability of one or more substrates and/or one or more reagents on cell differentiation is reduced or eliminated during the non-adherent culture. Specifically, adherent culture may involve the coating of a plate with one or more substrates or reagents, and such coating may be uneven, thereby leading to variable provision of the one or more substrates and/or reagents to the adherent cells, particularly in methods in which the entire process of differentiation is carried out by adherent culture of cells. Such variable provision of substrates and/or reagents to adherent cells can increase variability in the harvested cells produced by the differentiation method. By contrast, substrates and/or reagents may either by unnecessary in a non-adherent culture, or are evenly dispersed throughout a non-adherent culture. In the case of the latter, the cultured cells (e.g., spheroids) are surrounded on all sides by the culture medium, such that cells are equally exposed to any substrates and/or reagents in the culture medium. Thus, in aspects of provided embodiments, cells produced by differentiation methods including non-adherent culture may exhibit reduced variability.

The non-adherent culture methods described herein are also advantageous compared to methods not including non-adherent culture, because non-adherent culture allows for increased cell-to-cell interaction. In particular, cells in an adherent (e.g., monolayer) culture only contact other cells on their lateral surfaces. By contrast, cells in a non-adherent (e.g., suspension) culture are able to contact other cells across their entire surfaces. Such increased cell-to-cell contact in a non-adherent culture may be advantageous by more faithfully recapitulating the physiological environment. For example, the increased cell-to-cell contact allowed by the non-adherent culture methods described herein may upregulate cell-to-cell protein networks, as observed in vivo.

In some aspects, methods involving provided non-adherent culture methods described herein provide for an case and efficiency of culturing a greater number of cells, as compared to alternative methods, such as methods in which an entire process of differentiation is carried out by adherent culture of cells. For example, in an adherent (e.g., monolayer) culture, the number of cells cultured increases on a two-dimensional scale (i.e., the length and width of the culturing surface) with the surface area of the culturing surface. By contrast, in a non-adherent (e.g., suspension) culture, the number of cells cultured increases on a three-dimensional scale with the volume of the culturing vessel, or the volume of the culture medium contained therein. Thus, in some cases, non-adherent culture is more economical and efficient, in that fewer resources (e.g., culture vessels and reagents) are used, more cells can be generated, or both, as compared to adherent culture. In this way, the provided methods of non-adherent culture can enable scaling in manufacturing and production processes.

Further, particular benefits are associated with methods of differentiating cells that include a non-adherent culture of only about 7 days. The non-adherent culture of about 7 days described herein produces spheroids. If non-adherent culture is allowed to proceed beyond 7 days, the increasing size of the spheroids may limit mass transport and result in reagent (e.g., morphogen) gradients across the diameter of the spheroids. Substantial reagent (e.g., morphogen) gradients across the diameter of the spheroids is undesirable, as different cells of the spheroids would be exposed to different concentration of a reagent (e.g., a morphogen), thereby leading to variable cell response and differentiation. Thus, the methods described herein including non-adherent culture of only about or up to 7 days are advantageous because variability in the concentration of reagents such as morphogen(s) to which the cells of the spheroids are exposed is minimized.

In some aspects, limiting the non-adherent culture component of the methods described herein to about 7 days also helps ensure the consistent differentiation of cultured cells. This is because long-term (e.g., greater than 7 days) differentiation of PSCs in non-adherent (e.g., suspension) culture may allow PSCs to establish a microenvironment allowing for self-renewal in a pluripotent state. Thus, the methods described herein ensure the consistent and effective differentiation of the cultured cells by reducing or eliminating the opportunity for PSCs to persist in culture.

In aspects of the provided methods, cells produced by the methods described herein are advantageous by virtue of exhibiting expression of A9 specific markers, evidencing their fate as A9 dopamine neurons and suitability for transplant, engraftment, and innervation of other cells in vivo.

In particular, cells produced by the methods described herein, including cells harvested on day 18 of differentiation, express EN1 and CORIN, genes expressed by A9 progenitors during fetal development. Cells harvested on day 25, as compared to cells harvested on day 18, of the exemplary differentiation methods described herein also demonstrate a downregulation in mitosis-related genes, indicating an increasing commitment to a particular cell type fate with increasing time in culture. In addition, cells produced by the methods described herein demonstrate an upregulation in expression of neurite outgrowth-related genes on day 25, compared to day 18. Neurite outgrowth-related genes are involved in the development of new neuronal projections and synaptogenesis. This finding therefore indicates that cells differentiated by the exemplary methods described herein are becoming more committed to a neuronal fate with increasing time in culture. Together, these features indicate that the day 18 harvested cells are committed dopaminergic neuron progenitor cells. Thus, the cells produced by the methods described herein, including differentiated cells harvested at day 18, may be advantageous compared to cells differentiated by other methods and/or harvested on different (i.e., later) days of a differentiation protocol, by virtue of being committed to a DA neuron fate but less differentiated than at a later day.

Findings herein also demonstrate that cells harvested on day 18 appear to express many markers of DA neuron precursors, but their genetic expression indicates they may be less committed to DA neuronal fate than cells harvested on day 25. In some embodiments, the day 18 harvested cells may therefore represent an ideal time point for the harvesting of cells for subsequent transplantation in vivo. In particular, one or more of the abilities to engraft, innervate, or improve efficacy may be improved compared to cells differentiated by other methods and/or harvested on different (i.e., later) days of a differentiation protocol.

In some embodiments, cells harvested on or about day 18 of the methods or therapeutic compositions containing same described herein may exhibit an improved ability to engraft and/or innervate other cells compared to cells harvested at later times of the differentiation method (e.g., day 25). In some embodiments, cells harvested on day 18 may also exhibit improved efficacy in vivo, due to their state of differentiation and neuronal commitment. For example, cells harvested on day 18 may demonstrate improved engraftment and/or innervation, improved efficacy, or both, as compared to cells harvested on day 25.

In some embodiments, cells harvested by the provided differentiation method exhibit therapeutic effect(s) to treat a neurodegenerative disease. In some embodiments, the ability for differentiated cells to treat a neurodegenerative disease can be determined in an animal model of a neurodegenerative disease. In some embodiments, the neurodegenerative disease is Parkinson's disease. In some embodiments, differentiated cells harvested by provided method are screened using an animal model of Parkinson's disease. Any known and available animal model of Parkinson's disease can be used for screening. In some embodiments, the animal model is a lesion model wherein animals receive unilateral stereotaxic injection of 6-hydroxydopamine (6-OHDA) into the substantia nigra. In some embodiments, the animal model is a lesion model wherein animals receive unilateral stereotaxic injection of 6-OHDA into the medial forebrain bundle. In some embodiments, a therapeutic composition containing differentiated cells produced by the provided method, e.g., harvested cells, such as day 18 ells, are implanted into the substantia nigra of the animal model. In some embodiments, a behavioral assay is performed to screen for therapeutic effects of the implantation on the animal model. In some embodiments, the behavioral assay comprises monitoring amphetamine-induced circling behavior. In some embodiments, differentiated cells exhibit a therapeutic effect to treat a neurodegenerative disease if such cells are determined to reduce, decrease or reverse a Parkinsonian model brain lesion in this model.

Further, unlike previously reported methods, the differentiated cells produced by the methods described herein demonstrate physiological consistency. Importantly, this physiological consistency is maintained across cells differentiated from different subjects. This method therefore reduces variability both within and among subjects, and allows for better predictability of cell behavior in vivo. These benefits are associated with a successful therapeutic strategy, especially in the setting of autologous stem cell transplant, where cells are generated separately for each patient. Such reproducibility benefits among different subjects may also enable scaling in manufacturing and production processes.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

II. METHODS FOR DIFFERENTIATING CELLS

Provided herein are methods of differentiating neural cells, involving (1) performing a first incubation including culturing pluripotent stem cells in a non-adherent culture vessel under conditions to produce a cellular spheroid, wherein beginning at the initiation of the first incubation (day 0) the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3β (GSK3β) signaling; and (b) performing a second incubation including culturing cells of the spheroid in a substrate-coated culture vessel under conditions to neurally differentiate the cells.

The provided methods of differentiating neural cells, such as by subjecting iPSCs to cell culture methods that induce their differentiation into floor plate midbrain progenitor cells, determined dopamine (DA) neuron progenitor cells, and/or dopamine (DA) neurons.

As described herein, iPSCs were generated from fibroblasts of human patients with Parkinson's disease. In a first incubation, the iPSCs were then differentiated to midbrain floor plate precursors and grown as spheroids in a non-adherent culture by exposure to small molecules, such as LDN, SB, PUR, SHH, CHIR, and combinations thereof, beginning on day 0. The resulting spheroids were then transferred to an adherent culture as part of a second incubation, optionally following dissociation of the spheroid, before being exposed to additional small molecules (e.g., LDN, CHIR, BDNF, GDNF, ascorbic acid, dbcAMP, TGFβ3, DAPT, and combinations thereof) to induce further differentiation into engraftable determined DA neuron progenitor cells or DA neurons.

A. Samples and Cell Preparation

In embodiments of the provided method, pluripotent stem cells are differentiated into floor plate midbrain progenitor cells, determined dopamine (DA) neuron progenitor cells, and/or dopamine (DA) neurons. Various sources of pluripotent stem cells can be used in the method, including embryonic stem (ES) cells and induced pluripotent stem cells (iPSCs).

In some aspects, pluripotency refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells. In some aspects, pluripotent stem cells can be distinguished from other cells by particular characteristics, including by expression or non-expression of certain combinations of molecular markers. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. In some aspects, a pluripotent stem cell characteristic is a cell morphologies associated with pluripotent stem cells.

In some embodiments, pluripotent stem cells are induced pluripotent stem cells (iPSCs), artificially derived from a non-pluripotent cell. In some aspects, a non-pluripotent cell is a cell of lesser potency to self-renew and differentiate than a pluripotent stem cell. iPSCs may be generated by a process known as reprogramming, wherein non-pluripotent cells are effectively "dedifferentiated" to an embryonic stem cell-like state by engineering them to express genes such as OCT4, SOX2, and KLF4. Takahashi and Yamanaka, Cell (2006) 126:663-76.

Methods for generating iPSCs are known. For example, mouse iPSCs were reported in 2006 (Takahashi and Yamanaka), and human iPSCs were reported in late 2007 (Takahashi et al. and Yu et al.). Mouse iPSCs demonstrate important characteristics of pluripotent stem cells, including the expression of stem cell markers, the formation of tumors containing cells from all three germ layers, and the ability to contribute to many different tissues when injected into mouse embryos at a very early stage in development. Human iPSCs also express stem cell markers and are capable of generating cells characteristic of all three germ layers.

In some embodiments, the PSCs (e.g., iPSCs) are autologous to the subject to be treated, i.e., the PSCs are derived from the same subject to whom the differentiated cells are administered. In some embodiments, non-pluripotent cells (e.g., fibroblasts) derived from patients having Parkinson's disease (PD) are reprogrammed to become iPSCs before differentiation into neural and/or neuronal cells. In some embodiments, fibroblasts may be reprogrammed to iPSCs by transforming fibroblasts with genes (OCT4, SOX2, NANOG, LIN28, and KLF4) cloned into a plasmid (for example, see, Yu, et al., *Science* DOI: 10.1126/science.1172482). In some embodiments, non-pluripotent fibroblasts derived from patients having PD are reprogrammed to become iPSCs before differentiation into determined DA neuron progenitor cells and/or DA neurons, such as by use of the non-integrating Sendai virus to reprogram the cells (e.g., use of CTS™ CytoTune™-iPS 2.1 Sendai Reprogramming Kit). In some embodiments, the resulting differentiated cells are then administered to the patient from whom they are derived in an autologous stem cell transplant. In some embodiments, the PSCs (e.g., iPSCs) are allogeneic to the subject to be treated, i.e., the PSCs are derived from a different individual than the subject to whom the differentiated cells will be administered. In some embodiments, non-pluripotent cells (e.g., fibroblasts) derived from another individual (e.g., an individual not having a neurodegenerative disorder, such as Parkinson's disease) are reprogrammed to become iPSCs before differentiation into determined DA neuron progenitor cells and/or DA neurons. In some embodiments, reprogramming is accomplished, at least in part, by use of the non-integrating Sendai virus to reprogram the cells (e.g., use of CTS™ CytoTune™-iPS 2.1 Sendai Reprogramming Kit). In some embodiments, the resulting differentiated cells are then administered to an individual who is not the same individual from whom the differentiated cells are derived (e.g., allogeneic cell therapy or allogeneic cell transplantation).

In any of the provided embodiments, the PSCs described herein (e.g., allogeneic cells) may be genetically engineered to be hypoimmunogenic. Methods for reducing the immunogenicity are known, and include ablating polymorphic HLA-A/-B/-C and HLA class II molecule expression and introducing the immunomodulatory factors PD-L1, HLA-G, and CD47 into the AAVS1 safe harbor locus in differentiated cells. Han et al., *PNAS* (2019) 116 (21): 10441-46. Thus, in some embodiments, the PSCs described herein are engineered to delete highly polymorphic HLA-A/-B/-C genes and to introduce immunomodulatory factors, such as PD-L1, HLA-G, and/or CD47, into the AAVS1 safe harbor locus.

In some embodiments, PSC (e.g., iPSCs) are cultured in the absence of feeder cells, until they reach 80-90% confluency, at which point they are harvested and further cultured for differentiation (day 0). In one aspect of the method described herein, once iPSCs reach 80-90% confluence, they are washed in phosphate buffered saline (PBS) and subjected to enzymatic dissociation, such as with Accutase®, until the cells are easily dislodged from the surface of a culture vessel. The dissociated iPSCs are then re-suspended in media for downstream differentiation into determined DA neuron progenitor cells and/or DA neurons.

In some embodiments, the PSCs are resuspended in a basal induction media. In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, the basal induction media is further supplemented with serum replacement, a Rho-associated protein kinase (ROCK) inhibitor, and various small molecules, for differentiation. In some embodiments, the PSCs are resuspended in the same media they will be cultured in for at least a portion of the first incubation.

B. Non-Adherent Culture

The provided methods include culturing PSCs (e.g., iPSCs) by incubation with certain molecules (e.g., small molecules) to induce their differentiation into floor plate midbrain progenitor cells, determined dopamine (DA) neuron progenitor cells, and/or dopamine (DA) neurons. In particular, the provided embodiments include a first incubation of PSCs under non-adherent conditions to produce spheroids, in the presence of certain molecules (e.g., small molecules), which can, in some aspects, improve the consistency of producing physiologically relevant cells for implantation. In some embodiments, the methods include performing a first incubation involving culturing pluripotent stem cells in a non-adherent culture vessel under conditions to produce a cell spheroid, wherein beginning at the initiation of the first incubation (day 0) the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3β (GSK3β) signaling.

In some embodiments, a non-adherent culture vessel is a culture vessel with a low or ultra-low attachment surface, such as to inhibit or reduce cell attachment. In some embodiments, culturing cells in a non-adherent culture vessel does not prevent all cells of the culture from attaching the surface of the culture vessel.

In some embodiments, a non-adherent culture vessel is a culture vessel with an ultra-low attachment surface. In some aspects, an ultra-low attachment surface may inhibit cell attachment for a period of time. In some embodiments, an ultra-low attachment surface may inhibit cell attachment for the period of time necessary to obtain confluent growth of the same cell type on an adherent surface. In some embodiments, the ultra-low attachment surface is coated or treated with a substance to prevent cell attachment, such as a hydrogel layer (e.g., a neutrally charged and/or hydrophilic hydrogel layer). In some embodiments, a non-adherent culture vessel is coated or treated with a surfactant prior to the first incubation. In some embodiments, the surfactant is pluronic acid.

In some embodiments, the non-adherent culture vessel is a plate, a dish, a flask, or a bioreactor. In some embodiments, the non-adherent culture vessel is a plate, such as a multi-well plate. In some embodiments, the non-adherent culture vessel is a 6-well or 24-well plate. In some embodiments, the wells of the multi-well plate further include micro-wells. In some any of the provided embodiments, a non-adherent culture vessel, such as a multi-well plate, has round or concave wells and/or microwells. In any of the provided embodiments, a non-adherent culture vessel, such as a multi-well plate, does not have corners or seams.

In some embodiments, a non-adherent culture vessel allows for three-dimensional formation of cell aggregates. In some embodiments, iPSCs are cultured in a non-adherent culture vessel, such as a multi-well plate, to produce cell aggregates (e.g., spheroids). In some embodiments, iPSCs are cultured in a non-adherent culture vessel, such as a multi-well plate, to produce cell aggregates (e.g., spheroids) on about day 7 of the method. In some embodiments, the cell aggregate (e.g., spheroid) expresses at least one of PAX6 and OTX2 on or by about day 7 of the method.

In some embodiments, the first incubation includes culturing pluripotent stem cells in a non-adherent culture vessel under conditions to produce a cellular spheroid.

In some embodiments, the number of PSCs plated on day 0 of the method is between about between about $0.1\times10^6$ cells/cm$^2$ and about $2\times10^6$ cells/cm$^2$, between about $0.1\times10^6$ cells/cm$^2$ and about $1\times10^6$ cells/cm$^2$, between about $0.1\times10^6$ cells/cm$^2$ and about $0.8\times10^6$ cells/cm$^2$, between about $0.1\times10^6$ cells/cm$^2$ and about $0.6\times10^6$ cells/cm$^2$, between about $0.1\times10^6$ cells/cm$^2$ and about $0.4\times10^6$ cells/cm$^2$, between about $0.1\times10^6$ cells/cm$^2$ and about $0.2\times10^6$ cells/cm$^2$, between about $0.2\times10^6$ cells/cm$^2$ and about $2\times10^6$ cells/cm$^2$, between about $0.2\times10^6$ cells/cm$^2$ and about $1\times10^6$ cells/cm$^2$, between about $0.2\times10^6$ cells/cm$^2$ and about $0.8\times10^6$ cells/cm$^2$, between about $0.2\times10^6$ cells/cm$^2$ and about $0.6\times10^6$ cells/cm$^2$, between about $0.2\times10^6$ cells/cm$^2$ and about $0.4\times10^6$ cells/cm$^2$, between about $0.4\times10^6$ cells/cm$^2$ and about $2\times10^6$ cells/cm$^2$, between about $0.4\times10^6$ cells/cm$^2$ and about $1\times10^6$ cells/cm$^2$, between about $0.4\times10^6$ cells/cm$^2$ and about $0.8\times10^6$ cells/cm$^2$, between about $0.4\times10^6$ cells/cm$^2$ and about $0.6\times10^6$ cells/cm$^2$, between about $0.6\times10^6$ cells/cm$^2$ and about $2\times10^6$ cells/cm$^2$, between about $0.6\times10^6$ cells/cm$^2$ and about $1\times10^6$ cells/cm$^2$, between about $0.6\times10^6$ cells/cm$^2$ and about $0.8\times10^6$ cells/cm$^2$, between about $0.8\times10^6$ cells/cm$^2$ and about $2\times10^6$ cells/cm$^2$, between about $0.8\times10^6$ cells/cm$^2$ and about $1\times10^6$ cells/cm$^2$, or between about $1.0\times10^6$ cells/cm$^2$ and about $2\times10^6$ cells/cm$^2$. In some embodiments, the number of cells plated on the substrate-coated culture vessel is between about $0.4\times10^6$ cells/cm$^2$ and about $0.8\times10^6$ cells/cm$^2$.

In some days, the number of PSCs plated on day 0 of the method is a number of cells sufficient to produce a cellular spheroid containing between about 1,000 cells and about 5,000 cells, or between about 2,000 cells and about 3,000 cells. In some days, the number of PSCs plated on day 0 of the method is a number of cells sufficient to produce a cellular spheroid containing between about 1,000 cells and about 5,000 cells. In some days, the number of PSCs plated on day 0 of the method is a number of cells sufficient to produce a cellular spheroid containing between about 2,000 cells and about 3,000 cells. In some days, the number of PSCs plated on day 0 of the method is a number of cells sufficient to produce a cellular spheroid containing about 2,000 cells. In some days, the number of PSCs plated on day 0 of the method is a number of cells sufficient to produce a cellular spheroid containing about 3,000 cells. In some embodiments, the spheroids containing the desired number is produced by the method on or by about day 7.

In some embodiments of the method provided herein, the first incubation includes culturing pluripotent stem cells in a non-adherent culture vessel under conditions to produce a cellular spheroid. In some embodiments, the first incubation is from about day 0 through about day 6. In some embodiments, the first incubation comprises culturing pluripotent stem cells in a culture media ("media"). In some embodiments, the first incubation comprises culturing pluripotent stem cells in the media from about day 0 through about day 6. In some embodiments, the first incubation comprises culturing pluripotent stem cells in the media to induce differentiation of the PSCs into floor plate midbrain progenitor cells.

In some embodiments, the media is also supplemented with a serum replacement containing minimal non-human-derived components (e.g., KnockOut™ serum replacement). In some embodiments, the serum replacement is provided in the media at 5% (v/v) for at least a portion of the first incubation. In some embodiments, the serum replacement is provided in the media at 5% (v/v) on day 0 and day 1. In some embodiments, the serum replacement is provided in the media at 2% (v/v) for at least a portion of the first incubation. In some embodiments, the serum replacement is provided in the media at 2% (v/v) from day 2 through day 6. In some embodiments, the serum replacement is provided in the media at 5% (v/v) on day 0 and day 1, and at 2% (v/v) from day 2 through day 6.

In some embodiments, the media is further supplemented with small molecules, such as any described above. In some embodiments, the small molecules are selected from among the group consisting of: a Rho-associated protein kinase (ROCK) inhibitor, an inhibitor of TGF-β/activin-Nodal signaling, at least one activator of Sonic Hedgehog (SHH) signaling, an inhibitor of bone morphogenetic protein (BMP) signaling, an inhibitor of glycogen synthase kinase 3β (GSK3β) signaling, and combinations thereof.

In some embodiments the media is supplemented with a Rho-associated protein kinase (ROCK) inhibitor on one or more days when cells are passaged. In some embodiments the media is supplemented with a ROCK inhibitor each day that cells are passaged. In some embodiments the media is supplemented with a ROCK inhibitor on day 0.

In some embodiments, cells are exposed to the ROCK inhibitor at a concentration of between about 1 μM and about 20 μM, between about 5 μM and about 15 μM, or between about 8 μM and about 12 μM. In some embodiments, cells are exposed to the ROCK inhibitor at a concentration of between about 1 μM and about 20 μM. In some embodiments, cells are exposed to the ROCK inhibitor at a concentration of between about 5 M and about 15 μM. In some embodiments, cells are exposed to the ROCK inhibitor at a concentration of between about 8 μM and about 12 μM. In some embodiments, cells are exposed to the ROCK inhibitor at a concentration of about 10 μM.

In some embodiments, the ROCK inhibitor is selected from among the group consisting of: fasudil, ripasudil, netarsudil, RKI-1447, Y-27632, GSK429286A, Y-30141, and combinations thereof. In some embodiments, the ROCK inhibitor is a small molecule. In some embodiments, the ROCK inhibitor selectively inhibits p160ROCK. In some embodiments, the ROCK inhibitor is Y-27632, having the formula:

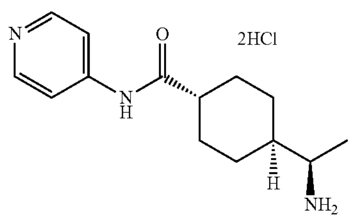 [SMILES: C[C@@H](N)[C@H]1CC[C@H](C(=O)Nc2ccncc2)CC1]

In some embodiments, cells are exposed to Y-27632 at a concentration of about 10 μM. In some embodiments, cells are exposed to Y-27632 at a concentration of about 10 μM on day 0.

In some embodiments the media is supplemented with an inhibitor of TGF-β/activin-Nodal signaling. In some embodiments the media is supplemented with an inhibitor of TGF-β/activin-Nodal signaling up to about day 7 (e.g., day 6 or day 7). In some embodiments the media is supplemented with an inhibitor of TGF-β/activin-Nodal signaling from about day 0 through day 6, each day inclusive.

In some embodiments, cells are exposed to the inhibitor of TGF-β/activin-Nodal signaling at a concentration of between about 1 μM and about 20 μM, between about 5 UM and about 15 μM, or between about 8 μM and about 12 μM. In some embodiments, cells are exposed to the inhibitor of TGF-β/activin-Nodal signaling at a concentration of between about 1 μM and about 20 μM. In some embodiments, cells are exposed to the inhibitor of TGF-β/activin-Nodal signaling at a concentration of between about 5 μM and about 15 μM. In some embodiments, cells are exposed to the inhibitor of TGF-β/activin-Nodal signaling at a concentration of between about 8 UM and about 12 μM. In some embodiments, cells are exposed to the inhibitor of TGF-β/activin-Nodal signaling at a concentration of about 10 μM.

In some embodiments, the inhibitor of TGF-β/activin-Nodal signaling is a small molecule. In some embodiments, the inhibitor of TGF-β/activin-Nodal signaling is capable of lowering or blocking transforming growth factor beta (TGFβ)/activin-Nodal signaling. In some embodiments, the inhibitor of TGF-β/activin-Nodal signaling inhibits ALK4, ALK5, ALK7, or combinations thereof. In some embodiments, the inhibitor of TGF-β/activin-Nodal signaling inhibits ALK4, ALK5, and ALK7. In some embodiments, the inhibitor of TGF-β/activin-Nodal signaling does not inhibit ALK2, ALK3, ALK6, or combinations thereof. In some embodiments, the inhibitor does not inhibit ALK2, ALK3, or ALK6. In some embodiments, the inhibitor of TGF-β/activin-Nodal signaling is SB431542 (e.g., CAS 301836-41-9, molecular formula of $C_{22}H_{18}N_4O_3$, and name of 4-[4-(1,3-benzodioxol-5-yl)-5-(2-pyridinyl)-1H-imidazol-2-yl]-benzamide), having the formula:

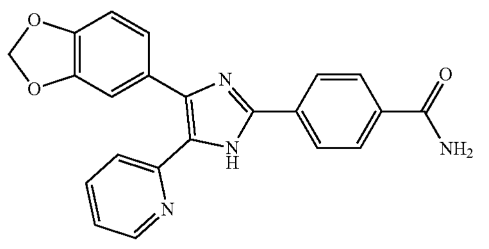 [SMILES: NC(=O)c1ccc(-c2nc(-c3ccc4c(c3)OCO4)c(-c3ccccn3)[nH]2)cc1]

In some embodiments, cells are exposed to SB431542 at a concentration of about 10 μM. In some embodiments, cells are exposed to SB431542 at a concentration of about 10 μM until about day 7. In some embodiments, cells are exposed to SB431542 at a concentration of about 10 μM from about day 0 through about day 6, inclusive of each day.

In some embodiments the media is supplemented with at least one activator of sonic hedghehog (SHH) signaling. SHH refers to a protein that is one of at least three proteins in the mammalian signaling pathway family called hedgehog, another is desert hedgehog (DHH) while a third is Indian hedgehog (IHH). Shh interacts with at least two transmembrane proteins by interacting with transmembrane molecules Patched (PTC) and Smoothened (SMO). In some embodiments the media is supplemented with the at least one activator of SHH signaling up to about day 7 (e.g., day 6 or day 7). In some embodiments the media is supplemented with the at least one activator of SHH signaling from about day 0 through day 6, each day inclusive.

In some embodiments, the at least one activator of SHH signaling is SHH protein. In some embodiments, the at least one activator of SHH signaling is recombinant SHH protein. In some embodiments, the at least one activator of SHH signaling is recombinant mouse SHH protein. In some embodiments, the at least one activator of SHH signaling is recombinant human SHH protein. In some embodiments, the least one activator of SHH signaling is a recombinant N-Terminal fragment of a full-length murine sonic hedgehog protein capable of binding to the SHH receptor for activating SHH. In some embodiments, the at least one activator of SHH signaling is C25II SHH protein.

In some embodiments, cells are exposed to the at least one activator of SHH signaling at a concentration of between about 10 ng/mL and about 500 ng/ml, between about 20 ng/ml and 400 μg/mL, between about 30 ng/mL and about 300 ng/mL, between about about 40 ng/mL and about 200 ng/mL, or between about 50 ng/ml and about 100 ng/mL, each inclusive. In some embodiments, cells are exposed to the at least one activator of SHH signaling at a concentration of between about 50 ng/mL and about 100 ng/ml, each inclusive. In some embodiments, cells are exposed to the at least one activator of SHH signaling at a concentration of about 100 ng/mL. In some embodiments, the cells are exposed to SHH protein at about 100 ng/mL. In some embodiments, the cells are exposed to recombinant SHH protein at about 100 ng/ml. In some embodiments, the cells are exposed to recombinant mouse SHH protein at about 100 ng/mL. In some embodiments, the cells are exposed to C25II SHH protein at about 100 ng/mL.

In some embodiments, cells are exposed to recombinant SHH protein at a concentration of about 10 ng/mL. In some embodiments, cells are exposed to recombinant SHH protein at a concentration of about 10 ng/mL up to about day 7 (e.g., day 6 or day 7). In some embodiments, cells are exposed to recombinant SHH protein at a concentration of about 10 ng/mL from about day 0 through about day 6, inclusive of each day.

In some embodiments, cells are exposed to the at least one activator of SHH signaling at a concentration of between about 1 μM and about 20 μM, between about 5 μM and about 15 μM, or between about 8 μM and about 12 μM. In some embodiments, cells are exposed to the at least one activator of SHH signaling at a concentration of between about 1 μM and about 20 μM. In some embodiments, cells are exposed to the at least one activator of SHH signaling at a concentration of between about 5 μM and about 15 μM. In some embodiments, cells are exposed to the at least one activator of SHH signaling at a concentration of between about 8 μM and about 12 μM. In some embodiments, cells are exposed to the at least one activator of SHH signaling at a concentration of about 10 μM.

In some embodiments, the at least one activator of SHH signaling is an activator of the Hedgehog receptor Smoothened. It some embodiments, the at least one activator of SHH signaling is a small molecule. In some embodiments, the least one activator of SHH signaling is purmorphamine (e.g., CAS 483367-10-8), having the formula below:

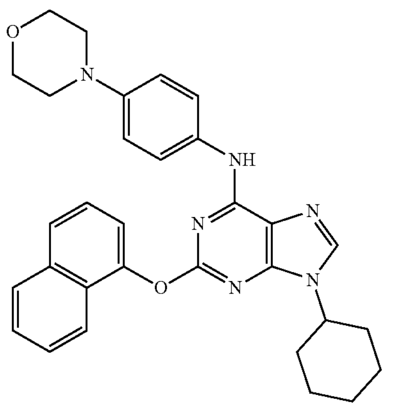 [SMILES: c1ccc2c(Oc3nc(Nc4ccc(N5CCOCC5)cc4)c4ncn(C5CCCCC5)c4n3)cccc2c1]

In some embodiments, cells are exposed to purmorphamine at a concentration of about 10 μM. In some embodiments, cells are exposed to purmorphamine at a concentration of about 10 μM up to day 7 (e.g., day 6 or day 7). In some embodiments, cells are exposed to purmorphamine at a concentration of about 10 μM from about day 0 through about day 6, inclusive of each day.

In some embodiments, the at least one activator of SHH signaling is SHH protein and purmorphamine. In some embodiments, cells are exposed to SHH protein and purmorphamine at a concentration up to about day 7 (e.g., day 6 or day 7). In some embodiments, cells are exposed to SHH protein and purmorphamine from about day 0 through about day 6, inclusive of each day. In some embodiments, cells are exposed to 100 ng/ml SHH protein and 10 μM purmorphamine at a concentration up to about day 7 (e.g., day 6 or day 7). In some embodiments, cells are exposed to 100 ng/mL SHH protein and 10 μM purmorphamine from about day 0 through about day 6, inclusive of each day.

In some embodiments the media is supplemented with an inhibitor of BMP signaling. In some embodiments the media is supplemented with an inhibitor of BMP signaling up to about day 7 (e.g., day 6 or day 7). In some embodiments the media is supplemented with an inhibitor of BMP signaling from about day 0 through day 6, each day inclusive.

In some embodiments, cells are exposed to the inhibitor of BMP signaling at a concentration of between about 0.01 UM and about 5 μM, between about 0.05 UM and about 1 μM, or between about 0.1 μM and about 0.5 μM, each inclusive. In some embodiments, cells are exposed to the inhibitor of BMP signaling at a concentration of between about 0.01 UM and about 5 μM. In some embodiments, cells are exposed to the inhibitor of BMP signaling at a concentration of between about 0.05 UM and about 1 μM. In some embodiments, cells are exposed to the inhibitor of BMP signaling at a concentration of between about 0.1 μM and about 0.5 μM. In some embodiments, cells are exposed to the inhibitor of BMP signaling at a concentration of about 0.1 μM.

In some embodiments, the inhibitor of BMP signaling is a small molecule. In some embodiments, the inhibitor of BMP signaling is selected from LDN193189 or K02288. In some embodiments, the inhibitor of BMP signaling is capable of inhibiting "Small Mothers Against Decapentaplegic" SMAD signaling. In some embodiments, the inhibitor of BMP signaling inhibits ALK1, ALK2, ALK3, ALK6, or combinations thereof. In some embodiments, the inhibitor of BMP signaling inhibits ALK1, ALK2, ALK3, and ALK6. In some embodiments, the inhibitor of BMP signaling inhibits BMP2, BMP4, BMP6, BMP7, and Activin cytokine signals and subsequently SMAD phosphorylation of Smad1, Smad5, and Smad8. In some embodiments, the inhibitor of BMP signaling is LDN193189. In some embodiments, the inhibitor of BMP signaling is LDN193189 (e.g., IUPAC name 4-(6-(4-(piperazin-1-yl)phenyl) pyrazolo[1,5-a]pyrimidin-3-yl) quinoline, with a chemical formula of $C_{25}H_{22}N_6$), having the formula:

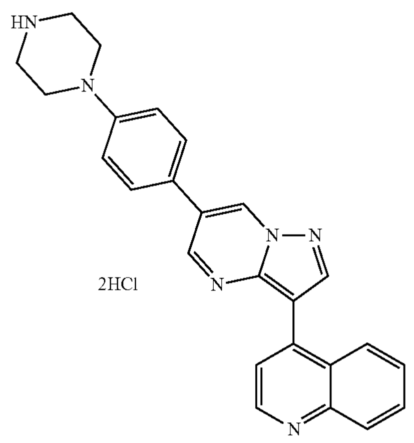 [SMILES: c1ccc2c(-c3cnn4cc(-c5ccc(N6CCNCC6)cc5)cnc34)ccnc2c1]

In some embodiments, cells are exposed to LDN193189 at a concentration of about 0.1 μM. In some embodiments, cells are exposed to LDN193189 at a concentration of about 0.1 μM up to about day 7 (e.g., day 6 or day 7). In some embodiments, cells are exposed to LDN193189 at a concentration of about 0.1 μM from about day 0 through about day 6, inclusive of each day.

In some embodiments the media is supplemented with an inhibitor of GSK3B signaling. In some embodiments the media is supplemented with an inhibitor of GSK3β signaling up to about day 7 (e.g., day 6 or day 7). In some embodiments the media is supplemented with an inhibitor of GSK3β signaling from about day 0 through day 6, each day inclusive.

In some embodiments, cells are exposed to the inhibitor of GSK3β signaling at a concentration of between about 0.1 μM and about 10 μM, between about 0.5 μM and about 8 μM, or between about 1 μM and about 4 μM, or between about 2 μM and about 3 μM, each inclusive. In some embodiments, cells are exposed to the inhibitor of GSK3β signaling at a concentration of between about 0.1 μM and about 10 μM. In some embodiments, cells are exposed to the inhibitor of GSK3β signaling at a concentration of between about 0.5 μM and about 8 μM. In some embodiments, cells are exposed to the inhibitor of BMP signaling at a concentration of between about 1 μM and about 4 μM. In some embodiments, cells are exposed to the inhibitor of BMP signaling at a concentration of between about 2 μM and about 3 μM. In some embodiments, cells are exposed to the inhibitor of GSK3β signaling at a concentration of about 2 μM.

In some embodiments, the inhibitor of GSK3β signaling is selected from among the group consisting of: lithium ion, valproic acid, iodotubercidin, naproxen, famotidine, curcumin, olanzapine, CHIR99012, and combinations thereof. In some embodiments, the inhibitor of GSK3β signaling is a small molecule. In some embodiments, the inhibitor of GSK3β signaling inhibits a glycogen synthase kinase 3β enzyme. In some embodiments, the inhibitor of GSK3β signaling inhibits GSK3α. In some embodiments, the inhibitor of GSK3B signaling modulates TGF-β and MAPK signaling. In some embodiments, the inhibitor of GSK3β signaling is an agonist of wingless/integrated (Wnt) signaling. In some embodiments, the inhibitor of GSK3β signaling has an IC50-6.7 nM against human GSK3β. In some embodiments, the inhibitor of GSK3β signaling is CHIR99021 (e.g., "3-[3-(2-Carboxyethyl)-4-methylpyrrol-2-methylidenyl]-2-indolinone" or IUPAC name 6-(2-(4-(2,4-dichlorophenyl)-5-(4-methyl-1H-imidazol-2-yl)pyrimidin-2-ylamino)ethylamino)nicotinonitrile), having the formula:

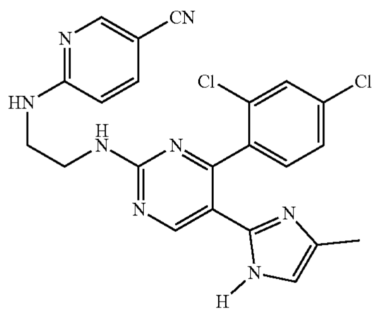 [SMILES: Cc1c[nH]c(-c2cnc(NCCNc3ccc(C#N)cn3)nc2-c2ccc(Cl)cc2Cl)n1]

In some embodiments, cells are exposed to CHIR99021 at a concentration of about 2.0 μM. In some embodiments, cells are exposed to CHIR99021 at a concentration of about 2.0 μM up to about day 7 (e.g., day 6 or day 7). In some embodiments, cells are exposed to CHIR99021 at a concentration of about 2.0 M from about day 0 through about day 6, inclusive of each day.

In some embodiments, from day about 2 to about day 6, at least about 50% of the media is replaced daily. In some embodiments, from about day 2 to about day 6, about 50% of the media is replaced daily, every other day, or every third day. In some embodiments, from about day 2 to about day 6, about 50% of the media is replaced daily. In some embodiments, at least about 75% of the media is replaced on day 1. In some embodiments, about 100% of the media is replaced on day 1. In some embodiments, the replacement media contains small molecules about twice as concentrated as compared to the concentration of the small molecules in the media on day 0.

In some embodiments, the first incubation comprises culturing pluripotent stem cells in a "basal induction media." In some embodiments, the first incubation comprises culturing pluripotent stem cells in the basal induction media from about day 0 through about day 6. In some embodiments, the first incubation comprises culturing pluripotent stem cells in the basal induction media to induce differentiation of the PSCs into floor plate midbrain progenitor cells.

In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, the basal induction media is further supplemented with any of the small molecules as described above.

C. Transfer or Dissociation of Spheroids

In some embodiments, cell aggregates (e.g., spheroids) that are produced following the first incubation of culturing pluripotent stem cells in a non-adherent culture vessel are transferred or dissociated, prior to carrying out a second incubation of the cells on a substrate (adherent culture).

In some embodiments, the first incubation is carried out to produce a cell aggregate (e.g., a spheroid) that expresses at least one of PAX6 and OTX2. In some embodiments, the first incubation produces a cell aggregate (e.g., a spheroid) that expresses PAX6 and OTX2. In some embodiments, the first incubation produces a cell aggregate (e.g., a spheroid) on or by about day 7 of the methods provided herein. In some embodiments, the first incubation produces a cell aggregate (e.g., a spheroid) that expresses at least one of PAX6 and OTX2 on or by about day 7 of the methods provided herein. In some embodiments, the first incubation produces a cell aggregate (e.g., a spheroid) that expresses PAX6 and OTX2 on or by about day 7 of the methods provided herein.

In some embodiments, the cell aggregate (e.g., spheroid) produced by the first incubation is dissociated prior to the second incubation of the cells on a substrate. In some embodiments, the cell aggregate (e.g., spheroid) produced by the first incubation is dissociated to produce a cell suspension. In some embodiments, the cell suspension produced by the dissociation is a single cell suspension. In some embodiments, the dissociation is carried out at a time when the spheroid cells express at least one of PAX6 and OTX2. In some embodiments, the dissociation is carried out at a time when the spheroid cells express PAX6 and OTX2. In some embodiments, the dissociation is carried out on about day 7. In some embodiments, the cell aggregate (e.g., spheroid) is dissociated by enzymatic dissociation. In some embodiments, the enzyme is selected from among the group consisting of: Accutase®, Dispase®, collagenase, and combinations thereof. In some embodiments, the enzyme comprises Accutase®. In some embodiments, the enzyme is Accutase®. In some embodiments, the enzyme is Dispase®. In some embodiments, the enzyme is collagenase.

In some embodiments, the cell aggregate or cell suspension produced therefrom is transferred to a substrate-coated culture vessel for a second incubation. In some embodiments, the cell aggregate (e.g. spheroid) or cell suspension produced therefrom is transferred to a substrate-coated culture vessel following dissociation of the cell aggregate (e.g. spheroid). In some embodiments, the transferring is carried out immediately after the dissociation. In some embodiments, the transferring is carried out on about day 7.

In some embodiments, the cell aggregate (e.g., spheroid) is not dissociated prior to a second incubation. In some embodiments, a cell aggregate (e.g. spheroid) is transferred in its entirety to a substrate-coated culture vessel for a second incubation. In some embodiments, the transferring is carried out at a time when the spheroid cells express at least one of PAX6 and OTX2. In some embodiments, the transferring is carried out at a time when the spheroid cells express PAX6 and OTX2. In some embodiments, the transferring is carried out on about day 7.

In some embodiments, the transferring is to an adherent culture vessel. In some embodiments, the culture vessel is a plate, a dish, a flask, or a bioreactor. In some embodiments, the culture vessel is substrate-coated. In some embodiments, the substrate is a basement membrane protein. In some embodiments, the substrate is selected from laminin, collagen, entactin, heparin sulfate proteoglycans, and combinations thereof. In some embodiments, the substrate is laminin. In some embodiments, the substrate is recombinant. In some embodiments, the substrate is recombinant laminin. In some embodiments, the substrate-coated culture vessel is exposed to poly-L-ornithine, optionally prior to being used for culturing cells. In some embodiments, the substrate-coated culture vessel is a 6-well or 24-well plate. In some embodiments, the substrate-coated culture vessel is a 6-well plate. In some embodiments, the substrate-coated culture vessel is a 24-well plate.

D. Adherent Culture

In some embodiments, the methods include performing a second incubation of the spheroid cells transferred to the substrate-coated culture vessel. In some embodiments, culturing the cells of the spheroid in the substrate-coated culture vessel under adherent conditions induces their differentiation into floor plate midbrain progenitor cells, determined dopamine (DA) neuron progenitor cells, and/or dopamine (DA) neurons.

In some embodiments, the second incubation involves culturing cells of the spheroid in a culture vessel coated with a substrate including laminin, collagen, entactin, heparin sulfate proteoglycans, or a combination thereof, wherein beginning on day 7, the cells are exposed to (i) an inhibitor of BMP signaling and (ii) an inhibitor of GSK3β signaling; and beginning on day 11, the cells are exposed to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling. In some embodiments, the method further includes harvesting the differentiated cells.

In some embodiments, the substrate-coated culture vessel is a culture vessel with a surface to which cells can attach. In some embodiments, the substrate-coated culture vessel is a culture vessel with a surface to which a substantial number of cells attach. In some embodiments, the substrate is a basement membrane protein. In some embodiments, the substrate is laminin, collagen, entactin, heparin sulfate proteoglycans, or a combination thereof. In some embodiments, the substrate is laminin. In some embodiments, the substrate is collagen. In some embodiments, the substrate is entactin. In some embodiments, the substrate is heparin sulfate proteoglycans. In some embodiments, the substrate is a recombinant protein. In some embodiments, the substrate is recombinant laminin. In some embodiments, the substrate-coated culture vessel is exposed to poly-L-ornithine. In some embodiments, the substrate-coated culture vessel is exposed to poly-L-ornithine prior to being used for cell culture.

In some embodiments, the substrate-coated culture vessel is a plate, a dish, a flask, or a bioreactor. In some embodiments, the substrate-coated culture vessel is a plate, such as a multi-well plate. In some embodiments, the substrate-coated culture vessel is a plate. In some embodiments, the substrate-coated culture vessel is a 6-well or 24-well plate. In some embodiments, the substrate-coated culture vessel is a dish. In some embodiments, the substate-coated culture vessel is a flask. In some embodiments, the substrate-coated culture vessel is a bioreactor.

In some embodiments, the substrate-coated culture vessel allows for a monolayer cell culture. In some embodiments, cells derived from the cell aggregate (e.g., spheroid) produced by the first incubation are cultured in a monolayer culture on the substrate-coated plates. In some embodiments, cells derived from the cell aggregate (e.g., spheroid) produced by the first incubation are cultured to produce a monolayer culture of cells positive for one or more of LMX1A, FOXA2, EN1, CORIN, and combinations thereof. In some embodiments, cells derived from the cell aggregate (e.g., spheroid) produced by the first incubation are cultured to produce a monolayer culture of cells, wherein at least some of the cells are positive for EN1 and CORIN. In some embodiments, cells derived from the cell aggregate (e.g., spheroid) produced by the first incubation are cultured to produce a monolayer culture of cells, wherein at least some of the cells are $TH^+$. In some embodiments, at least some cells are $TH^+$ by or on about day 25. In some embodiments, cells derived from the cell aggregate (e.g., spheroid) produced by the first incubation are cultured to produce a monolayer culture of cells, wherein at least some of the cells are $TH^+FOXA2^+$. In some embodiments, at least some cells are $TH^+FOXA2^+$ by or on about day 25.

In the methods provided herein, the second incubation involves culturing cells of the spheroid in a substrate-coated culture vessel under conditions to induce neural differentiation of the cells. In some embodiments, the cells of the spheroid are plated on the substrate-coated culture vessel on about day 7.

In some embodiments, the number of cells plated on the substrate-coated culture vessel is between about $0.1\times10^6$ cells/$cm^2$ and about $2\times10^6$ cells/$cm^2$, between about $0.1\times10^6$ cells/$cm^2$ and about $1\times10^6$ cells/$cm^2$, between about $0.1\times10^6$ cells/$cm^2$ and about $0.8\times10^6$ cells/$cm^2$, between about $0.1\times10^6$ cells/$cm^2$ and about $0.6\times10^6$ cells/$cm^2$, between about $0.1\times10^6$ cells/$cm^2$ and about $0.4\times10^6$ cells/$cm^2$, between about $0.1\times10^6$ cells/$cm^2$ and about $0.2\times10^6$ cells/$cm^2$, between about $0.2\times10^6$ cells/$cm^2$ and about $2\times10^6$ cells/$cm^2$, between about $0.2\times10^6$ cells/$cm^2$ and about $1\times10^6$ cells/$cm^2$, between about $0.2\times10^6$ cells/$cm^2$ and about $0.8\times10^6$ cells/$cm^2$, between about $0.2\times10^6$ cells/$cm^2$ and about $0.6\times10^6$ cells/$cm^2$, between about $0.2\times10^6$ cells/$cm^2$ and about $0.4\times10^6$ cells/$cm^2$, between about $0.4\times10^6$ cells/$cm^2$ and about $2\times10^6$ cells/$cm^2$, between about $0.4\times10^6$ cells/$cm^2$ and about $1\times10^6$ cells/$cm^2$, between about $0.4\times10^6$ cells/$cm^2$ and about $0.8\times10^6$ cells/$cm^2$, between about $0.4\times10^6$ cells/$cm^2$ and about $0.6\times10^6$ cells/$cm^2$, between about $0.6\times10^6$ cells/$cm^2$ and about $2\times10^6$ cells/$cm^2$, between about $0.6\times10^6$ cells/$cm^2$ and about $1\times10^6$ cells/$cm^2$, between about $0.6\times10^6$ cells/$cm^2$ and about $0.8\times10^6$ cells/$cm^2$, between about $0.8\times10^6$ cells/$cm^2$ and about $2\times10^6$ cells/$cm^2$, between about $0.8\times10^6$ cells/$cm^2$ and about $1\times10^6$ cells/$cm^2$, or between about $1.0\times10^6$ cells/$cm^2$ and about $2\times10^6$ cells/$cm^2$. In some embodiments, the number of cells plated on the substrate-coated culture vessel is between about $0.4\times10^6$ cells/$cm^2$ and about $0.8\times10^6$ cells/$cm^2$.

In some embodiments, the second incubation is from about day 7 until harvesting of the cells. In some embodiments, the cells are harvested on about day 16 or later. In some embodiments, the cells are harvested between about day 16 and about day 30. In some embodiments, the cells are harvested between about day 18 and about day 25. In some embodiments, the cells are harvested on about day 18. In some embodiments, the cells are harvested on about day 25. In some embodiments, the second incubation is from about day 7 until about day 18. In some embodiments, the second incubation is from about day 7 until about day 25.

In some embodiments, the second incubation involves culturing cells derived from the cell aggregate (e.g., spheroid) in a culture media ("media").

In some embodiments, the second incubation involves culturing the cells in the media from about day 7 until harvest or collection. In some embodiments, cells are cultured in the media to produce determined dopamine (DA) neuron progenitor cells, or dopamine (DA) neurons.

In some embodiments, the media is also supplemented with a serum replacement containing minimal non-human-derived components (e.g., KnockOut® serum replacement). In some embodiments, the media is supplemented with the serum replacement from about day 7 through about day 10. In some embodiments, the media is supplemented with about 2% (v/v) of the serum replacement. In some embodiments, the media is supplemented with about 2% (v/v) of the serum replacement from about day 7 through about day 10.

In some embodiments, the media is further supplemented with small molecules. In some embodiments, the small molecules are selected from among the group consisting of: a Rho-associated protein kinase (ROCK) inhibitor, an inhibitor of bone morphogenetic protein (BMP) signaling, an inhibitor of glycogen synthase kinase 3β (GSK3β) signaling, and combinations thereof.

In some embodiments the media is supplemented with a Rho-associated protein kinase (ROCK) inhibitor on one or more days when cells are passaged. In some embodiments the media is supplemented with a ROCK inhibitor each day that cells are passaged. In some embodiments the media is supplemented with a ROCK inhibitor on day 7, day 16, day 20, or a combination thereof. In some embodiments the media is supplemented with a ROCK inhibitor on day 7. In some embodiments the media is supplemented with a ROCK inhibitor on day 16. In some embodiments the media is supplemented with a ROCK inhibitor on day 20. In some embodiments the media is supplemented with a ROCK inhibitor on day 7 and day 16. In some embodiments the media is supplemented with a ROCK inhibitor on day 16 and day 20. In some embodiments the media is supplemented with a ROCK inhibitor on day 7, day 16, and day 20.

In some embodiments, cells are exposed to the ROCK inhibitor at a concentration of between about 1 μM and about 20 μM, between about 5 μM and about 15 M, or between about 8 μM and about 12 μM. In some embodiments, cells are exposed to the ROCK inhibitor at a concentration of between about 1 μM and about 20 μM. In some embodiments, cells are exposed to the ROCK inhibitor at a concentration of between about 5 μM and about 15 μM. In some embodiments, cells are exposed to the ROCK inhibitor at a concentration of between about 8 UM and about 12 μM. In some embodiments, cells are exposed to the ROCK inhibitor at a concentration of about 10 μM.

In some embodiments, the ROCK inhibitor is fasudil, ripasudil, netarsudil, RKI-1447, Y-27632, GSK429286A, Y-30141, or a combination thereof. In some embodiments, the ROCK inhibitor is a small molecule. In some embodiments, the ROCK inhibitor selectively inhibits p160ROCK. In some embodiments, the ROCK inhibitor is Y-27632, having the formula:

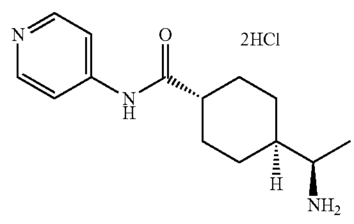 [SMILES: C[C@@H](N)[C@H]1CC[C@H](C(=O)Nc2ccncc2)CC1]

In some embodiments, cells are exposed to Y-27632 at a concentration of about 10 μM. In some embodiments, cells are exposed to Y-27632 at a concentration of about 10 μM on day 7, day 16, day 20, or a combination thereof. In some embodiments, cells are exposed to Y-27632 at a concentration of about 10 μM on day 7. In some embodiments, cells are exposed to Y-27632 at a concentration of about 10 μM on day 16. In some embodiments, cells are exposed to Y-27632 at a concentration of about 10 μM on day 20. In some embodiments, cells are exposed to Y-27632 at a concentration of about 10 μM on day 7 and day 16. In some embodiments, cells are exposed to Y-27632 at a concentration of about 10 μM on day 16 and day 20. In some embodiments, cells are exposed to Y-27632 at a concentration of about 10 μM on day 7, day 16, and day 20.

In some embodiments the media is supplemented with an inhibitor of BMP signaling. In some embodiments the media is supplemented with an inhibitor of BMP signaling from about day 7 up to about day 11 (e.g., day 10 or day 11). In some embodiments the media is supplemented with an inhibitor of BMP signaling from about day 7 through day 10, each day inclusive.

In some embodiments, cells are exposed to the inhibitor of BMP signaling at a concentration of between about 0.01 UM and about 5 μM, between about 0.05 UM and about 1 HM, or between about 0.1 μM and about 0.5 μM, each inclusive. In some embodiments, cells are exposed to the inhibitor of BMP signaling at a concentration of between about 0.01 μM and about 5 μM. In some embodiments, cells are exposed to the inhibitor of BMP signaling at a concentration of between about 0.05 UM and about 1 μM. In some embodiments, cells are exposed to the inhibitor of BMP signaling at a concentration of between about 0.1 μM and about 0.5 μM. In some embodiments, cells are exposed to the inhibitor of BMP signaling at a concentration of about 0.1 μM.

In some embodiments, the inhibitor of BMP signaling is a small molecule. In some embodiments, the inhibitor of BMP signaling is LDN193189 or K02288. In some embodiments, the inhibitor of BMP signaling is capable of inhibiting "Small Mothers Against Decapentaplegic" SMAD signaling. In In some embodiments, the inhibitor of BMP signaling inhibits ALK1, ALK2, ALK3, ALK6, or combinations thereof. In some embodiments, the inhibitor of BMP signaling inhibits ALK1, ALK2, ALK3, and ALK6. In some embodiments, the inhibitor of BMP signaling inhibits BMP2, BMP4, BMP6, BMP7, and activin cytokine signals and subsequently SMAD phosphorylation of Smad1, Smad5, and Smad8. In some embodiments, the inhibitor of BMP signaling is LDN193189. In some embodiments, the inhibitor of BMP signaling is LDN193189 (e.g., IUPAC name 4-(6-(4-(piperazin-1-yl)phenyl) pyrazolo[1,5-a]pyrimidin-3-yl) quinoline, with a chemical formula of $C_{25}H_{22}N_6$), having the formula:

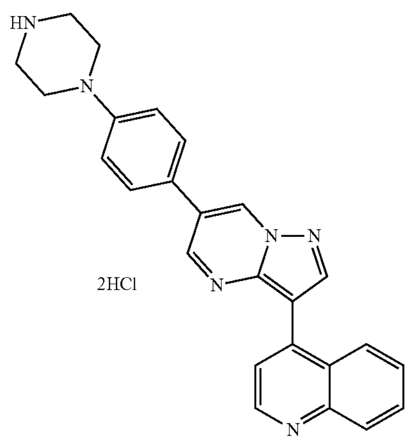 [SMILES: c1ccc2c(-c3cnn4cc(-c5ccc(N6CCNCC6)cc5)cnc34)ccnc2c1]

In some embodiments, cells are exposed to LDN193189 at a concentration of about 0.1 μM. In some embodiments, cells are exposed to LDN193189 at a concentration of about 0.1 μM from about day 7 up to about day 11 (e.g., day 10 or day 11). In some embodiments, cells are exposed to LDN193189 at a concentration of about 0.1 μM from about day 7 through about day 10, inclusive of each day.

In some embodiments the media is supplemented with an inhibitor of GSK3B signaling. In some embodiments the media is supplemented with an inhibitor of GSK3β signaling from about day 7 up to about day 13 (e.g., day 12 or day 13). In some embodiments the media is supplemented with an inhibitor of GSK3β signaling from about day 7 through day 12, each day inclusive.

In some embodiments, cells are exposed to the inhibitor of GSK3β signaling at a concentration of between about 0.1 μM and about 10 μM, between about 0.5 μM and about 8 μM, or between about 1 μM and about 4 μM, or between about 2 μM and about 3 μM, each inclusive. In some embodiments, cells are exposed to the inhibitor of GSK3β signaling at a concentration of between about 0.1 μM and about 10 μM. In some embodiments, cells are exposed to the inhibitor of GSK3β signaling at a concentration of between about 0.5 M and about 8 μM. In some embodiments, cells are exposed to the inhibitor of GSK3β signaling at a concentration of between about 1 μM and about 4 μM. In some embodiments, cells are exposed to the inhibitor of GSK3B signaling at a concentration of between about 2 μM and about 3 μM. In some embodiments, cells are exposed to the inhibitor of GSK3β signaling at a concentration of about 2 μM.

In some embodiments, the inhibitor of GSK3β signaling is selected from lithium ion, valproic acid, iodotubercidin, naproxen, famotidine, curcumin, olanzapine, CHIR99012, or a combination thereof. In some embodiments, the inhibitor of GSK3β signaling is a small molecule. In some embodiments, the inhibitor of GSK3β signaling inhibits a glycogen synthase kinase 3β enzyme. In some embodiments, the inhibitor of GSK3β signaling inhibits GSK3a. In some embodiments, the inhibitor of GSK3β signaling modulates TGF-β and MAPK signaling. In some embodiments, the inhibitor of GSK3β signaling is an agonist of wingless/integrated (Wnt) signaling. In some embodiments, the inhibitor of GSK3β signaling has an IC50-6.7 nM against human GSK3β. In some embodiments, the inhibitor of GSK3β signaling is CHIR99021 (e.g., "3-[3-(2-Carboxyethyl)-4-methylpyrrol-2-methylidenyl]-2-indolinone" or IUPAC name 6-(2-(4-(2,4-dichlorophenyl)-5-(4-methyl-1H-imidazol-2-yl)pyrimidin-2-ylamino)ethylamino)nicotinonitrile), having the formula:

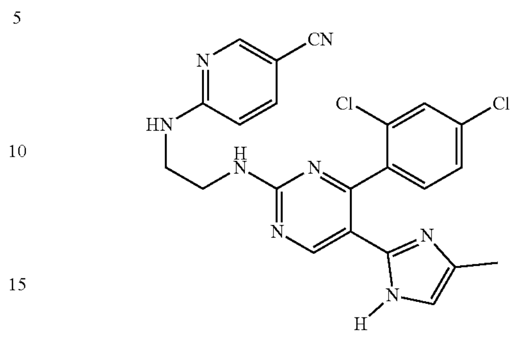

In some embodiments, cells are exposed to CHIR99021 at a concentration of about 2.0 μM. In some embodiments, cells are exposed to CHIR99021 at a concentration of about 2.0 μM from about day 7 up to about day 13 (e.g., day 12 or day 13). In some embodiments, cells are exposed to CHIR99021 at a concentration of about 2.0 M from about day 7 through about day 12, inclusive of each day.

In some embodiments the media is supplemented with brain-derived neurotrophic factor (BDNF). In some embodiments the media is supplemented with BDNF beginning on about day 11. In some embodiments the media is supplemented with BDNF from about day 11 until harvest or collection. In some embodiments the media is supplemented with BDNF from about day 11 through day 18. In some embodiments the media is supplemented with BDNF from about day 11 through day 25.

In some embodiments, cells are exposed to BDNF at a concentration of between about 1 ng/mL and 100 ng/mL, between about 5 ng/mL and about 50 ng/ml, between about 10 ng/ml and about 30 ng/mL. In some embodiments, cells are exposed to BDNF at a concentration of between about 10 ng/mL and about 30 ng/mL. In some embodiments, cells are exposed to BDNF at a concentration of about 20 ng/ml.

In some embodiments, the media is supplemented with about 20 ng/ml BDNF beginning on about day 11. In some embodiments the media is supplemented with 20 ng/ml BDNF from about day 11 until harvest or collection. In some embodiments the media is supplemented with about 20 ng/mL BDNF from about day 11 through day 18. In some embodiments the media is supplemented with about 20 ng/mL BDNF from about day 11 through day 25.

In some embodiments the media is supplemented with glial cell-derived neurotrophic factor (GDNF). In some embodiments the media is supplemented with GDNF beginning on about day 11. In some embodiments the media is supplemented with GDNF from about day 11 until harvest or collection. In some embodiments the media is supplemented with GDNF from about day 11 through day 18. In some embodiments the media is supplemented with GDNF from about day 11 through day 25.

In some embodiments, cells are exposed to GDNF at a concentration of between about 1 ng/ml and 100 ng/mL, between about 5 ng/ml and about 50 ng/ml, between about 10 ng/ml and about 30 ng/mL. In some embodiments, cells are exposed to GDNF at a concentration of between about 10 ng/mL and about 30 ng/mL. In some embodiments, cells are exposed to GDNF at a concentration of about 20 ng/mL.

In some embodiments, the media is supplemented with about 20 ng/mL GDNF beginning on about day 11. In some embodiments the media is supplemented with 20 ng/ml GDNF from about day 11 until harvest or collection. In some embodiments the media is supplemented with about 20 ng/ml GDNF from about day 11 through day 18. In some embodiments the media is supplemented with about 20 ng/ml GDNF from about day 11 through day 25.

In some embodiments the media is supplemented with ascorbic acid. In some embodiments the media is supplemented with ascorbic acid beginning on about day 11. In some embodiments the media is supplemented with ascorbic acid from about day 11 until harvest or collection. In some embodiments the media is supplemented with ascorbic acid from about day 11 through day 18. In some embodiments the media is supplemented with ascorbic acid from about day 11 through day 25.

In some embodiments, cells are exposed to ascorbic acid at a concentration of between about 0.05 mM and 5 mM, between about 0.1 mM and about 1 mM, between about 0.2 mM and about 0.5 mM, each inclusive. In some embodiments, cells are exposed to ascorbic acid at a concentration of between about 0.05 mM and about 5 mM, each inclusive. In some embodiments, cells are exposed to ascorbic acid at a concentration of between about 0.1 mM and about 1 mM, each inclusive. In some embodiments, cells are exposed to ascorbic acid at a concentration of about 0.2 mM.

In some embodiments, the media is supplemented with about 0.2 mM ascorbic acid beginning on about day 11. In some embodiments the media is supplemented with 0.2 mM ascorbic acid from about day 11 until harvest or collection. In some embodiments the media is supplemented with about 0.2 mM ascorbic acid from about day 11 through day 18. In some embodiments the media is supplemented with about 0.2 mM ascorbic acid from about day 11 through day 25.

In some embodiments the media is supplemented with dibutyryl cyclic AMP (dbcAMP). In some embodiments the media is supplemented with dbcAMP beginning on about day 11. In some embodiments the media is supplemented with dbcAMP from about day 11 until harvest or collection. In some embodiments the media is supplemented with dbcAMP from about day 11 through day 18. In some embodiments the media is supplemented with dbcAMP from about day 11 through day 25.

In some embodiments, cells are exposed to dbcAMP at a concentration of between about 0.05 mM and 5 mM, between about 0.1 mM and about 3 mM, between about 0.2 mM and about 1 mM, each inclusive. In some embodiments, cells are exposed to dbcAMP at a concentration of between about 0.1 mM and about 3 mM, each inclusive. In some embodiments, cells are exposed to dbcAMP at a concentration of between about 0.2 mM and about 1 mM, each inclusive. In some embodiments, cells are exposed to dbcAMP at a concentration of about 0.5 mM.

In some embodiments, the media is supplemented with about 0.5 mM dbcAMP beginning on about day 11. In some embodiments the media is supplemented with 0.5 mM dbcAMP from about day 11 until harvest or collection. In some embodiments the media is supplemented with about 0.5 mM dbcAMP from about day 11 through day 18. In some embodiments the media is supplemented with about 0.5 mM dbcAMP from about day 11 through day 25.

In some embodiments the media is supplemented with transforming growth factor beta 3 (TGFβ3). In some embodiments the media is supplemented with TGFβ3 beginning on about day 11. In some embodiments the media is supplemented with TGFβ3 from about day 11 until harvest or collection. In some embodiments the media is supplemented with TGFβ3 from about day 11 through day 18. In some embodiments the media is supplemented with TGFβ3 from about day 11 through day 25.

In some embodiments, cells are exposed to TGFβ3 at a concentration of between about 0.1 ng/ml and 10 ng/mL, between about 0.5 ng/mL and about 5 ng/mL, or between about 1.0 ng/ml and about 2.0 ng/mL. In some embodiments, cells are exposed to TGFβ3 at a concentration of between about 1.0 ng/ml and about 2.0 ng/ml, each inclusive. In some embodiments, cells are exposed to TGFβ3 at a concentration of about 1 ng/mL.

In some embodiments, the media is supplemented with about 1 ng/ml TGFβ3 beginning on about day 11. In some embodiments the media is supplemented with 1 ng/ml TGFβ3 from about day 11 until harvest or collection. In some embodiments the media is supplemented with about 1 ng/ml TGFβ3 from about day 11 through day 18. In some embodiments the media is supplemented with about 1 ng/mL TGFβ3 from about day 11 through day 25.

In some embodiments the media is supplemented with an inhibitor of Notch signaling. In some embodiments the media is supplemented with an inhibitor of Notch signaling beginning on about day 11. In some embodiments the media is supplemented with an inhibitor of Notch signaling from about day 11 until harvest or collection. In some embodiments the media is supplemented with an inhibitor of Notch signaling from about day 11 through day 18. In some embodiments the media is supplemented with an inhibitor of Notch signaling from about day 11 through day 25.

In some embodiments, an inhibitor of Notch signaling is selected from cowanin, PF-03084014, L685458, LY3039478, DAPT, or a combination thereof. In some embodiments, the inhibitor of Notch signaling inhibits gamma secretase. In some embodiments, the inhibitor of Notch signaling is a small molecule. In some embodiments, the inhibitor of Notch signaling is DAPT, having the following formula:

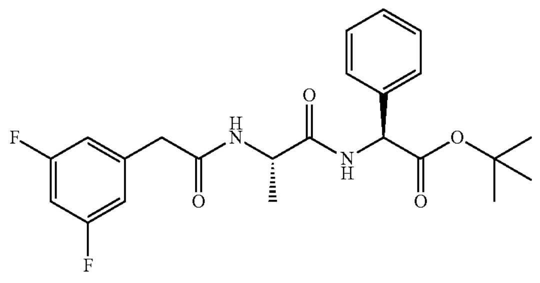 [SMILES: C[C@H](NC(=O)Cc1cc(F)cc(F)c1)C(=O)N[C@H](C(=O)OC(C)(C)C)c1ccccc1]

In some embodiments, cells are exposed to DAPT at a concentration of between about 1 μM and about 20 μM, between about 5 μM and about 15 μM, or between about 8 μM and about 12 M. In some embodiments, cells are exposed to DAPT at a concentration of between about 1 μM and about 20 μM. In some embodiments, cells are exposed to DAPT at a concentration of between about 5 M and about 15 μM. In some embodiments, cells are exposed to DAPT at a concentration of between about 8 μM and about 12 μM. In some embodiments, cells are exposed to DAPT at a concentration of about 10 μM.

In some embodiments, the media is supplemented with about 10 μM DAPT beginning on about day 11. In some embodiments the media is supplemented with 10 μM DAPT from about day 11 until harvest or collection. In some embodiments the media is supplemented with about 10 μM DAPT from about day 11 through day 18. In some embodiments the media is supplemented with about 10 μM DAPT from about day 11 through day 25.

In some embodiments, beginning on about day 11, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAPT. In some embodiments, from about day 11 until harvest or collection, the media is supplemented with about 20 ng/mL BDNF, about 20 ng/mL GDNF, about 0.2 mM ascorbic acid, about 0.5 mM dbcAMP, about 1 ng/ml TGFβ3, and about 10 μM DAPT. In some embodiments, from about day 11 until day 18, the media is supplemented with about 20 ng/mL BDNF, about 20 ng/ml GDNF, about 0.2 mM ascorbic acid, about 0.5 mM dbcAMP, about 1 ng/mL TGFβ3, and about 10 μM DAPT. In some embodiments, from about day 11 until day 25, the media is supplemented with about 20 ng/ml BDNF, about 20 ng/mL GDNF, about 0.2 mM ascorbic acid, about 0.5 mM dbcAMP, about 1 ng/mL TGFβ3, and about 10 μM DAPT.

In some embodiments, a serum replacement is provided in the media from about day 7 through about day 10. In some embodiments, the serum replacement is provided at 2% (v/v) in the media on day 7 through day 10.

In some embodiments, from day about 7 to about day 16, at least about 50% of the media is replaced daily. In some embodiments, from about day 7 to about day 16, about 50% of the media is replaced daily, every other day, or every third day. In some embodiments, from about day 7 to about day 16, about 50% of the media is replaced daily. In some embodiments, beginning on about day 17, at least about 50% of the media is replaced daily, every other day, or every third day. In some embodiments, beginning on about day 17, at least about 50% of the media is replaced every other day. In some embodiments, beginning on about day 17, about 50% of the media is replaced daily, every other day, or every third day. In some embodiments, beginning on about day 17, about 50% of the media is replaced every other day. In some embodiments, the replacement media contains small molecules about twice as concentrated as compared to the concentration of the small molecules in the media on day 0.

In some embodiments, the second incubation involves culturing cells derived from the cell aggregate (e.g., spheroid) in a "basal induction media." In some embodiments, the second incubation involves culturing cells derived from the cell aggregate (e.g., spheroid) in a "maturation media." In some embodiments, the second incubation involves culturing cells derived from the cell aggregate (e.g., spheroid) in the basal induction media, and then in the maturation media.

In some embodiments, the second incubation involves culturing the cells in the basal induction media from about day 7 through about day 10. In some embodiments, the second incubation involves comprises culturing the cells in the maturation media beginning on about day 11. In some embodiments, the second incubation involves culturing the cells in the basal induction media from about day 7 through about day 10, and then in the maturation media beginning on about day 11. In some embodiments, cells are cultured in the maturation media to produce determined dopamine (DA) neuron progenitor cells, or dopamine (DA) neurons.

In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, the basal induction media is further supplemented with any of the molecules described in Section II.

In some embodiments, the maturation media is formulated to contain Neurobasal™ media, supplemented with N-2 and B27 supplements, non-essential amino acids (NEAA), and GlutaMAX™. In some embodiments, the maturation media is further supplemented with any of the molecules described in Section II.

In some embodiments, the cells are cultured in the basal induction media from about day 7 up to about day 11 (e.g., day 10 or day 11). In some embodiments, the cells are cultured in the basal induction media from about day 7 through day 10, each day inclusive. In some embodiments, the cells are cultured in the maturation media beginning on about day 11. In some embodiments, the cells are cultured in the basal induction media from about day 7 through about day 10, and then the cells are cultured in the maturation media beginning on about day 11. In some embodiments, the cells are cultured in the maturation media from about day 11 until harvest or collection of the cells. In some embodiments, cells are harvested between day 16 and 27. In some embodiments, cells are harvested between day 18 and day 25. In some embodiments, cells are harvested on day 18. In some embodiments, cells are harvested on day 25.

E. Harvesting, Collecting, and Formulating Differentiated Cells

In embodiments of the provided methods, neutrally differentiated cells produced by the methods provided herein can be harvested or collected, such as for formulation and use of the cells. In some embodiments, the provided methods for producing differentiated cells, such as for use as a cell therapy in the treatment of a neurodegenerative disease may include formulation of cells, such as formulation of differentiated cells resulting from the provided methods described herein. In some embodiments, the dose of cells comprising differentiated cells (e.g., determined DA neuron progenitor cells or DA neurons), is provided as a composition or formulation, such as a pharmaceutical composition or formulation. Such compositions can be used in accord with the provided methods, such as in the prevention or treatment of neurodegenerative disorders, including Parkinson's disease.

In some cases, the cells are processed in one or more steps for manufacturing, generating or producing a cell therapy and/or differentiated cells may include formulation of cells, such as formulation of differentiated cells resulting from the methods. In some cases, the cells can be formulated in an amount for dosage administration, such as for a single unit dosage administration or multiple dosage administration.

In certain embodiments, one or more compositions of differentiated cells are formulated. In particular embodiments, one or more compositions of differentiated cells are formulated after the one or more compositions have been produced. In some embodiments, the one or more compositions have been previously cryopreserved and stored, and are thawed prior to the administration.

In certain embodiments, the differentiated cells include determined DA neuron progenitor cells. In some embodiments, a formulated composition of differentiated cells is a composition enriched for determined DA neuron progenitor cells. In certain embodiments, the differentiated cells include DA neurons. In some embodiments, a formulated composition of differentiated cells is a composition enriched for DA neurons.

In certain embodiments, the cells are cultured for a minimum or maximum duration or amount of time. In certain embodiments, the cells are cultured for a minimum duration or amount of time. In certain embodiments, the cells are cultured for a maximum duration or amount of time. In some embodiments, the cells are differentiated for at least 16 days. In some embodiments, the cells are differentiated for between 16 day and 30 days. In some embodiments, the cells are differentiated for between 16 day and 27 days. In some embodiments, the cells are differentiated for between 18 and 25 days. In some embodiments, the cells are differentiated for about 18 days. In some embodiments, the cells are differentiated for about 25 days.

In certain embodiments, the cells are cultured for a minimum or maximum duration or amount of time. In certain embodiments, the cells are cultured for a minimum duration or amount of time. In certain embodiments, the cells are cultured for a maximum duration or amount of time. In some embodiments, the cells are harvested after at least 16 days of culture. In some embodiments, the cells are harvested between 16 days and 30 days of culture. In some embodiments, the cells are harvested between 16 days and 27 days of culture. In some embodiments, the cells are harvested between 18 days and 25 days of culture. In some embodiments, the cells are harvested after about 18 days of culture. In some embodiments, the cells are harvested after about 25 days of culture.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the differentiated cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the neurodegenerative condition or disease (e.g., Parkinson's disease), such as a therapeutically effective or prophylactically effective amount.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservatives or mixtures thereof are typically present in an amount of about 0.0001% to about 2% by weight of the total composition. Carriers are described, e.g., by *Remington's Pharmaceutical Sciences* 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, *Remington: The Science and Practice of Pharmacy*, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as carbidopa-levodopa (e.g., Levodopa), dopamine agonists (e.g., pramipexole, ropinirole, rotigotine, and apomorphine), MAO B inhibitors (e.g., selegiline, rasagiline, and safinamide), catechol O-methyltransferase (COMT) inhibitors (e.g., entacapone and tolcapone), anticholinergics (e.g., benztropine and trihexylphenidyl), amantadine, etc.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cells are formulated with a cryopreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the differentiated cells to replace the cells in a cryopreservative solution. In some embodiments, the cells are frozen, e.g., cryopreserved or cryoprotected, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryopreserved or cryoprotected, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of differentiated cells are formulated, cryopreserved, and then stored for an amount of time. In certain embodiments, the formulated, cryopreserved cells are stored until the cells are released for administration. In particular embodiments, the formulated cryopreserved cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryopreserved and stored for, for about, or for less than 1 days, 2 days, 3 days, 4 days, 5 days, 6 days, or 7 days. In certain embodiments, the cells are thawed and administered to a subject after the storage.

In some embodiments, the formulation is carried out using one or more processing step including washing, diluting or concentrating the cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to differentiated cells. In some embodiments, the volume of formulation buffer is from or from about 1 μL to 5000 μL, such as at least or about at least or about or 5 μL, 10 μL, 20 μL, 50 μL, 100 μL, 200 μL, 300 μL, 400 μL, 500 μL, 1000 μL, 2000 μL, 3000 μL, 4000 μL, or 5000 μL.

A container may generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, such cells produced by the method, or a composition comprising such cells, are administered to a subject for treating a neurodegenerative disease or condition.

F. Exemplary Processes

As described by the methods provided herein, pluripotent stem cells may be differentiated into lineage specific cell populations, including determined DA progenitor cells and DA neurons. These cells may then be used in cell replacement therapy. As described by the methods here, in some embodiments, the pluripotent stem cells are differentiated into floor plate midbrain progenitor cells, and the resulting spheroid cells are further differentiated into determined dopamine (DA) neuron progenitor cells, and/or dopamine (DA) neurons. In some embodiments, the pluripotent stem cells are differentiated into determined DA neuron progenitor cells. In some embodiments, the pluripotent stem cells are differentiated into DA neurons. In some embodiments, pluripotent stem cells are embryonic stem cells. In some embodiments, pluripotent stem cells are induced pluripotent stem cells.

In some embodiments, embryonic stem cells are differentiated into floor plate midbrain progenitor cells, and then into determined dopamine (DA) neuron progenitor cells, and/or dopamine (DA) neurons. In some embodiments, embryonic stem cells are differentiated into determined DA neuron progenitor cells. In some embodiments, embryonic stem cells are differentiated into DA neurons.

In some embodiments, induced pluripotent stem cells are differentiated into floor plate midbrain progenitor cells, and then into determined dopamine (DA) neuron progenitor cells, and/or dopamine (DA) neurons. In some embodiments, induced pluripotent stem cells are differentiated into determined DA neuron progenitor cells. In some embodiments, induced pluripotent stem cells are differentiated into DA neurons.

In some embodiments, the method involves (a) performing a first incubation including culturing pluripotent stem cells in a non-adherent culture vessel under conditions to produce a cellular spheroid, wherein beginning at the initiation of the first incubation (day 0) the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3β (GSK3β) signaling; and (b) performing a second incubation including culturing cells of the spheroid in a substrate-coated culture vessel under conditions to induce neural differentiation the cells.

In some embodiments, culturing the cells under conditions to induce neural differentiation of the cells involves exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling.

In some embodiments, the method involves (a) performing a first incubation including culturing pluripotent stem cells in a plate having microwells under conditions to produce a cellular spheroid, wherein beginning at the initiation of the first incubation (day 0) the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; (iv) an inhibitor of glycogen synthase kinase 3β (GSK3β) signaling; and (v) a serum replacement; (b) dissociating the cells of the spheroid to produce a cell suspension; (c) transferring cells of the cell suspension to a laminin-coated culture vessel; (d) performing a second incubation including culturing cells of the spheroid in the laminin-coated culture vessel under conditions to induce neural differentiation of the cells; and (c) harvesting the neurally differentiated cells. In some embodiments, the second incubation involves culturing cells in the presence of a serum replacement. In some embodiments, culturing the cells under conditions to induce neural differentiation of the cells involves exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling.

In some embodiments, the cells are exposed to the inhibitor of TGF-β/activin-Nodal (e.g., SB431542 or "SB") from day 0 up to about day 7 (e.g., day 6 or day 7). In some embodiments, the cells are exposed to the inhibitor of TGF-β/activin-Nodal (e.g., SB431542 or "SB") from day 0 through day 6, inclusive of each day. In some embodiments, the cells are exposed to the at least one activator of SHH signaling (e.g., SHH protein and purmorphamine, collectively "SHH/PUR") from day 0 up to about day 7 (e.g., day 6 or day 7). In some embodiments, the cells are exposed to the at least one activator of SHH signaling (e.g., SHH protein and purmorphamine, collectively "SHH/PUR") from day 0 through day 6, inclusive of each day. In some embodiments, the cells are exposed to the inhibitor of BMP signaling (e.g., LDN193189 or "LDN") from day 0 up to about day 11 (e.g., day 10 or day 11). In some embodiments, the cells are exposed to the inhibitor of BMP signaling (e.g., LDN193189 or "LDN") from day 0 through day 10, inclusive of each day. In some embodiments, the cells are exposed to the inhibitor of GSK3 signaling (e.g., CHIR99021 or "CHIR") from day 0 up to about day 13 (e.g., day 12 or day 13). In some embodiments, the cells are exposed to the inhibitor of GSK3B signaling (e.g., CHIR99021 or "CHIR") from day 0 through day 12.

In some embodiments, the cells are exposed to (i) an inhibitor of TGF-β/activin-Nodal signaling from day 0 up to about day 7 (e.g., day 6 or day 7); (ii) at least one activator of Sonic Hedgehog (SHH) signaling from day 0 up to about day 7 (e.g., day 6 or day 7); (iii) an inhibitor of bone morphogenetic protein (BMP) signaling from day 0 up to about day 11 (e.g., day 10 or day 11); and (iv) an inhibitor of glycogen synthase kinase 3β (GSK3β) signaling from day 0 up to about day 13 (e.g., day 12 or day 13). In some embodiments, the cells are exposed to (i) SB from day 0 up to about day 7 (e.g., day 6 or day 7); (ii) SHH/PUR from day 0 up to about day 7 (e.g., day 6 or day 8); (iii) LDN from day 0 up to about day 11 (e.g., day 10 or day 11); and (iv) CHIR from day 0 up to about day 13 (e.g., day 12 or day 13). In some embodiments, the cells are exposed to (i) an inhibitor of TGF-β/activin-Nodal signaling from day 0 through day 6, each day inclusive; (ii) at least one activator of Sonic Hedgehog (SHH) signaling from day 0 through day 6, each day inclusive; (iii) an inhibitor of bone morphogenetic protein (BMP) signaling from day 0 through day 10, each day inclusive; and (iv) an inhibitor of glycogen synthase kinase 3β (GSK3β) signaling from day 0 through day 12, each day inclusive. In some embodiments, the cells are exposed to (i) SB from day 0 through day 6, each day inclusive; (ii) SHH/PUR from day 0 through day 6, each day inclusive; (iii) LDN from day 0 through day 10, each day inclusive; and (iv) CHIR from day 0 through day 12, each day inclusive.

In some embodiments, the cells are exposed to brain-derived neurotrophic factor (BDNF) beginning on day 11. In some embodiments, the cells are exposed to ascorbic acid. In some embodiments, the cells are exposed to glial cell-derived neurotrophic factor (GDNF) beginning on day 11. In some embodiments, the cells are exposed to dibutyryl cyclic AMP (dbcAMP) beginning on day 11. In some embodiments, the cells are exposed to transforming growth factor beta-3 (TGFβ3) beginning on day 11. In some embodiments, the cells are exposed to the inhibitor of Notch signaling (e.g., DAPT) beginning on day 11. In some embodiments, beginning on day 11, the cells are exposed to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) the inhibitor of Notch signaling (e.g., DAPT) (collectively "BAGCT/DAPT"). In some embodiments, the cells are exposed to BAGCT/DAPT beginning on day 11 until harvest or collection. In some embodiments, the cells are exposed to BAGCT/DAPT from day 11 through day 18. In some embodiments, the cells are exposed to BAGCT/DAPT from day 11 through day 25.

In some embodiments, the cells are exposed to a Rho-associated protein kinase (ROCK) inhibitor on day 0. In some embodiments, the cells are exposed to a Rho-associated protein kinase (ROCK) inhibitor on day 7. In some embodiments, the cells are exposed to a Rho-associated protein kinase (ROCK) inhibitor on day 16. In some embodiments, the cells are exposed to a Rho-associated protein kinase (ROCK) inhibitor on day 20. In some embodiments, the cells are exposed to a Rho-associated protein kinase (ROCK) inhibitor on day 0, day 7, day 16, and day 20. In some embodiments, the cells are exposed to a ROCK inhibitor on the day on which the cells are passaged. In some embodiments, the cells are passaged on day 0, 7, 16, 20, or combinations thereof. In some embodiments, the cells are passaged on day 0, 7, 16, and 20.

In some embodiments, the cells are cultured in a basal induction medium comprising DMEM/F-12 and Neurobasal media (e.g., at a 1:1 ratio), supplemented with N2, B27, non-essential amino acids (NEAA), GlutaMAX™, L-glutamine, β-mercaptocthanol, and insulin. In some embodiments, the cells are cultured in the basal induction media from about day 0 through about day 10. In some embodiments, the basal induction media is for differentiating pluripotent stem cells into floor plate midbrain progenitor cells.

In some embodiments, the cells are cultured in a maturation medium comprising Neurobasal™ media, supplemented with N2, B27, non-essential amino acids (NEAA), and GlutaMAX™. In some embodiments, the cells are cultured in the basal induction media from about day 11 until harvest or collection. In some embodiments, the cells are cultured in the basal induction media from about day 11 through day 18. In some embodiments, the maturation media is for differentiating floor plate midbrain progenitor cells into determined dopamine (DA) neuron progenitor cells. In some embodiments, the cells are cultured in the basal induction media from about day 11 through day 25. In some embodiments, the maturation media is for differentiating floor plate midbrain progenitor cells into dopamine (DA) neurons.

In some embodiments, the media is supplemented with small molecules as described above, including SB, SHH/PUR, LDN, CHIR, BAGCT/DAPT, and ROCKi. In some embodiments, the media is changed every day or every other day. In some embodiments the media is changed every day.

In some embodiments the media is changed every other day. In some embodiments, the media is changed every day from about day 0 up to about day 17 (e.g., day 16 or day 18). In some embodiments, the media is changed every other day from about day 18 until harvest or collection. In some embodiments, the media is changed every day from about day 0 up to about day 17 (e.g., day 16 or day 18), and then every other day from about day 18 until harvest or collection.

In some embodiments, a serum replacement is provided in the media from about day 0 up to about day 10 (e.g., day 9 or day 11). In some embodiments, the serum replacement is provided at 5% (v/v) in the media on day 0 and day 1. In some embodiments, the serum replacement is provided at 2% (v/v) in the media on day 2 through day 10. In some embodiments, the serum replacement is provided at 5% (v/v) in the media on day 0 and day 1 and at 2% (v/v) in the media on day 2 through day 10. In some embodiments, serum replacement is not provided in the media after day 10.

In some embodiments, at least about 50% or at least about 75% of the media is changed. In some embodiments, at least about 50% of the media is changed. In some embodiments, at least about 75% of the media is changed. In some embodiments about 100% of the media is changed.

In some embodiments, about 50% or about 75% of the media is changed. In some embodiments, about 50% of the media is changed. In some embodiments, about 75% of the media is changed. In some embodiments about 100% of the media is changed.

In some embodiments, the media is supplemented with small molecules selected from SB, SHH/PUR, LDN, CHIR, BAGCT/DAPT, ROCKi, or a combination thereof. In some embodiments, when about 50% of the media is changed, the concentration of each small molecule is doubled as compared to its concentration on day 0.

In some embodiments, cells are harvested between about day 16 and about day 30. In some embodiments, cells are harvested between about day 16 and about day 27. In some embodiments, cells are harvested between about day 18 and about day 25. In some embodiments, cells are harvested on about day 18. In some embodiments, cells are harvested on about day 25. In some embodiments, the harvested cells are formulated with a cryopreservant, e.g., DMSO. In some embodiments, the harvested cells produced by the method are cryopreserved before use. In some embodiments, such cryopreserved cells are thawed before use or administration to a subject, e.g., a human patient with a neurodegenerative disease or condition, such as Parkinson's disease.

In some embodiments, compositions comprising cells generated by the methods provided herein are used for the treatment of a neurodegenerative disease or condition, such as Parkinson's disease. In some embodiments, a composition of cells generated by any of the methods described herein are administered to a subject who has Parkinson's disease. In some embodiments, a composition of cells generated by any of the methods described herein are administered by stereotactic injection, such as with a catheter. In some embodiments, a composition of cells generated by any of the methods described herein are administered to the striatum of a subject with Parkinson's disease.

III. COMPOSITIONS AND FORMULATIONS

Provided herein are therapeutic compositions containing differentiated cells that are determined dopamine (DA) neuron progenitor cells. Also provided herein are therapeutic compositions containing differentiated cells produced by any of the provided methods, such as any methods described in Section II. In some embodiments, the differentiated cells produced by any of the methods described herein are determined dopamine (DA) neuron progenitor cells.

In some embodiments, the differentiated cells in the provided therapeutic compositions, including those produced by any of the methods described herein, are capable of producing dopamine (DA). In some embodiments, the differentiated cells in the provided therapeutic compositions, including those produced by any of the methods described herein, do not produce or do not substantially produce norepinephrine (NE). Thus, in some embodiments, the differentiated cells in the therapeutic compositions provided herein, including those produced by any of the methods described herein, are capable of producing DA but do not produce or do not substantially produce NE.

In some embodiments, the determined dopamine (DA) neuron progenitor cells express EN1. In some embodiments, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the total cells in the composition express EN1.

In some embodiments, the therapeutic composition exhibits a ratio of counts per million (CPM) EN1 to CPM GAPDH of greater than about $1\times10^{-4}$. In some embodiments, the ratio of CPM EN1 to CPM GAPDH is between about $1.5\times10^{-3}$ and $1\times10^{-2}$.

In some embodiments, the determined dopamine (DA) neuron progenitor cells express CORIN. In some embodiments, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the total cells in the composition express CORIN.

In some embodiments, the therapeutic composition exhibits a ratio of counts per million (CPM) CORIN to CPM GAPDH of greater than about $1\times10^{-4}$. In some embodiments, the ratio of CPM CORIN to CPM GAPDH is between about $5\times10^{-2}$ and $5\times10^{-1}$.

In some embodiments, less than 10% of determined dopamine (DA) neuron progenitor cells express TH. In some embodiments, the determined dopamine (DA) neuron progenitor cells express low levels of TH. In some embodiments, the determined dopamine (DA) neuron progenitor cells do not express TH. In some embodiments, the determined dopamine (DA) neuron progenitor cells express TH at lower levels than cells harvested or collected on other days. In some embodiments, some of the determined dopamine (DA) neuron progenitor cells express EN1 and CORIN and less than 10% of the cells express TH.

In some embodiments, less than 8% of the cells express TH. In some embodiments, less than 5% of the cells express TH. In some embodiments, between about 2% and 10%, between about 2% and 8%, between about 2% and 6%, between about 2% and 4%, between about 4% and 10%, between about 4% and 8%, between about 4% and 6%, between about 6% and 10%, between about 6% and 8%, or between about 8% and 10% of the total cells in the composition express TH.

In some embodiments the therapeutic composition exhibits a ratio of counts per million (CPM) TH to CPM GAPDH of less than about $3\times10^{-2}$. In some embodiments, the ratio of CPM TH to CPM GAPDH is between about $1\times10^{-3}$ and $2.5\times10^{-2}$.

In some embodiments, less than 10% of the total cells in the composition express TH, and at least about 20% of the cells of the therapeutic composition express EN1. In some embodiments, less than 10% of the total cells in the composition express TH, and at least about 25% of the cells of the therapeutic composition express EN1.

In some embodiments, the differentiated cells produced by any of the methods described herein are dopamine (DA) neurons (e.g., midbrain fate DA neurons). In some embodiments, the midbrain fate dopamine (DA) neurons are $FOXA2^+/TH^+$ at the time of harvest. In some embodiments, the midbrain fate dopamine (DA) neurons are $FOXA2^+/TH^+$ by or on about day 18. In some embodiments, the midbrain fate dopamine (DA) neurons are $FOXA2^+/TH^+$ by or on about day 25.

In some embodiments, a therapeutic composition described herein comprises determined dopamine progenitor cells (DDPCs) derived from pluripotent stem cells. In some embodiments, the therapeutic composition produced by any of the methods described herein exhibits one or more of: (a) a ratio of counts per million (CPM) NEUROG1 to CPM GAPDH of greater than about $2\times10^{-5}$; (b) a ratio of EDN3 to CPM GAPDH of greater than about 5×10-+; (c) a ratio of HES1 to CPM GAPDH of greater than about $4\times10^{-3}$; (d) a ratio of PSRC1 to CPM GAPDH of greater than about $8\times10^{-3}$; (c) a ratio of NEK6 to CPM GAPDH of greater than about $2\times10^{-3}$; (f) a ratio of IQGAP3 to CPM GAPDH of greater than about $1\times10^{-2}$; (g) a ratio of USP44 to CPM GAPDH of greater than about 8×10-+; (h) a ratio of CEP55 to CPM GAPDH of greater than about $3\times10^{-3}$; (i) a ratio of KIF20A to CPM GAPDH of greater than about $2\times10^{-2}$; (j) a ratio of AURKA to CPM GAPDH of greater than about $2\times10^{-2}$; (k) a ratio of CALCA to CPM GAPDH of less than about $1\times10^{-3}$; (1) a ratio of GLRA2 to CPM GAPDH of less than about $1\times10^{-3}$; (m) a ratio of MAPT to CPM GAPDH of less than about $1\times10^{-1}$; (n) a ratio of CAMK2B to CPM GAPDH of less than about $5\times10^{-2}$; (o) a ratio of SYT13 to CPM GAPDH of less than about $1\times10^{-2}$; (p) a ratio of LHFPL4 to CPM GAPDH of less than about $1\times10^{-3}$; (q) a ratio of RET to CPM GAPDH of less than about $5\times10^{-3}$; (r) a ratio of KCND3 to CPM GAPDH of less than about $1\times10^{-2}$; (s) a ratio of NSG2 to CPM GAPDH of less than about $5\times10^{-2}$; and (t) a ratio of SNAP25 to CPM GAPDH of less than about $2\times10^{-2}$.

Methods for measuring or assessing gene expression or gene products (including the transcriptional and/or translation products) include those described in Section I. Further, in some embodiments, measuring or assessing gene expression or gene products is or includes assessing, measuring, determining, and/or quantifying a level, amount, or concentration of a gene product (transcription and/or translational) in the sample.

In some embodiments, gene expression is or includes a process by which information of the gene is used in the synthesis of a gene product. Thus, in some embodiments, a gene product is any biomolecule that is assembled, generated, and/or synthesized with information encoded by a gene, and may include polynucleotides and/or polypeptides. In particular embodiments, assessing, measuring, and/or determining gene expression is or includes determining or measuring the level, amount, or concentration of the gene product. In certain embodiments, the level, amount, or concentration of the gene product may be transformed (e.g., normalized) or directly analyzed (e.g., raw).

In some embodiments, the gene product is or includes a protein, i.e., a polypeptide, that is encoded by and/or expressed by the gene. In particular embodiments, the gene product encodes a protein that is localized and/or exposed on the surface of a cell. In some embodiments, the protein is a soluble protein. In certain embodiments, the protein is secreted by a cell. In particular embodiments, the gene expression is the amount, level, and/or concentration of a protein that is encoded by the gene. In certain embodiments, one or more protein gene products are measured by any suitable means known in the art. Suitable methods for assessing, measuring, determining, and/or quantifying the level, amount, or concentration or more or more protein gene products include, but are not limited to detection with immunoassays, nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays). In some embodiments, the immunoassay is or includes methods or assays that detect proteins based on an immunological reaction, e.g., by detecting the binding of an antibody or antigen binding antibody fragment to a gene product. Immunoassays include, but are not limited to, quantitative immunocytochemistry or immunohistochemistry, ELISA (including direct, indirect, sandwich, competitive, multiple and portable ELISAs (see, e.g., U.S. Pat. No. 7,510,687), western blotting (including one, two or higher dimensional blotting or other chromatographic means, optionally including peptide sequencing), enzyme immunoassay (EIA), RIA (radioimmunoassay), and SPR (surface plasmon resonance).

In certain embodiments, the gene product is a polynucleotide, e.g., an mRNA or a protein, that is encoded by the gene. In some embodiments, the gene product is a polynucleotide that is expressed by and/or encoded by the gene. In certain embodiments, the polynucleotide is an RNA. In some embodiments, the gene product is a messenger RNA (mRNA), a transfer RNA (tRNA), a ribosomal RNA, a small nuclear RNA, a small nucleolar RNA, an antisense RNA, long non-coding RNA, a microRNA, a Piwi-interacting RNA, a small interfering RNA, and/or a short hairpin RNA. In particular embodiments, the gene product is an mRNA.

In particular embodiments, assessing, measuring, determining, and/or quantifying amount or level of an RNA gene product includes a step of generating, polymerizing, and/or deriving a cDNA polynucleotide and/or a cDNA oligonucleotide from the RNA gene product. In certain embodiments, the RNA gene product is assessed, measured, determined, and/or quantified by directly assessing, measuring, determining, and/or quantifying a cDNA polynucleotide and/or a cDNA oligonucleotide that is derived from the RNA gene product.

In particular embodiments, the amount or level of a polynucleotide in a sample may be assessed, measured, determined, and/or quantified by any suitable means known in the art. For example, in some embodiments, the amount or level of a polynucleotide gene product can be assessed, measured, determined, and/or quantified by polymerase chain reaction (PCR), including reverse transcriptase (rt) PCR, droplet digital PCR, real-time and quantitative PCR (qPCR) methods (including, e.g., TAQMAN®, molecular beacon, LIGHTUP®, SCORPION®, SIMPLEPROBES™; see, e.g., U.S. Pat. Nos. 5,538,848; 5,925,517; 6,174,670; 6,329,144; 6,326,145 and 6,635,427); northern blotting; Southern blotting, e.g., of reverse transcription products and derivatives; array based methods, including blotted arrays, microarrays, or in situ-synthesized arrays; and sequencing, e.g., sequencing by synthesis, pyrosequencing, dideoxy sequencing, or sequencing by ligation, or any other methods known in the art, such as discussed in Shendure et al., *Nat. Rev. Genet.* 5:335-44 (2004) or Nowrousian, *Euk. Cell* 9 (9): 1300-1310 (2010), including such specific platforms as HELICOS®, ROCHE® 454, ILLUMINA®/SOLEXA®, ABI SOLID®, and POLONATOR® sequencing. In particular embodiments, the levels of nucleic acid gene products are measured by quantitative PCR (qPCR) methods, such qRT-PCR. In some embodiments, the qRT-PCR uses three nucleic acid sets for each gene, where the three nucleic acids comprise a primer pair together with a probe that binds between the regions of a target nucleic acid where the primers bind, known commercially as a TAQMAN® assay.

In particular embodiments, the expression of two or more of the genes are measured or assessed simultaneously. In certain embodiments, a multiplex PCR, e.g., a multiplex rt-PCR assessing or a multiplex quantitative PCR (qPCR) for, measuring, determining, and/or quantifying the level, amount, or concentration of two or more gene products. In some embodiments, microarrays (e.g., AFFYMETRIX®, AGILENT® and ILLUMINA®-style arrays) are used for assessing, measuring, determining, and/or quantifying the level, amount, or concentration of two or more gene products. In some embodiments, microarrays are used for assessing, measuring, determining, and/or quantifying the level, amount, or concentration of a cDNA polynucleotide that is derived from an RNA gene product. In some embodiments, the expression of one or more gene products, e.g., polynucleotide gene products, is determined by sequencing the gene product and/or by sequencing a cDNA polynucleotide that is derived from the from the gene product. In some embodiments, the sequencing is performed by a non-Sanger sequencing method and/or a next generation sequencing (NGS) technique. Examples of Next Generation Sequencing techniques include, but are not limited to Massively Parallel Signature Sequencing (MPSS), Polony sequencing, pyrosequencing, Reversible dye-terminator sequencing, SOLID® sequencing, Ion semiconductor sequencing, DNA nanoball sequencing, Helioscope® single molecule sequencing, Single molecule real time (SMRT®) sequencing, Single molecule real time (RNAP) sequencing, and Nanopore DNA sequencing.

In some embodiments, the NGS technique is RNA sequencing (RNA-Seq). In particular embodiments, the expression of the one or more polynucleotide gene products is measured, determined, and/or quantified by RNA-Seq. RNA-Seq, also called whole transcriptome shotgun sequencing determines the presence and quantity of RNA in a sample. RNA sequencing methods have been adapted for the most common DNA sequencing platforms (HiSeq systems (Illumina), 454 Genome Sequencer FLX System™ (Roche), Applied Biosystems SOLID® (Life Technologies), IonTorrent® (Life Technologies). These platforms require initial reverse transcription of RNA into cDNA. Conversely, the single molecule sequencer HeliScope® (Helicos BioSciences) is able to use RNA as a template for sequencing. A proof of principle for direct RNA sequencing on the PacBio RS platform has also been demonstrated (Pacific Bioscience). In some embodiments, the one or more RNA gene products are assessed, measured, determined, and/or quantified by RNA-seq. In some embodiments, the RNA-seq is a tag-based RNA-seq. In tag-based methods, each transcript is represented by a unique tag. Initially, tag-based approaches were developed as a sequence-based method to measure transcript abundance and identify differentially expressed genes, assuming that the number of tags (counts) directly corresponds to the abundance of the mRNA molecules. The reduced complexity of the sample, obtained by sequencing a defined region, was essential to make the Sanger-based methods affordable. When NGS technology became available, the high number of reads that could be generated facilitated differential gene expression analysis. A transcript length bias in the quantification of gene expression levels, such as observed for shotgun methods, is not encountered in tag-based methods. All tag-based methods are by definition strand specific. In particular embodiments, the one or more RNA gene products are assessed, measured, determined, and/or quantified by tag-based RNA-seq.

In some embodiments, the RNA-seq is a shotgun RNA-seq. Numerous protocols have been described for shotgun RNA-seq, but they have many steps in common: fragmentation (which can occur at RNA level or cDNA level, conversion of the RNA into cDNA (performed by oligo dT or random primers), second-strand synthesis, ligation of adapter sequences at the 3' and 5' ends (at RNA or DNA level) and final amplification. In some embodiments, RNA-seq can focus only on polyadenylated RNA molecules (mainly mRNAs but also some long noncoding RNAs (lncRNAs), small nucleolar RNAs (snoRNAs), pseudogenes and histones) if poly(A)+ RNAs are selected prior to fragmentation, or may also include non-polyadenylated RNAs if no selection is performed. In the latter case, ribosomal RNA (more than 80% of the total RNA pool) needs to be depleted prior to fragmentation. It is, therefore, clear that differences in capturing of the mRNA part of the transcriptome lead to a partial overlap in the type of detected transcripts. Moreover, different protocols may affect the abundance and the distribution of the sequenced reads. This makes it difficult to compare results from experiments with different library preparation protocols.

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library to yield FPKM normalized, e.g., by length of the genes/isoforms and number of reads in the library, to yield fragments per kilobase of exon per million mapped reads (FPKM) according to the gene length and total mapped reads. In some aspects, between-sample normalization is achieved by normalization, such as 75th quantile normalization, where each sample is scaled by the median of 75th quantiles from all samples, e.g., to yield quantile-normalized FPKM (FPKQ) values. The FPKQ values may be log-transformed (log 2).

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library. In some embodiments, read counts are provided as counts per million (CPM).

In some embodiments, relative gene expression is measured by comparing the CPM of a target gene to the CPM of a housekeeping gene. In some embodiments, the housekeeping gene is GAPDH. In some embodiments, the relative gene expression of a target gene is determined as the ratio of the CPM of the target gene to CPM of a housekeeping gene (e.g. GAPDH).

In some embodiments, among any of the provided compositions are pharmaceutical compositions containing a pharmaceutically acceptable carrier. In some embodiments, the dose of cells comprising cells produced by any of the methods disclosed herein, is provided as a composition or formulation, such as a pharmaceutical composition or formulation. Such compositions can be used in accord with the provided methods, articles of manufacture, and/or with the provided compositions, such as in the prevention or treatment of diseases, conditions, and disorders, such as neurodegenerative disorders.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservatives or mixtures thereof are typically present in an amount of about 0.0001% to about 2% by weight of the total composition. Carriers are described, e.g., by *Remington's Pharmaceutical Sciences* 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, *Remington: The Science and Practice of Pharmacy*, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as carbidopa-levodopa (e.g., Levodopa), dopamine agonists (e.g., pramipexole, ropinirole, rotigotine, and apomorphine), MAO B inhibitors (e.g., selegiline, rasagiline, and safinamide), catechol O-methyltransferase (COMT) inhibitors (e.g., entacapone and tolcapone), anticholinergics (e.g., benztropine and trihexylphenidyl), amantadine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The formulation or composition may also be administered in combination with another form of treatment useful for the particular indication, disease, or condition being prevented or treated with the cells or agents, where the respective activities do not adversely affect one another. Thus, in some embodiments, the pharmaceutical composition is administered in combination with deep brain stimulation (DBS).

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by stereotactic injection (e.g., using a catheter). In some embodiments, a given dose is administered by a single bolus administration of the cells or agent. In some embodiments, it is administered by multiple bolus administrations of the cells or agent, for example, over a period of months or years. In some embodiments, the agents or cells can be administered by stereotactic injection into the brain, such as in the striatum.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous. For example, non-pluripotent cells (e.g., fibroblasts) can be obtained from a subject, and administered to the same subject following reprogramming and differentiation. When administering a therapeutic composition (e.g., a pharmaceutical composition containing a genetically reprogrammed and/or differentiated cell or an agent that treats or ameliorates symptoms of a disease or disorder, such as a neurodegenerative disorder), it will generally be formulated in a unit dosage injectable form (solution, suspension, emulsion). Formulations include those for stereotactic administration, such as into the brain (e.g., the striatum).

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

IV. METHODS OF TREATMENT

Provided herein are methods of using any of the provided compositions for treating a disease or condition in a subject in need thereof. In particular embodiments, the composition is produced by the methods provided herein. Such methods and uses include therapeutic methods and uses, for example, involving administration of the therapeutic cells, or compositions containing the same, to a subject having a disease, condition, or disorder. In some embodiments the disease or condition is a neurodegenerative disease or condition. In some embodiments, the cells or pharmaceutical composition thereof is administered in an effective amount to effect treatment of the disease or disorder. Uses include uses of the cells or pharmaceutical compositions thereof in such methods and treatments, and in the preparation of a medicament in order to carry out such therapeutic methods. In some embodiments, the methods thereby treat the disease or condition or disorder in the subject.

The present disclosure relates to methods of lineage specific differentiation of pluripotent stem cells (PSCs), including embryonic stem (ES) cells and induced pluripotent stem cells (iPSCs), for use in neurodegenerative diseases. Specifically, the methods, compositions, and uses thereof provided herein contemplate differentiation of pluripotent stem cells for administration to subjects exhibiting a loss of dopamine (DA) neurons, including Parkinson's disease.

Parkinson's disease (PD) is the second most common neurodegenerative, estimated to affect 4-5 million patients worldwide. This number is predicted to more than double by 2030. PD is the second most common neurodegenerative disorder after Alzheimer's disease, affecting approximately 1 million patients in the US with 60,000 new patients diagnosed each year. Currently there is no cure for PD, which is characterized pathologically by a selective loss of midbrain DA neurons in the substantia nigra. A fundamental characteristic of PD is therefore progressive, severe and irreversible loss of midbrain dopamine (DA) neurons resulting in ultimately disabling motor dysfunction.

In some embodiments, a subject has a neurodegenerative disease. In some embodiments, the neurodegenerative disease comprises the loss of dopamine neurons in the brain. In some embodiments, the subject has lost dopamine neurons in the substantia nigra (SN). In some embodiments, the subject has lost dopamine neurons in the substantia nigra pas compacta (SNc). In some embodiments, the subject exhibits rigidity, bradykinesia, postural reflect impairment, resting tremor, or a combination thereof. In some embodiments, the subject exhibits abnormal $[_{18}F]$-L-DOPA PET scan. In some embodiments, the subject exhibits $[_{18}F]$-DG-PET evidence for a Parkinson's Disease Related Pattern (PDRP).

In some embodiments, the neurodegenerative disease is Parkinsonism. In some embodiments, the neurodegenerative disease is Parkinson's disease. In some embodiments, the neurodegenerative disease is idiopathic Parkinson's disease. In some embodiments, the neurodegenerative disease is a familial form of Parkinson's disease. In some embodiments, the subject has mild Parkinson's disease. In some embodiments, the subject has a Movement Disorder Society-Unified Parkinson's Disease Rating Scale (MDS-UPDRS) motor score of less than or equal to 32. In some embodiments, the subject has moderate or advanced Parkinson's disease. In some embodiments, the subject has mild Parkinson's disease. In some embodiments, the subject has a MDS-UPDRS motor score of between 33 and 60.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells is administered to the striatum of the subject. In some embodiments, the dose of cells is administered to one hemisphere of the subject's striatum. In some embodiments, the dose of cells is administered to both hemispheres of the subject's striatum.

In some embodiments, the dose of cells administered to the subject is about $5\times10^6$ cells. In some embodiments, the dose of cells administered to the subject is about $10\times10^6$ cells. In some embodiments, the dose of cells administered to the subject is about $15\times10^6$ cells. In some embodiments, the dose of cells administered to the subject is about $20\times10^6$ cells. In some embodiments, the dose of cells administered to the subject is about $25\times10^6$ cells. In some embodiments, the dose of cells administered to the subject is about $30\times10^6$ cells.

In some embodiments, the dose of cells comprises between at or about 250,000 cells per hemisphere and at or about 20 million cells per hemisphere, between at or about 500,000 cells per hemisphere and at or about 20 million cells per hemisphere, between at or about 1 million cells per hemisphere and at or about 20 million cells per hemisphere, between at or about 5 million cells per hemisphere and at or about 20 million cells per hemisphere, between at or about 10 million cells per hemisphere and at or about 20 million cells per hemisphere, between at or about 15 million cells per hemisphere and at or about 20 million cells per hemisphere, between at or about 250,000 cells per hemisphere and at or about 15 million cells per hemisphere, between at or about 500,000 cells per hemisphere and at or about 15 million cells per hemisphere, between at or about 1 million cells per hemisphere and at or about 15 million cells per hemisphere, between at or about 5 million cells per hemisphere and at or about 15 million cells per hemisphere, between at or about 10 million cells per hemisphere and at or about 15 million cells per hemisphere, between at or about 250,000 cells per hemisphere and at or about 10 million cells per hemisphere, between at or about 500,000 cells per hemisphere and at or about 10 million cells per hemisphere, between at or about 1 million cells per hemisphere and at or about 10 million cells per hemisphere, between at or about 5 million cells per hemisphere and at or about 10 million cells per hemisphere, between at or about 250,000 cells per hemisphere and at or about 5 million cells per hemisphere, between at or about 500,000 cells per hemisphere and at or about 5 million cells per hemisphere, between at or about 1 million cells per hemisphere and at or about 5 million cells per hemisphere, between at or about 250,000 cells per hemisphere and at or about 1 million cells per hemisphere, between at or about 500,000 cells per hemisphere and at or about 1 million cells per hemisphere, or between at or about 250,000 cells per hemisphere and at or about 500,00 cells per hemisphere.

In some embodiments, the dose of cells is between at or about 1 million cells per hemisphere and at or about 30 million cells per hemisphere. In some embodiments, the dose of cells is between at or about 5 million cells per hemisphere and at or about 20 million cells per hemisphere. In some embodiments, the dose of cells is between at or about 10 million cells per hemisphere and at or about 15 million cells per hemisphere.

In certain embodiments, the cells, or individual populations of sub-types of cells, are administered to the subject at a range of about 5 million cells per hemisphere to about 20 million cells per hemisphere or any value in between these ranges. Dosages may vary depending on attributes particular to the disease or disorder and/or patient and/or other treatments.

In some embodiments, the patient is administered multiple doses, and each of the doses or the total dose can be within any of the foregoing values. In some embodiments, the dose of cells comprises the administration of from or from about 5 million cells per hemisphere to about 20 million cells per hemisphere, each inclusive.

In some embodiments, the dose of cells, e.g. differentiated cells, is administered to the subject as a single dose or is administered only one time within a period of two weeks, one month, three months, six months, 1 year or more.

In the context of stem cell transplant, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as a day. Thus, in some contexts, the dose is a single or continuous administration of the specified number of cells, given or initiated at a single point in time. In some contexts, however, the dose is administered in multiple injections or infusions in a single period, such as by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time.

In some embodiments, the administration of the composition or dose, e.g., administration of the plurality of cell compositions, involves administration of the cell compositions separately. In some aspects, the separate administrations are carried out simultaneously, or sequentially, in any order.

In some embodiments, the subject receives multiple doses, e.g., two or more doses or multiple consecutive doses, of the cells. In some embodiments, two doses are administered to a subject. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. disease stage and/or likelihood or incidence of the subject developing adverse outcomes, e.g., dyskinesia.

In some embodiments, the dose of cells is generally large enough to be effective in improving symptoms of the disease.

In some embodiments, the cells are administered at a desired dosage, which in some aspects includes a desired dose or number of cells or cell type(s) and/or a desired ratio of cell types. In some embodiments, the dosage of cells is based on a desired total number (or number per kg of body weight) of cells in the individual populations or of individual cell types (e.g., $TH^+$ or $TH^-$). In some embodiments, the dosage is based on a combination of such features, such as a desired number of total cells, desired ratio, and desired total number of cells in the individual populations.

Thus, in some embodiments, the dosage is based on a desired fixed dose of total cells and a desired ratio, and/or based on a desired fixed dose of one or more, e.g., each, of the individual sub-types or sub-populations.

In particular embodiments, the numbers and/or concentrations of cells refer to the number of TH-negative cells. In other embodiments, the numbers and/or concentrations of cells refer to the number or concentration of all cells administered.

In some embodiments, the cells are administered at a desired dosage, which in some aspects includes a desired dose or number of cells or cell type(s) and/or a desired ratio of cell types. Thus, the dosage of cells in some embodiments is based on a total number of cells and a desired ratio of the individual populations or sub-types. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

Thus, in some embodiments, the dosage is based on a desired fixed dose of total cells and a desired ratio, and/or based on a desired fixed dose of one or more, e.g., each, of the individual sub-types or sub-populations.

In particular embodiments, the numbers and/or concentrations of cells refer to the number of TH-negative cells. In other embodiments, the numbers and/or concentrations of cells refer to the number or concentration of all cells administered.

In some aspects, the size of the dose is determined based on one or more criteria such as response of the subject to prior treatment, e.g., disease type and/or stage, and/or likelihood or incidence of the subject developing toxic outcomes, e.g., dyskinesia.

V. ARTICLES OF MANUFACTURE AND KITS

Also provided are articles of manufacture, systems, apparatuses, and kits useful in performing the provided methods. Also provided are articles of manufacture, including: (i) one or more reagents for differentiation of pluripotent stem cells into floor plate midbrain progenitor cells, determined dopamine (DA) neuron progenitor cells, and/or dopamine (DA) neurons; and (ii) instructions for use of the one or more reagents for performing any methods described herein.

In some of any such embodiments, the reagent for differentiation is or includes a small molecule, capable of inhibiting TGF-β/activin-Nodal signaling. In some of any such embodiments, the reagent for differentiation is or includes SB431542. In some of any such embodiments, the reagent for differentiation is or includes a small molecule, capable of activating SHH signaling. In some of any such embodiments, the reagent for activating SHH signaling is or includes SHH. In some of any such embodiments, the reagent for activating SHH signaling is or includes purmorphamine. In some of any such embodiments, the reagent for activating SHH signaling is or includes SHH and purmorphamine. In some of any such embodiments, the reagent for differentiation is or includes a small molecule, capable of inhibiting BMP signaling. In some of any such embodiments, the reagent for inhibiting BMP signaling is LDN193189. In some of any such embodiments, the reagent for differentiation is or includes a small molecule, capable of inhibiting GSK3β signaling. In some of any of such embodiments, the reagent is or includes CHIR99021. In some of any of such embodiments, the reagent for differentiation is or includes one or more of BDNF, GDNF, dbcAMP, ascorbic acid, TGFβ3, and DAPT. The reagents in the kit in one embodiment may be in solution, may be frozen, or may be lyophilized.

Also provided are articles of manufacture, including (i) any composition described herein; and (ii) instructions for administering the composition to a subject.

In some embodiments, the articles of manufacture or kits include one or more containers, typically a plurality of containers, packaging material, and a label or package insert on or associated with the container or containers and/or packaging, generally including instructions for use, e.g., instructions for reagents for differentiation of pluripotent cells, e.g., differentiation of iPSCs into floor plate midbrain progenitor cells, determined dopamine (DA) neuron progenitor cells, and/or dopamine (DA) neurons, and instructions to carry out any of the methods provided herein. In some aspects, the provided articles of manufacture contain reagents for differentiation and/or maturation of cells, for example, at one or more steps of the manufacturing process, such as any reagents described in any steps of Sections II and III.

Also provided are articles of manufacture and kits containing differentiated cells, such as those generated using the methods provided herein, and optionally instructions for use, for example, instructions for administering. In some embodiments, the instructions provide directions or specify methods for assessing if a subject, prior to receiving a cell therapy, is likely or suspected of being likely to respond and/or the degree or level of response following administration of differentiated cells expressing a recombinant receptor for treating a disease or disorder. In some aspects, the articles of manufacture can contain a dose or a composition of differentiated cells.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the compositions contained therein.

In some embodiments, the reagents and/or cell compositions are packaged separately. In some embodiments, each container can have a single compartment. In some embodiments, other components of the articles of manufacture or kits are packaged separately, or together in a single compartment.

VI. EXAMPLES

The following examples are included for illustrative purposes only and are not intended to limit the scope of the invention.

Example 1. Neuronal Differentiation of iPSCs

Induced pluripotent stem cells (iPSCs) were created from fibroblasts obtained from human donors with Parkinson's disease and subjected to a dopaminergic (DA) neuronal differentiation protocol. Expression of various midbrain markers was assessed.

iPSCs from the human donors were maintained by plating in Geltrex™-coated 6-well plates at 200,000 cells per $cm^2$. The cells were cultured without feeder cells in mTeSR™ 1-based media until they reached approximately 90% confluence (day 0). The iPSCs were then washed with sterile PBS and detached from the 6-well plates by enzymatic dissociation with Accutase®. The collected iPSCs were then used in the subsequent differentiation protocol.

A. Differentiation Protocol

The collected iPSCs were re-suspended in "basal induction media" (see below) and seeded under non-adherent conditions using 6-well or 24-well Aggre Well® plates. The cells were seeded under conditions to achieve the following concentrations: 500 cells/spheroid; 1,000 cells/spheroid, 2,000 cells/spheroid; 3,000 cells/spheroid; 10,000 cells/ spheroid; or 15,000 cells/spheroid. Following seeding of the cells, the 6-well or 24-well plates were immediately centrifuged at 200×g or 100×g for 3 minutes, respectively. Beginning at day 0, the media was supplemented with various small molecules as described below. The cells were cultured for 7 days, with media replacement as detailed below, to form spheroids. On day 7, the resulting spheroids were dissociated into single cells by enzymatic dissociation with Accutase®, and the cells were plated as monolayers at a concentration of 600,000 cells/cm$^2$ on substrate-coated 6-well plates (Geltrex®) for the remainder of culture, and further supplemented with nutrients and small molecules as described below.

A schematic of the exemplary non-adherent differentiation protocol is shown in FIG. 1 and Table E1, which depict the small molecule compounds that were added at various days during the differentiation method. From days 0 to 10, cells were cultured in the basal induction media, which was formulated to contain Neurobasal™ media and DMEM/F12 media at a 1:1 ratio (and with N-2 and B27 supplements, non-essential amino acids (NEAA), GlutaMAX™, L-glutamine, β-mercaptoethanol, and insulin), and supplemented with the appropriate small molecule compound(s). From days 11 to 25, cells were cultured in a "maturation media" (Neurobasal™ media containing N-2 and B27 supplements, non-essential amino acids (NEAA), and GlutaMAX™), and supplemented with the appropriate small molecule compound(s). The basal induction media also included a serum replacement.

TABLE E1

| Differentiation Protocol | | | | | | | | | |
|---|---|---|---|---|---|---|---|---|---|
| Day | Media | | Small Molecules | | | | | | |
| 0* | Basal Induction | 5% S | LDN | SB | SHH | PUR | CHIR | ROCKi | |
| 1 | Basal Induction | 5% S | LDN | SB | SHH | PUR | CHIR | | |
| 2 | Basal Induction | 2% S | LDN | SB | SHH | PUR | CHIR | | |
| 3 | Basal Induction | 2% S | LDN | SB | SHH | PUR | CHIR | | |
| 4 | Basal Induction | 2% S | LDN | SB | SHH | PUR | CHIR | | |
| 5 | Basal Induction | 2% S | LDN | SB | SHH | PUR | CHIR | | |
| 6 | Basal Induction | 2% S | LDN | SB | SHH | PUR | CHIR | | |
| 7* | Basal Induction | 2% S | LDN | | | | CHIR | ROCKi | |
| 8 | Basal Induction | 2% S | LDN | | | | CHIR | | |
| 9 | Basal Induction | 2% S | LDN | | | | CHIR | | |
| 10 | Basal Induction | 2% S | LDN | | | | CHIR | | |
| 11 | Maturation | | BDNF | GDNF | ascorbic | dbcAMP | CHIR | TGFβ3 | DAPT |
| 12 | Maturation | | BDNF | GDNF | ascorbic | dbcAMP | CHIR | TGFβ3 | DAPT |
| 13 | Maturation | | BDNF | GDNF | ascorbic | dbcAMP | | TGFβ3 | DAPT |
| 14 | Maturation | | BDNF | GDNF | ascorbic | dbcAMP | | TGFβ3 | DAPT |
| 15 | Maturation | | BDNF | GDNF | ascorbic | dbcAMP | | TGFβ3 | DAPT |
| Day 16: 1$^{st}$ Passage | | | | | | | | | |
| 16* | Maturation | | BDNF | GDNF | ascorbic | dbcAMP | | TGFβ3 | DAPT |
| 17 | Maturation | | BDNF | GDNF | ascorbic | dbcAMP | | TGFβ3 | DAPT |
| 18 | Maturation | | BDNF | GDNF | ascorbic | dbcAMP | | TGFβ3 | DAPT |
| 19 | Maturation | | BDNF | GDNF | ascorbic | dbcAMP | | TGFβ3 | DAPT |
| Day 20: 2$^{nd}$ Passage | | | | | | | | | |
| 20* | Maturation | | BDNF | GDNF | ascorbic | dbcAMP | | TGFβ3 | DAPT |
| 21 | Maturation | | BDNF | GDNF | ascorbic | dbcAMP | | TGFβ3 | DAPT |
| 22 | Maturation | | BDNF | GDNF | ascorbic | dbcAMP | | TGFβ3 | DAPT |
| 23 | Maturation | | BDNF | GDNF | ascorbic | dbcAMP | | TGFβ3 | DAPT |
| 24 | Maturation | | BDNF | GDNF | ascorbic | dbcAMP | | TGFβ3 | DAPT |
| 25 | Maturation | | BDNF | GDNF | ascorbic | dbcAMP | | TGFβ3 | DAPT |

S: Serum replacement;
LDN: LDN193189;
SB: SB431542;
SHH: recombinant mouse Sonic Hedgehog (rmSHH);
PUR: Purmorphamine;
CHIR: CHI99021;
ROCKi: Y-27632;
BDNF: recombinant human brain-derived neurotrophic factor (rhBDNF);
GDNF: recombinant human glial cell-derived neurotrophic factor (rhGDNF);
TGFβ3: recombinant human transforming growth factor beta 3 (rhTGFβ3);
dbcAMP: dibutyryl cyclic AMP;
Ascorbic: ascorbic acid;
*Indicates media supplemented with ROCK inhibitor (Y-27632)

Specifically, on day 0, the basal induction media was formulated to contain: 5% serum replacement, 0.1 μM LDN, 10 μM SB, 0.1 μg/mL SHH, 2 μM PUR, 2 μM of the GSK3B inhibitor CHIR99021, and 10 μM of the ROCK inhibitor Y-27632. The media was completely replaced on day 1 to provide the same concentration of the small molecule compounds as on day 0, except that no ROCK inhibitor was added. From days 2 to 6, the same concentration of the small molecule compounds as on day 1 were provided daily but by 50% media exchange; the concentrations of small molecules in the basal induction media were doubled on days 2 to 6, to ensure the same total concentration of compounds was added to the cell cultures. Also, the media on days 2 to 6 was formulated with 2% serum replacement.

On day 7 when the cells were transferred to substrate-coated plates, the basal induction media was formulated to contain: 2% serum replacement, 0.1 μM LDN, 10 μM SB, 2 μM CHIR99021, and 10 μM Y-27632. The media was replaced daily from days 8 to 10, with basal induction media formulated to contain 2% serum replacement, 0.1 μM LDN and 2 M CHIR99021.

Starting on day 11, the media was switched to maturation media formulated to contain: 20 ng/mL BDNF, 0.2 mM ascorbic acid, 20 ng/mL GDNF, 0.5 mM dbcAMP, and 1 ng/mL TGFβ3 (collectively, "BAGCT"), 10 μM DAPT, and 2 μM CHIR99021. The media was replaced on day 12 with the same media formulation containing the same concentrations of small molecule compounds as on day 11. From day 13 until harvest, the media was replaced either every day (days 13-17) or every other day (after day 17) with maturation media formulated to contain BAGCT and DAPT (collectively, "BAGCT/DAPT") at the same concentrations as on days 11 and 12.

On days 16 and 20, the cells were passaged by enzymatic dissociation with Dispase® and collagenase. Cells were re-suspended as small clumps and re-plated. On passaging days 16 and 20, cells were re-plated in maturation media further supplemented with the ROCK inhibitor.

B. Differentiation Status

On day 25, the differentiated cells were analyzed by immunohistochemistry for markers of midbrain DA neurons, including FOXA2 and tyrosine hydroxylase (TH), or were harvested by enzymatic dissociation and cryofrozen for downstream use or analysis. Nuclei were identified by DAPI staining. As shown in FIG. 2, an initial seeding density that produced 2,000 or 3,000 cells/spheroid resulted in discrete, FOXA2+TH+ neurons (see exemplary $FOXA2^+TH^+$ neuron, circled in top right panel of FIG. 2). At lower and higher seeding densities, cells were observed to be less differentiated.

Figure 3:
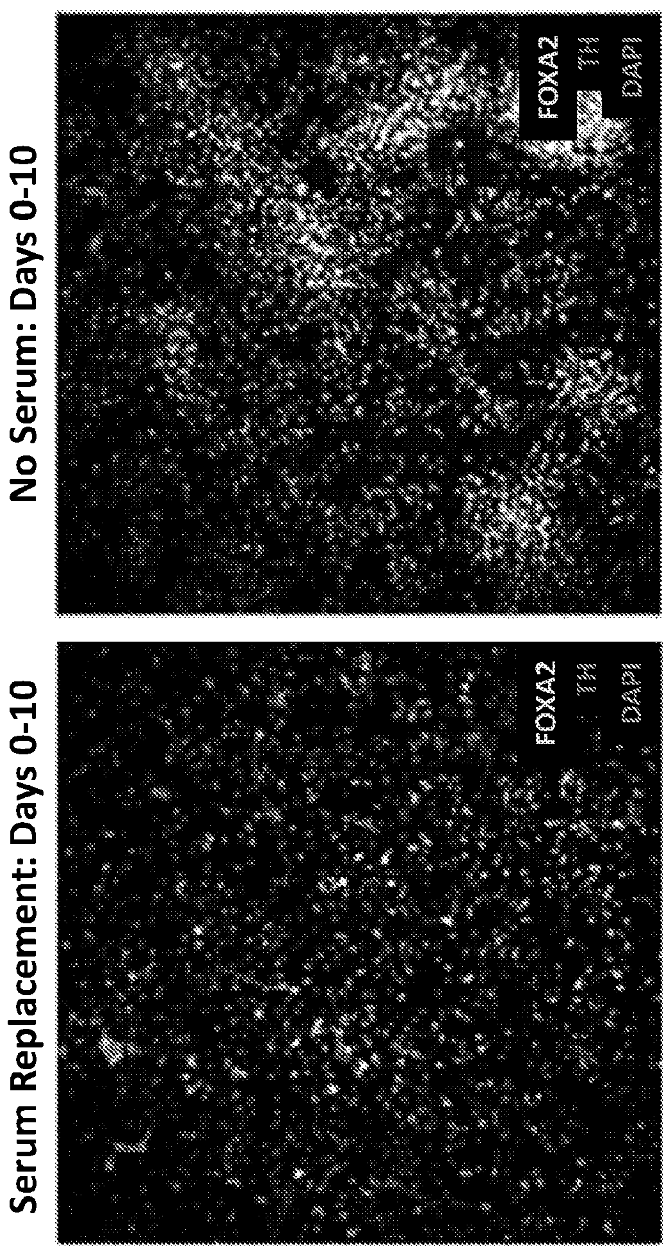
FIG. 3 shows FOXA2, TH, and DAPI expression by differentiated cells at day 10, grown with serum replacement or no serum.

To compare differentiation carried out in the presence of serum replacement versus in the absence of any serum, cells were grown under the same conditions, but in the absence of serum replacement from days 0-10. Cells grown without serum or without serum replacement exhibited reduced viability and lower $TH^+$ frequency, as determined by staining (FIG. 3; showing fewer $TH^+$ cells in "No Serum" panel).

In another experiment, cells were treated as described in the previous section, but the conditions under which the CHIR inhibitor was added from days 7 to 12 were modified by the addition of fibroblast growth factor 8 (FGF8) and with different concentrations of CHIR. All other aspects of media formulation and small molecule supplementation were maintained as shown in Table E1. Specifically, from days 7 to 12, either 2 μM, 4 μM, or 6 μM of CHIR was added, with or without 100 ng/mL fibroblast growth factor 8 (FGF8). At day 26 of the differentiation protocol, the number of $TH^+$ neurons was assessed. As compared to conditions without FGF8 and with only 2 μM CHIR, the addition of FGF8 and increased concentrations of CHIR did not result in more $TH^+$ neurons (data not shown).

These results are consistent with an observation that initial seeding density of the iPSCs, as well as the presence of serum replacement, affect the neuronal differentiation status of the cells produced by the described method. The results also support that 2 μM CHIR is sufficient to support appropriate differentiation, as adding FGF8 and/or increasing the concentration of CHIR from 2 μM to 4 μM or 6 μM did not further alter the number of $TH^+$ cells.

Example 2. Neuronal Differentiation Marker Expression

Expression levels of neuronal differentiation markers were compared between cells generated from the exemplary non-adherent method described above and cells generated by a different method, in which the cells were initially plated in Geltrex®-coated 6-well plates on day 0 and remained plated for the duration of the differentiation protocol ("adherent method"). The adherent method also differed from the non-adherent method, in that the small molecules were added on different schedules (FIG. 4). For all experimental conditions, cells were derived from the same human donor.

Figure 5:
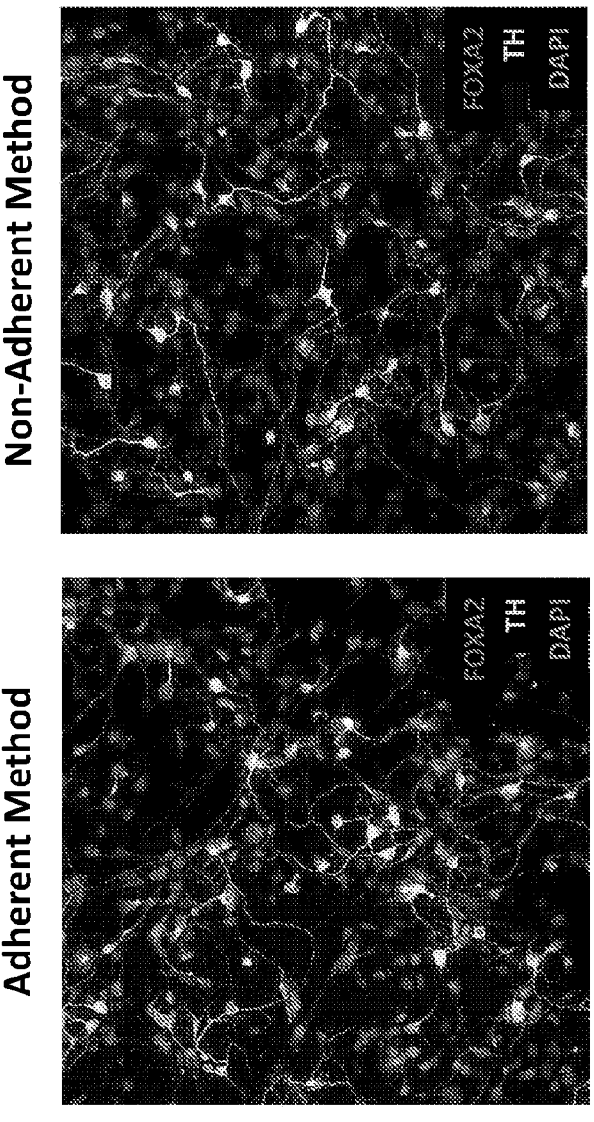
FIG. 5 shows FOXA2, TH, and DAPI expression by differentiated cells on day 25, derived from the exemplary adherent method or the exemplary non-adherent method.

Cells from the adherent and non-adherent methods were harvested on day 25 of differentiation and assessed for the presence of $FOXA2^+TH^+$ neurons. Nuclei were identified by staining with DAPI. As shown in FIG. 5, cultures of cells produced by the two methods appeared comparable, with both cultures exhibiting discrete, $FOXA2^+TH^+$ neurons.

Example 3. Tyrosine Hydroxylase (TH) Expression

Figure 6:
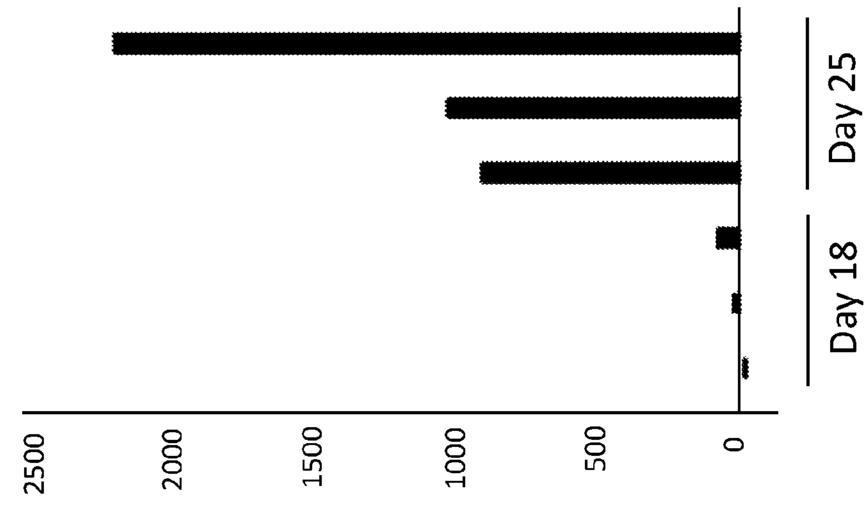
FIG. 6 shows tyrosine hydroxylase (TH) gene expression on day 18 and day 25 by cells differentiated by the exemplary non-adherent method.

The expression of tyrosine hydroxylase was compared between cells generated by the non-adherent method described above in Example 1. Cells were collected at either day 18 or day 25 (n=3). The data were normalized by a baselining method, in which the mean or median of the normalized counts of the samples from a particular time point was subtracted from the normalized counts of each sample from that time point. Analysis of the samples showed that TH gene expression is increased in cells at day 25, as compared to day 18 (FIG. 6). These findings are consistent with an observation that cells produced by the exemplary non-adherent method may be less differentiated at earlier time points of the method (e.g., at day 18 compared to day 25).

Figure 7:
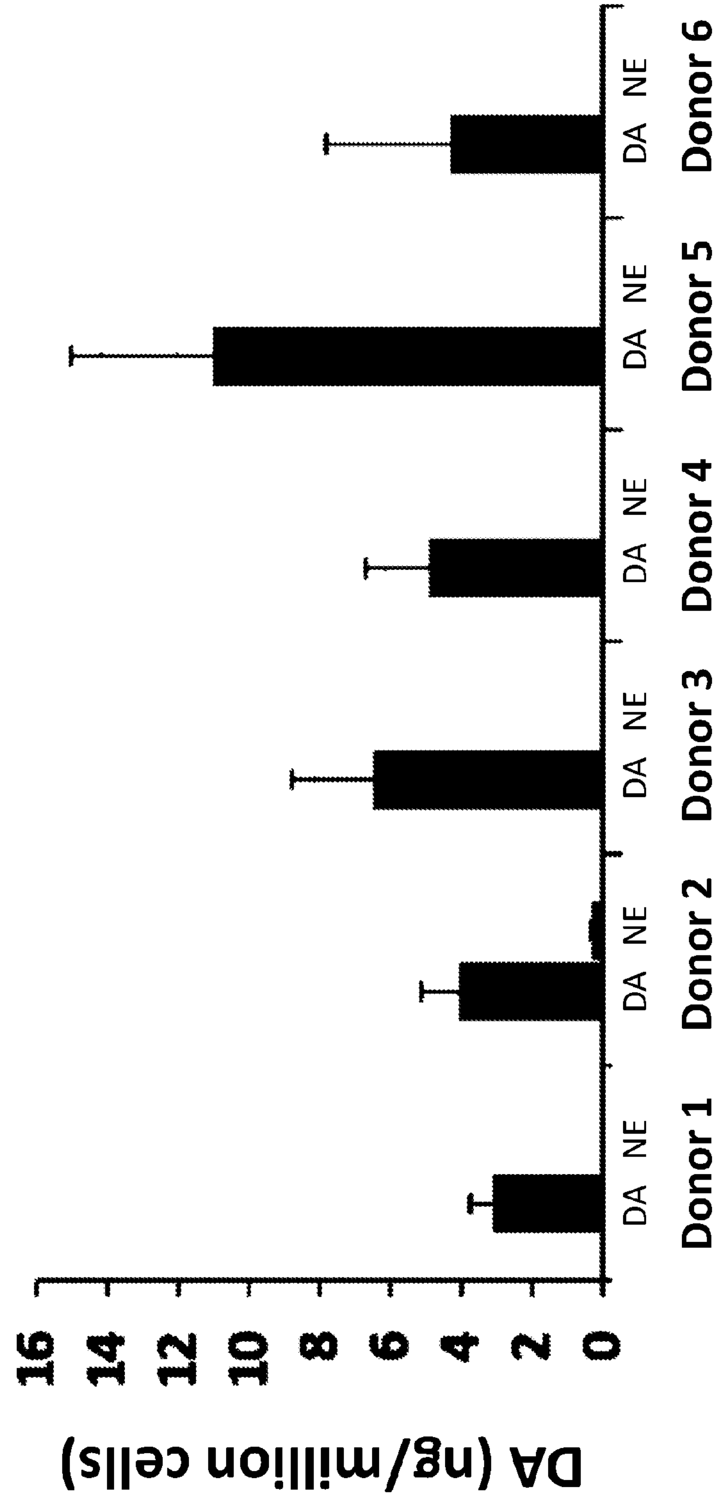
FIG. 7 shows dopamine (DA) and norepinephrine (NE) production by cells cultured to day 75 (ng/million cells assayed).

Example 4 Assessment of Dopamine Production in Differentiated Cells at Various Timepoints Induced pluripotent stem cell (iPSC) lines were created from fibroblasts obtained from six different human donors and subjected to the adherent dopaminergic (DA) neuronal differentiation method described in Example 2. The differentiated cells were cultured to day 75 and then stimulated with 56 mM KCl in Hank's buffered saline solution (HBSS) for measurement of dopamine (DA) and norepinephrine (NE) production by high performance liquid chromatography (HPLC). As shown in FIG. 7, differentiated cells from each of the six donor cell lines exhibited DA production, ranging from 3 ng to 11 ng per million cells assayed. Norepinephrine (NE) production was either not detected or detected at low levels (<1 ng per million cells assayed). As DA is an intermediate in the production of NE, but no or low NE production was observed, the findings are consistent with an observation that the differentiation protocol is able to produce cells capable of producing dopaminergic neurons.

Example 5. Analysis of Gene Expression in Differentiated Cells

Cells were differentiated by the non-adherent differentiation protocol described in Example 1 and collected at various days of differentiation for analysis of gene expression by RNAseq.

Figure 8A:
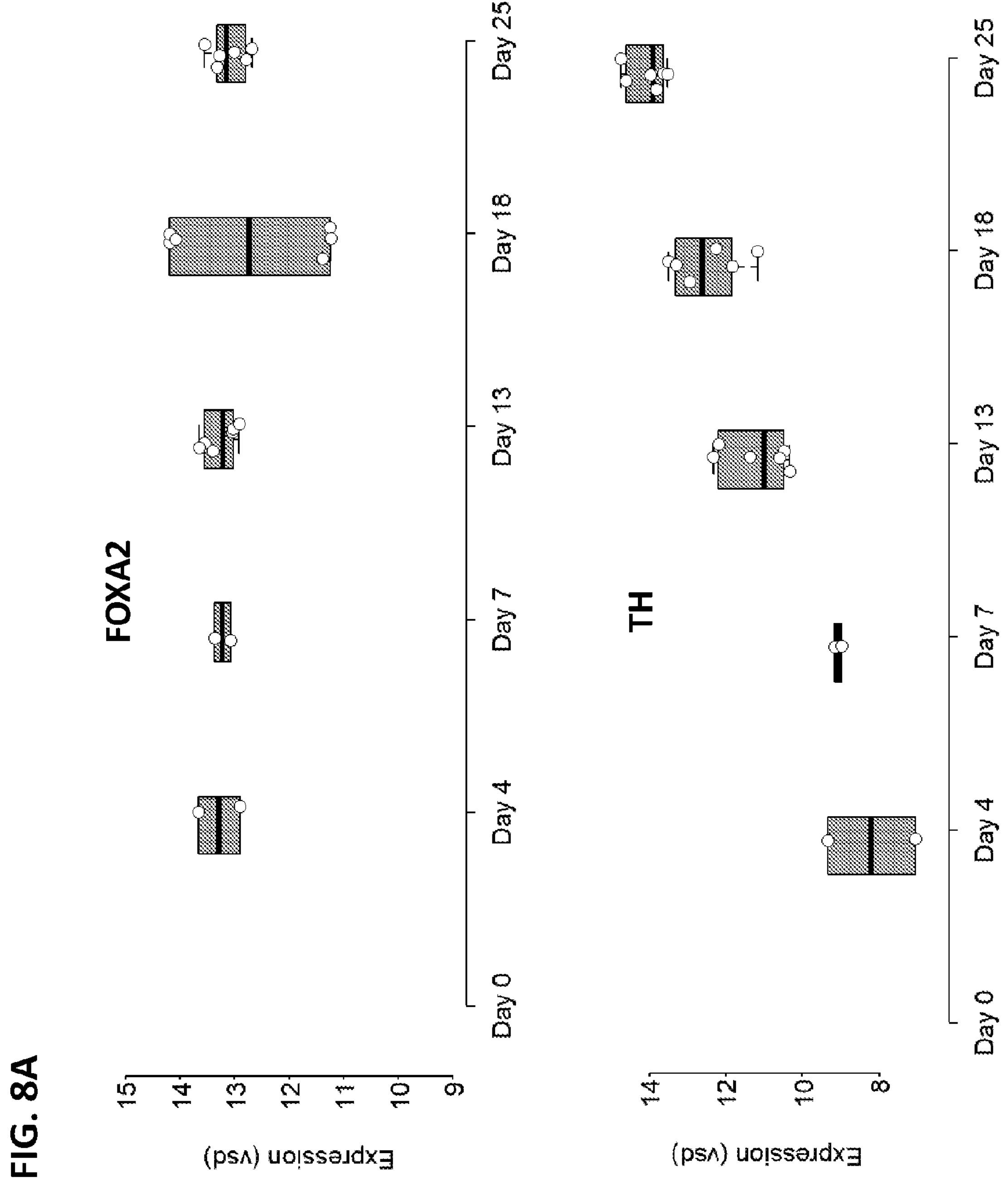
FIG. 8A shows FOXA2 and TH gene expression in cells differentiated by the exemplary non-adherent method on various days of differentiation.
Figure 8B:
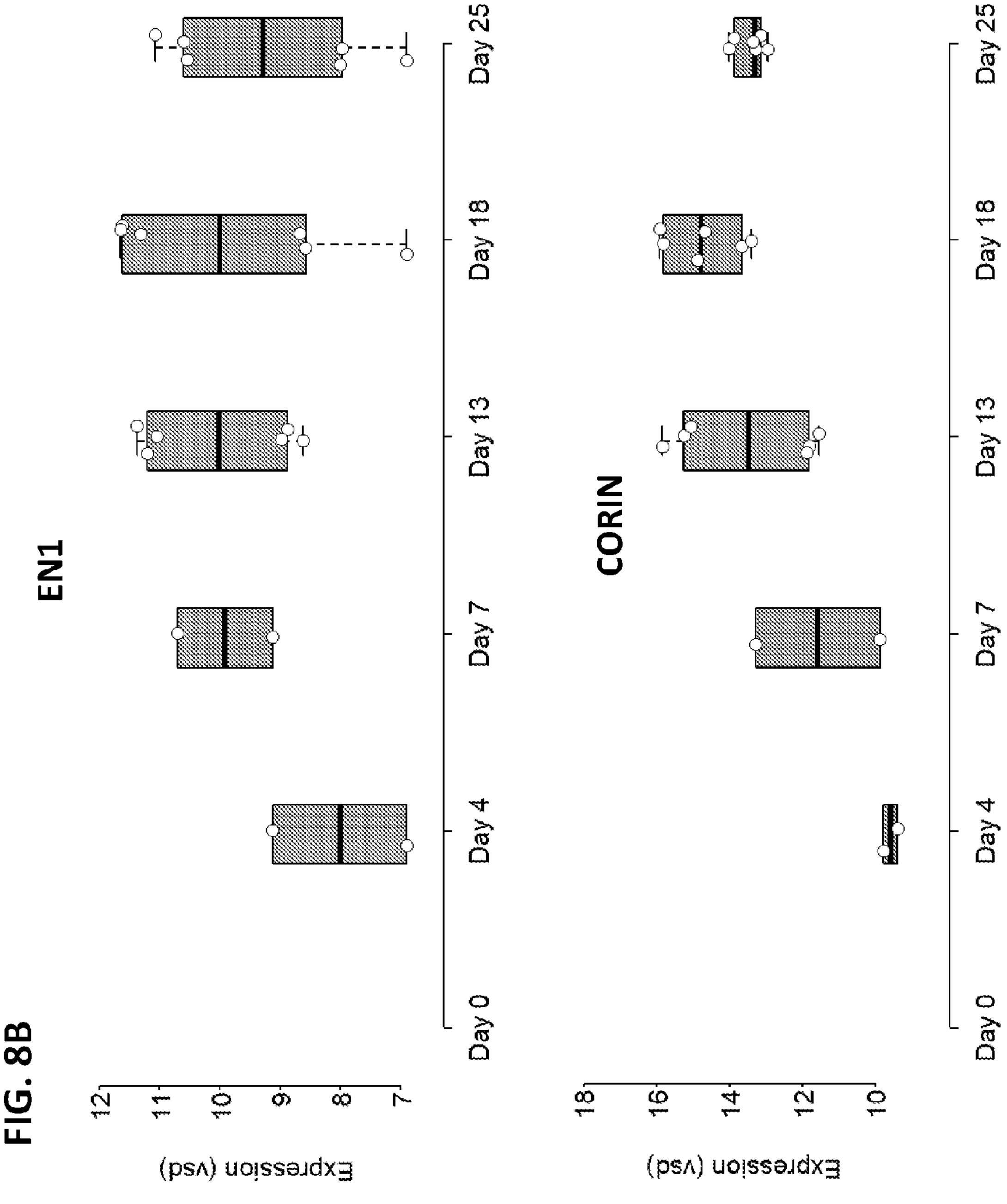
FIG. 8B shows EN1 and CORIN gene expression in cells differentiated by the exemplary non-adherent method on various days of differentiation.
Figure 8C:
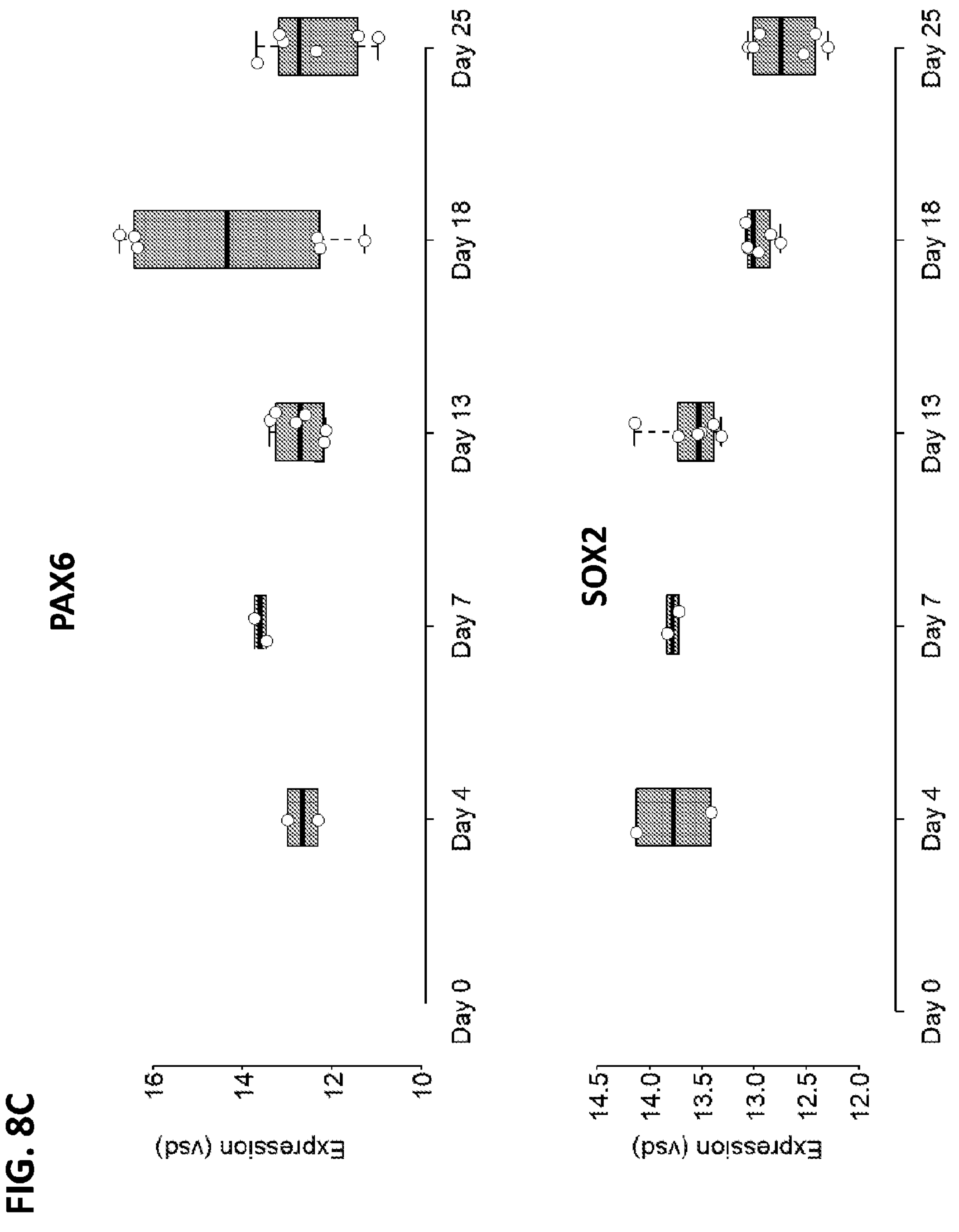
FIG. 8C shows PAX6 and SOX2 gene expression in cells differentiated by the exemplary non-adherent method on various days of differentiation.

As shown in FIG. 8A, differentiated cells were observed to express midbrain DA neuron genes FOXA2 and TH. In particular, TH gene expression appeared to increase on day 25 compared to day 18, which is consistent with the results observed in Example 3. Beginning about day 4 or day 7, the differentiated cells were also observed to express EN1 and CORIN, genes expressed by A9 progenitors during fetal development (FIG. 8B). Low expression of PAX6 and SOX2, early neural progenitor markers, was also observed on differentiated cells (FIG. 8C). Notably, expression of SOX2 tended to decrease over differentiation time, particularly by day 18 and further by day 25. In particular, these findings are consistent with an observation that the cells became increasingly differentiated (i.e. committed to a dopaminergic neuronal fate) over the course of the 25 days. Differences between day 18 and day 25 cells are consistent with day 18 cells being less differentiated but exhibiting features of determined dopaminergic precursor cells committed to be dopaminergic neurons, such that they are not able to differentiate into non-dopaminergic cells.

To assess gene expression in cells differentiated to day 18 or day 25, differential gene expression was analyzed between cells harvested at day 18 and cells harvested at day 25 of the non-adherent differentiation method by RNAseq. A false discovery rate (FDR) of <0.05 and a Log2-fold change of >0 were used to identify and generate lists of significantly differentially expressed genes that were upregulated ("upregulated" list) and downregulated ("downregulated" list) at day 25 compared to day 18.

The upregulated list of differentially expressed genes was compared to a publicly available list of genes related to neurite outgrowth (available at amigo.geneontology.org/amigo/term/GO: 0043005). A total of 132 genes in the "upregulated" list were identified as being neurite outgrowth-related genes that were differentially expressed between day 18 and day 25, in particular genes that were upregulated at day 25 compared to day 18. When the identified differentially expressed neurite outgrowth-related genes were ranked by significance, the top ten (10) significant genes were found to be, in order: CALCA, GLRA2, MAPT, CAMK2B, SYT13, LHFPL4, RET, KCND3, NSG2, and SNAP25.

Similarly, the downregulated list of differentially expressed genes was compared to a publicly available list of genes related to mitosis (available at amigo.geneontology.org/amigo/term/GO: 0000278). A total of 108 genes in the "downregulated" list were identified as being mitosis-related genes that were differentially expressed between day 18 and day 25, in particular genes that were downregulated at day 25 compared to day 18. When the identified differentially expressed mitosis-related genes were ranked by significance, the top ten (10) significant genes were found to be, in order: NEUROG1, EDN3, HES1, PSRC1, NEK6, IQGAP3, USP44, CEP55, KIF20A, and AURKA.

The relative expression of genes in the differentially upregulated and downregulated lists was determined by measuring the gene expression of each of the genes in six different differentiated samples from each of days 18 and 25, relative to GAPDH expression. In particular, counts per million (CPM) estimates of target genes and GAPDH were normalized to the RNAseq library size. Count values represented a gene-level analysis. For each of day 18 and day 25, a minimum, maximum, and average relative expression among the sample for each gene was generated as the ratio of the CPM of the target gene to the CPM of GAPDH. The same analysis was repeated for target genes EN1, CORIN, and TH. These values are shown below in Table E2 for the top 10 upregulated and downregulated differentially expressed genes (as ranked by significance), as well as for EN1, CORIN, and TH.

One or more of the most significantly, differentially expressed genes between days 18 and 25 may serve as a genetic expression signature by which day 18 cells can be identified.

TABLE E2

| Relative Gene Expression | | | | |
|---|---|---|---|---|
| Gene | Day | Minimum (CPM target/ CPM GAPDH) | Maximum (CPM target/ CPM GAPDH) | Average (CPM target/ CPM GAPDH) |
| CALCA | 18 | 1.77E−05 | 0.000408 | 0.00016 |
| CALCA | 25 | 0.008692 | 0.01485 | 0.011583 |
| GLRA2 | 18 | 6.11E−05 | 0.000585 | 0.000234 |
| GLRA2 | 25 | 0.002785 | 0.014048 | 0.007385 |
| MAPT | 18 | 0.012845 | 0.054135 | 0.032348 |
| MAPT | 25 | 0.110682 | 0.347361 | 0.195724 |
| CAMK2B | 18 | 0.006977 | 0.027107 | 0.015879 |
| CAMK2B | 25 | 0.074987 | 0.125025 | 0.098072 |
| SYT13 | 18 | 0.003279 | 0.009749 | 0.00611 |
| SYT13 | 25 | 0.016662 | 0.124165 | 0.054631 |
| NEUROG1 | 18 | 4.32E−05 | 0.000944 | 0.000399 |
| NEUROG1 | 25 | 0 | 2.87E−05 | 1.15E−05 |
| EDN3 | 18 | 0.000755 | 0.028946 | 0.010579 |
| EDN3 | 25 | 0.000126 | 0.000975 | 0.00049 |
| HES1 | 18 | 0.006051 | 0.018205 | 0.011879 |
| HES1 | 25 | 0.002255 | 0.004073 | 0.003242 |
| PSRC1 | 18 | 0.018596 | 0.026996 | 0.022928 |
| PSRC1 | 25 | 0.006497 | 0.009065 | 0.007423 |
| NEK6 | 18 | 0.003526 | 0.101062 | 0.047008 |
| NEK6 | 25 | 0.00232 | 0.01129 | 0.005453 |
| EN1 | 18 | 0 | 0.003082 | 0.001346 |
| EN1 | 25 | 0 | 0.001257 | 0.000484 |
| CORIN | 18 | 0.026416 | 0.171635 | 0.0912 |
| CORIN | 25 | 0.014276 | 0.043493 | 0.027472 |
| TH | 18 | 0.001687 | 0.020282 | 0.010073 |
| TH | 25 | 0.026186425 | 0.066965347 | 0.041877026 |

The values given are counts per million (CPM) of the target gene/CPM of GAPDH, and are measures of relative expression.

Together, these findings indicate that the cells become increasingly committed to a determined, neuronal fate with increasing days of the exemplary differentiation protocol. In particular, mitosis-related genes decreased from day 18 to day 25, indicating a shift away from a pluripotent, self-renewal state, toward a more defined cell-type, while neurite outgrowth-related genes increased from day 18 to day 25, indicating a shift toward a defined neuronal phenotype. The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of differentiating neural cells, the method comprising:

(a) performing a first incubation comprising culturing pluripotent stem cells in a non-adherent culture vessel under conditions to produce a cellular spheroid, wherein beginning at the initiation of the first incubation the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3β (GSK3β) signaling, wherein day 0 is the first day on which the pluripotent stem cells are exposed to the inhibitor of TGF-β/activin-Nodal signaling and the inhibitor of bone morphogenetic protein (BMP) signaling; and (b) performing a second incubation comprising culturing cells of the spheroid in a substrate-coated culture vessel under conditions to neurally differentiate the cells.

2. The method of claim 1, wherein the second incubation begins on about day 7.

3. The method of claim 1, wherein the cells are exposed:

(i) to the inhibitor of TGF-β/activin-Nodal signaling up to a day at or before day 7;

(ii) to the inhibitor of TGF-β/activin-Nodal beginning at day 0 and through day 6, inclusive of each day;

(iii) to the at least one activator of SHH signaling up to a day at or before day 7;

(iv) to the at least one activator of SHH signaling beginning at day 0 and through day 6, inclusive of each day;

(v) to the inhibitor of BMP signaling up to a day at or before day 11;

(vi) to the inhibitor of BMP signaling beginning at day 0 and through day 10, inclusive of each day;

(vii) to the inhibitor of GSK3B signaling up to a day at or before day 13;

(viii) to the inhibitor of GSK3B signaling beginning at day 0 and through day 12, inclusive of each day;

(ix) to transforming growth factor beta-3 (TGFβ3), ascorbic acid, GDNF, and dbcAMP (collectively, "BAGCT") and an inhibitor of Notch signaling beginning on day 11; and/or (x) to BAGCT and an inhibitor of Notch signaling beginning at day 11 and until harvest of the neurally differentiated cells, optionally until day 18, optionally until day 25.

4. The method of claim 1, wherein culturing the cells under conditions to neurally differentiate the cells comprises exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3) (collectively, "BAGCT"); and (vi) an inhibitor of Notch signaling.

5. The method of claim 1, wherein the method comprises:

(a) beginning at the initiation of the first incubation day, the cells are exposed to (i) an inhibitor of TGF-β/activin-Nodal signaling through day 6, each day inclusive; (ii) at least one activator of Sonic Hedgehog (SHH) signaling through day 6, each day inclusive; (iii) an inhibitor of bone morphogenetic protein (BMP) signaling through day 6, each day inclusive; and (iv) an inhibitor of glycogen synthase kinase 3β (GSK3β) signaling through day 6, each day inclusive; and (b) the performing a second incubation begins on day 7, and comprises culturing the cells in a culture vessel coated with a substrate selected from the group consisting of: laminin, collagen, entactin, heparin sulfate proteoglycans, and combinations thereof, wherein beginning on day 7, the cells are exposed to (i) an inhibitor of BMP signaling and (ii) an inhibitor of GSK3β signaling; and beginning on day 11, the cells are exposed to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3) (collectively, "BAGCT"); and (vi) an inhibitor of Notch signaling.

6. The method of claim 1, further comprising harvesting the neurally differentiated cells, optionally wherein the harvesting is carried out at about day 16 or later, wherein the harvesting is carried out between day 18 and day 25, and/or wherein the harvesting is carried out at or about day 18 or about at day 25.

7. The method of claim 1, wherein the neurally differentiated cells are determined dopaminergic neuron progenitor cells, optionally wherein the dopaminergic neuron progenitor cells are capable of innervating host tissue upon transplantation into a subject.

8. The method of claim 1, wherein, prior to performing the second incubation, the spheroid is dissociated to produce a cell suspension, and cells of the cell suspension are cultured in the substrate-coated culture vessel, optionally wherein the dissociating is carried out at a time when the spheroid cells express at least one of PAX6 and OTX2, and/or wherein the dissociating is carried out on about day 7, and/or wherein the spheroid is dissociated by enzymatic dissociation.

9. The method of claim 1, wherein the inhibitor of TGF-β/activin-Nodal signaling is SB431542; wherein the at least one activator of SHH signaling is SHH protein, purmorphamine, C25II SHH protein, or a combination thereof; and/or wherein the inhibitor of BMP signaling is LDN193189, and/or wherein the inhibitor of GSK3β signaling is CHIR99021; and/or wherein the inhibitor of Notch signaling is DAPT.

10. The method claim 1, wherein the culturing in the first incubation and/or the second incubation is carried out in media comprising serum or a serum replacement, or wherein the cells are cultured in the absence of serum for the duration of culture.

11. The method of claim 1, wherein the cells are exposed to an inhibitor of Rho-associated protein kinase (ROCK) signaling on day 0, day 8, day 16, and/or day 20.

12. The method of claim 1, wherein the first incubation is performed in media that comprises the inhibitor of TGF-β/activin-Nodal signaling, the activator of SHH signaling, the inhibitor of BMP signaling, and the inhibitor of GSK3β signaling, and at least about 50% of the media is replaced daily or every other day, or every third day.

13. The method of claim 6, further comprising formulating the harvested cells with a cryoprotectant, optionally further comprising cryopreserving the harvested cells, and optionally thawing the cells prior to use.

14. The method of claim 1, wherein the pluripotent stem cells are embryonic stem (ES) cells, induced pluripotent stem cells (iPSCs), or a combination thereof.

15. The method of claim 1, wherein the pluripotent stem cells are human induced pluripotent stem cells, and/or wherein the pluripotent stem cells are autologous to a subject to be treated with the neurally differentiated cells or allogeneic to a subject to be treated with the neurally differentiated cells.

16. The method of claim 15, wherein the pluripotent stem cells are hypoimmunogenic, optionally wherein the pluripotent stem cells are engineered to (a) remove genes encoding one or more of polymorphic HLA-A/-B/-C and HLA class II molecules; and (b) to provide genes encoding one or more of PD-L1, HLA-G, and CD47, optionally into a AAVS1 safe harbor locus.

17. A method of differentiating neural cells, the method comprising:

(a) performing a first incubation comprising culturing pluripotent stem cells in a culture vessel that is coated with a substrate selected from one or more of laminin, collagen, entactin, heparin sulfate proteoglycans, and combinations thereof, wherein beginning at the initiation of the first incubation the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling; and (iv) an inhibitor of glycogen synthase kinase 3β (GSK3β) signaling, wherein day 0 is the first day on which the pluripotent stem cells are exposed to the inhibitor of TGF-β/activin-Nodal signaling and the inhibitor of bone morphogenetic protein (BMP) signaling, wherein the method does not comprise exposing the cells to fibroblast growth factor 8 (FGF8); and (b) performing a second incubation comprising culturing cells obtained in step (a) in a substrate-coated culture vessel under conditions to neurally differentiate the cells.

18. The method of claim 17, wherein the substrate comprises laminin.

19. The method of claim 17, wherein the inhibitor of TGF-β/activin-Nodal signaling is SB431542.

20. The method of claim 17, wherein the at least one activator of SHH signaling is SHH protein, purmorphamine, C25II SHH protein, or a combination thereof.

21. The method of claim 17, wherein the inhibitor of BMP signaling is LDN193189.

22. The method of claim 17, wherein the inhibitor of GSK3B signaling is CHIR99021.

23. The method of claim 1, wherein the method does not comprise exposing the cells to fibroblast growth factor 8 (FGF8).

24. A method of differentiating neural cells, the method comprising:

(a) performing a first incubation comprising culturing pluripotent stem cells in a culture vessel that is coated with a substrate selected from one or more of laminin, collagen, entactin, heparin sulfate proteoglycans, and combinations thereof, wherein beginning at the initiation of the first incubation the cells are exposed to (i) an inhibitor of TGF-β/activin-Nodal signaling; (ii) at least one activator of Sonic Hedgehog (SHH) signaling; (iii) an inhibitor of bone morphogenetic protein (BMP) signaling comprising LDN193189; and (iv) an inhibitor of glycogen synthase kinase 3β (GSK3β) signaling, wherein day 0 is the first day on which the pluripotent stem cells are exposed to the inhibitor of TGF-β/activin-Nodal signaling and the inhibitor of bone morphogenetic protein (BMP) signaling; and (b) performing a second incubation comprising culturing cells obtained in step (a) in a substrate-coated culture vessel under conditions to neurally differentiate the cells.

25. The method of claim 24, wherein the substrate comprises laminin.

26. The method of claim 24, wherein the inhibitor of TGF-β/activin-Nodal signaling is SB431542.

27. The method of claim 24, wherein the at least one activator of SHH signaling is SHH protein, purmorphamine, C25II SHH protein, or a combination thereof.

28. The method of claim 24, wherein the inhibitor of GSK3β signaling is CHIR 99021.

29. The method of claim 24, wherein the method does not comprise exposing the cells to fibroblast growth factor 8 (FGF8).

* * * * *